US006468791B1

(12) United States Patent
Tanzi et al.

(10) Patent No.: US 6,468,791 B1
(45) Date of Patent: Oct. 22, 2002

(54) CHROMOSONE 1 GENE AND GENE PRODUCTS RELATED TO ALZHEIMER'S DISEASE

(75) Inventors: Rudolph E. Tanzi, Canton, MA (US); Gerard D. Schellenberg, Seattle, WA (US); Wilma Wasco, Cambridge, MA (US); Ephrat Levy-Lahad, Seattle, WA (US); Thomas D. Bird, Seattle, WA (US); David J. Galas, Mercer Island, WA (US)

(73) Assignees: The General Hospital Corp., Boston, MA (US); University of Washington, Seattle, WA (US)

( * ) Notice: Subject to any disclaimer, the term of this patent is extended or adjusted under 35 U.S.C. 154(b) by 0 days.

(21) Appl. No.: 09/375,318

(22) Filed: Aug. 16, 1999

Related U.S. Application Data

(63) Continuation of application No. 08/675,876, filed on Jul. 5, 1996, now abandoned
(60) Provisional application No. 60/002,328, filed on Aug. 14, 1995, provisional application No. 60/002,174, filed on Aug. 11, 1995, provisional application No. 60/001,675, filed on Jul. 28, 1995, and provisional application No. 60/000,956, filed on Jul. 7, 1995.

(51) Int. Cl.$^7$ ........................... C12N 15/00; C12N 15/63
(52) U.S. Cl. .................. 435/325; 435/69.1; 435/320.1; 536/23.1; 536/24.31; 536/23.5
(58) Field of Search ............................ 536/23.1, 24.31, 536/23.5; 435/320.1, 69.1, 325; 514/44; 424/93.2, 93.21

(56) References Cited

U.S. PATENT DOCUMENTS 5,840,540 A * 11/1998 St. George-Hyslop et al. .. 435/69.1

OTHER PUBLICATIONS

Anderson, Human Gene Therapy, 1998, vol. 392, pp. 25–30.*
Crystal, Science, 1995, vol. 270, pp. 404–410.*
Ngo et al., Computational Complexity Protein Structure Prediction and the Levinthal Paradox, Merz et al., (ed), Boston, MA, 1994, pp. 492–495.*
Mastrangelo et al, Seminars in Oncology, vol. 23, 1996, pp. 4–21.*
Bellanné–Chantelot et al., "Mapping the Whole Human Genome by Fingerprinting Yeast Artificial Chromosomes," *Cell 70*: 1059–1068, Sep. 18, 1992.
Benjamin et al., "Protective effect of apoE ε2 in Alzheimer's disease," *The Lancet 344*: 473, Aug. 13, 1994.
Bird et al., "Familial Alzheimer's Disease in American Descendants of the Volga Germans: Probable Genetic Founder Effect," *Annals of Neurology 23*(1):25–31, Jan. 1988.
Bird et al., "Phenotypic Heterogeneity in Familial Alzheimer's Disease: A Study of 24 Kindreds," *Annals of Neurology 25*(1): 12–25, Jan. 1989.
Bird et al., *Heterogeneity of Alzheimer's Disease*, F. Boller et al. (eds.), Springer–Verlag Berlin Heidelberg, 1992, "Familial Alzheimer's Disease in Germans from Russia: A Model of Genetic Heterogenetic in Alzheimer's Disease," pp. 118–129.
Bird, Thomas D., "Evaluating Family Histories And Traditions For Evidence Of Medical Illness Using Alzheimer's Disease As A Model," *Journal of the American Historical Society of Germans from Russia 14*(3): 49–54, Fall 1991.
Brousseau et al., "Confirmation of the ε4 allele of the apolipoprotein E gene is a risk factor for late–onset Alzheimer's disease," *Neurology 44*: 342–344, Feb. 1994.
Cook et al., "Studies in aging of the brain: IV. Familial Alzheimer disease: Relation to transmissible dementia, aneuploidy, and microtubular defects," *Neurology 29*: 1402–1412, Oct. 1979.
Corder et al., "Gene Dose of Apolipoprotein E Type 4 Allele and the Risk of Alzheimer's Disease in Late Onset Families," *Science 261*: 921–923, Aug. 13, 1993.
Corder et al., "Protective effect of apolipoprotein E type 2 allele for late onset Alzheimer disease," *Nature Genetics 7*: 180–184, Jun. 1994.
Feldman et al., "Familial Alzheimer's disease," *Neurology 13*(10): 811–824, 1960.
Goate et al., "Segregation of a missense mutation in the amyloid precursor protein gene with familial Alzheimer's disease," *Nature 349*: 704–706, Feb. 21, 1991.
Goudsmit et al., "Familial Alzheimer's Disease in two Kindreds of the Same Geographic and Ethnic Origin," *Journal of the Neurological Science 49*: 79–89, 1981.
Heston and White, "Pedigrees of 30 Families with Alzheimer Disease: Associations with Defective Organization of Microfilaments and Microtubules," *Behavior Genetics 8*(4): 315–331, 1978.
Kamino et al., "Linkage and Mutational Analysis of Familial Alzheimer Disease Kindreds for the APP Gene Region," *Am. J. Hum. Genet. 51*: 998–1014, 1992.
Kuusisto et al., "Association of apolipoprotein E phenotypes with late onset Alzheimer's disease: population based study," *BMJ 309*: 636–638, Sep. 10, 1994.

(List continued on next page.)

*Primary Examiner*—Daue Trong Nguyen
(74) *Attorney, Agent, or Firm*—Seed IP Law Group

(57) ABSTRACT

The present invention discloses nucleic acid molecules encoding AD4 gene products, expression vectors and host cells suitable for expressing such gene products. Also disclosed are methods for treating, preventing, and diagnosing Alzheimer's Disease.

11 Claims, 22 Drawing Sheets

OTHER PUBLICATIONS

Lannfelt et al., "No linkage to chromosome 14 in Swedish Alzheimer's disease families," *Nature Genetics 4*: 218–219, Jul. 1993.

Liddell et al., "Confirmation of association between the e4 allele of apolipoprotein E and Alzheimer's disease," *J. Med. Genet. 31*: 197–200, 1994.

Martin et al., "Early–onset Alzheimer's disease in 2 large Belgian families," *Neurology 41*: 62–68, Jan. 1991.

Munroe et al., "Systematic screening of an arrayed cDNA library by PCR," *Proc. Natl. Acad. Sci. USA 92*: 2209–2213, Mar. 1995.

Nee et al., "A Family With Histologically Confirmed Alzheimer's Disease," *Arch. Neurol. 40*: 203–208, Apr. 1983.

Nee et al., "Dementia of the Alzheimer type: Clinical and family study of 22 twin pairs," *Neurology 37*: 359–363, Mar. 1987.

Pericak–Vance et al., "Genetic Linkage Studies in Alzheimer's Disease Families," *Experimental Neurology 102*: 271–279, 1988.

Rapoport et al., "Discordance and concordance of dementia of the Alzheimer type (DAT) in monozygotic twins indicate heritable and sporadic forms of Alzheimer's disease," *Neurology 41*: 1549–1553, Oct. 1991.

Schellenberg et al., "Chromosome I4 and Late–Onset Familial Alzheimer Disease (FAD)," *Am. J. Hum. Genet. 53*: 619–628, 1993.

Schellenberg et al., "Absence of Linkage of Chromosome 21q21 Markers to Familial Alzheimer's Disease," *Science 241*: 1507–1510, Sep. 16, 1988.

Schellenberg et al., "Genetic Linkage Evidence for a Familial Alzheimer's Disease Locus on Chromosome 14," *Science 258*: 668–671, Oct. 23, 1992.

Schellenberg et al., "Genetic Association and Linkage Analysis of the Apolipoprotein CII Locus and Familial Alzheimer's Disease," *Annals of Neurology 31*(2): 223–227, Feb. 1992.

Schellenberg et al., "$APP_{717}$, $APP_{693}$, and PRIP Gene Mutations Are Rare in Alzheimer Disease," *Am. J. Hum. Genet. 49*: 511–517, 1991.

Schellenberg et al., "Linkage Analysis of Familial Alzheimer Disease, Using Chromosome 21 Markers," *Am. J. Hum. Genet. 48*: 563–583, 1991.

Sherrington et al., "Cloning of a gene bearing missense mutations in early–onset familial Alzheimer's disease," *Nature 375*: 754–760, Jun. 29, 1995.

Smith et al., "Protective effect of apoE $\epsilon 2$ in Alzheimer's disease," *The Lancet 344*: 473–474, Aug. 13, 1994.

Strittmatter et al., "Apolipoprotein E: high–avidity binding to $\beta$–amyloid and increased frequency of type 4 allele in late–onset familial Alzheimer disease," *Proc. Natl. Acad. Sci. USA 90*: 1977–1981, Mar. 1993.

Tsai et al., "Apolipoprotein E: Risk Factor for Alzheimer Disease," *Am. J. Hum. Genet. 54*: 643–649, 1994.

Van Bogaeert et al., "Sur les formes familiales précoces de la maladie d'Alzheimer," *Monatsschrift für Psychiatrie und Neurologie 102*(5/6): 249–301, 1940. (English Summary on pp. 299–301).

van Duijn et al., "A Population–based Study of Familial Alzheimer Disease: Linkage to Chromosomes 14, 19, and 21," *Am. J. Hum. Genet. 55*: 714–727, 1994.

Wheelan, Lorna, "Familial Alzheimer's Disease," *Ann. Hum. Genet. 23*: 300–310, 1959.

Yu et al., "The Apolipoprotein E/CI/CII Gene Cluster and Late–Onset Alzheimer Disease," *Am. J. Hum. Genet. 54*: 631–642, 1994.

* cited by examiner

The coding region for AD4 begins a start codon beginning at nucleotide
368 gct(atg)ctc and ends with a stop codon beginning at nucleotide 1712 atc(tga)ggg

```
   1 cgagcggcgg cggagcaggc atttccagca gtgaggagac agccagaagc
  51 aagcttttgg agctgaagga acctgagaca gaagctagtc cccctctga
 101 attttactga tgaagaaact gaggccacag agctaaagtg acttttccca
 151 aggtcgccca gcgaggacgt gggacttctc agacgtcagg agagtgatgt
 201 gagggagctg tgtgaccata gaaagtgacg tgttaaaaac cagcgctgcc
 251 ctctttgaaa gccagggagc atcattcatt tagcctgctg agaagaagaa
 301 accaagtgtc cgggattcag acctctctgc ggccccaagt gttcgtggtg
 351 cttccagagg cagggctatg ctcacattca tggcctctga cagcgaggaa
 401 gaagtgtgtg atgagcggac gtccctaatg tcggccgaga gccccacgcc
 451 gcgctcctgc caggagggca ggcagggccc agaggatgga gagaacactg
 501 cccagtggag aagccaggag aacgaggagg acggtgagga ggaccctgac
 551 cgctatgtct gtagtggggt tcccgggcgg ccgccaggcc tggaggaaga
 601 gctgaccctc aaatacggag cgaagcacgt gatcatgctg tttgtgcctg
 651 tcactctgtg catgatcgtg gtggtagcca ccatcaagtc tgtgcgcttc
 701 tacacagaga agaatggaca gctcatctac acgccattca ctgaggacac
 751 accctcggtg ggccagcgcc tcctcaactc cgtgctgaac accctcatca
 801 tgatcagcgt catcgtggtt atgaccatct tcttggtggt gctctacaag
 851 taccgctgct acaagttcat ccatggctgg ttgatcatgt cttcactgat
 901 gctgctgttc ctcttcacct atatctacct tggggaagtg ctcaagacct
 951 acaatgtggc catggactac cccaccctct tgctgactgt ctggaacttc
1001 ggggcagtgg gcatggtgtg catccactgg aagggccctc tggtgctgca
1051 gcaggcctac ctcatcatga tcagtgcgct catggccccta gtgttcatca
1101 agtacctccc agagtggtcc gcgtgggtca tcctgggcgc catctctgtg
1151 tatgatctcg tggctgtgct gtgtcccaaa gggcctctga gaatgctggt
1201 agaaactgcc caggagagaa atgagcccat attccctgcc ctgatatact
1251 catctgccat ggtgtggacg gttggcatgg cgaagctgga ccccctcctct
1301 cagggtgccc tccagctccc ctacgacccg gagatggaag aagactccta
1351 tgacagtttt ggggagcctt catacccga agtctttgag cctccctga
1401 ctggctaccc aggggaggag ctggaggaag aggaggaaag gggcgtgaag
```

*Fig. 1A*

```
1451 cttggcctcg gggacttcat cctctacagt gtgctggtgg gcaaggcggc
1501 tgccacgggc agcggggact ggaataccac gctggcctgc ttcgtggcca
1551 tcctcattgg cttgtgtctg accctcctgc tgcttgctgt gttcaagaag
1601 gcgctgcccg ccctccccat ctccatcacg ttcgggctca tcttttactt
1651 ctccacggac aacctggtgc ggccgttcat ggacaccctg gcctcccatc
1701 agctctacat ctgagggaca tggtgtgcca caggctgcaa gctgcaggga
1751 attttcattg gatgcagttg tatagtttta cactctagtg ccatatattt
1801 ttaagacttt tctttcctta aaaaataaag tacgtgttta cttggtgagg
1851 aggaggcaga accagctctt tggtgccagc tgtttcatca ccagactttg
1901 gctcccgctt tggggagcgc ctcgcttcac ggacaggaag cacagcaggt
1951 ttatccagat gaactgagaa ggtcagatta gggcggggag aagagcatcc
2001 ggcatgaggg ctgagatgcg caaagagtgt gctcgggagt ggcccctggc
2051 acctgggtgc tctggctgga gaggaaaagc cagttcccta cgaggagtgt
2101 tcccaatgct ttgtccatga tgtccttgtt attttattgc ctttagaaac
2151 tgagtcctgt tcttgttacg gcagtcacac tgctgggaag tggcttaata
2201 gtaatatcaa taaatagatg agtcctgtta gaaaaa
```

*Fig. 1B*

Protein sequence of 448 amino acids that represents the gene product of the Human AD4 gene.

```
  1 MLTFMASDSE EEVCDERTSL MSAESPTPRS CQEGRQGPED GENTAQWRSQ
 51 ENEEDGEEDP DRYVCSGVPG RPPGLEEELT LKYGAKHVIM LFVPVTLCMI
101 VVVATIKSVR FYTEKNGQLI YTPFTEDTPS VGQRLLNSVL NTLIMISVIV
151 VMTIFLVVLY KYRCYKFIHG WLIMSSLMLL FLFTYIYLGE VLKTYNVAMD
201 YPTLLLTVWN FGAVGMVCIH WKGPLVLQQA YLIMISALMA LVFIKYLPEW
251 SAWVILGAIS VYDLVAVLCP KGPLRMLVET AQERNEPIFP ALIYSSAMVW
301 TVGMAKLDPS SQGALQLPYD PEMEEDSYDS FGEPSYPEVF EPPLTGYPGE
351 ELEEEEERGV KLGLGDFIFY SVLVGKAAAT GSGDWNTTLA CFVAILIGLC
401 LTLLLLAVFK KALPALPISI TFGLIFYFST DNLVRPFMDT LASHQLYI
```

*Fig. 2*

Sequence alignment of the Chromosome 1 AD4 gene product with the Chromosome 14 AD3 gene product.

```
AD4   1 MLTFMASDSEEEVCDERTSLMSAESPTPRSCQEGRQGPEDGENTAQWRSQ  50
        | .: |. |   :   :... |   .  | |.||  ...|: .|..:   :||
AD3   1 MTELPAPLSYFQ  NAQMSEDNHLSNTVRSQNDNRERQEHND....RRSL  44

AD4  51 ENEEDGEEDPDRYVCSGVPGRPPGLEEELTLKYGAKHVIMLFVPVTLCMI 100
        :::.|. ..:....  ...|.:....:  :|||||||||||||||||||:
AD3  45 GHPEPLSNGRPQGNSRQVVEQDEEEDEELTLKYGAKHVIMLFVPVTLCMV  94

AD4 101 VVVATIKSVRFYTEKNGQLIYTPFTEDTPSVGQRLLNSVLNTLIMISVIV 150
        |||||||||.||| |:||||||||||||..|||| |:|:||. |||||||
AD3  95 VVVATIKSVSFYTRKDGQLIYTPFTEDTETVGQRALHSILNAAIMISVIV 144

AD4 151 VMTIFLVVLYKYRCYKFIHGWLIMSSLMLLFLFTYIYLGEVLKTYNVAMD 200
        ||||:|||||||||||.||:|||:|||:|||:|.:||||||:|||||||:|
AD3 145 VMTILLVVLYKYRCYKVIHAWLIISSLLLLFFFSFIYLGEVFKTYNVAVD 194

AD4 201 YPTLLLTVWNFGAVGMVCIHWKGPLVLQQAYLIMISALMALVFIKYLPEW 250
        | |: |  :||||.|||::|||||||  |||||||||||||||||||||||
AD3 195 YITVALLIWNFGVVGMISIHWKGPLRLQQAYLIMISALMALVFIKYLPEW 244

AD4 251 SAWVILGAISVYDLVAVLCPKGPLRMLVETAQERNEPIFPALIYSSAMVW 300
        .||:||:.||||||||||||||||||||||||||||||||.:|||||||.|||
AD3 245 TAWLILAVISVYDLVAVLCPKGPLRMLVETAQERNETLFPALIYSSTMVW 294

AD4 301 TVGMAKLDPSSQ..GALQLPYDPEMEE....DSYDSFGEPSYPEVFEPPL 344
        |.||. ||..|  ... .|::|  .|   |. ... ::.:..| :|:..
AD3 295 LVNMAEGDPEAQRRVSKNSKYNAESTERESQDTVAENDDGGFSEEWEAQR 344

AD4 345 TGYPG...........EEL.......EEEEERGVKLGLGDFIFYSVLVG 375
        .:. |            :||         |:.||||||||||||||||||
AD3 345 DSHLGPHRSTPESRAAVQELSSSILAGEDPEERGVKLGLGDFIFYSVLVG 394

AD4 376 KAAATGSGDWNTTLACFVAILIGLCLTLLLLAVFKKALPALPISITFGLI 425
        ||.||:|||||||:|||||||||||||||||||:|||||||||||||||:
AD3 395 KASATASGDWNTTIACFVAILIGLCLTLLLLAIFKKALPALPISITFGLV 444

AD4 426 FYFSTDNLVRPFMDTLASHQLYI 448
        |||.|| ||.|||| ||  ||:||
AD3 445 FYFATDYLVQPFMDQLAFHQFYI 467
```

*Fig. 3*

Sequence features of the Human AD4 gene product

```
  1 MLTFMASDSE EEVCDERTSL MSAESPTPRS CQEGRQGPED GENTAQWRSQ

51 ENEEDGEEDP DRYVCSGVPG RPPGLEEELT LKYGAKHVIM LFVPVTLCMI

101 VVVATIKSVR FYTEKNGQLI YTPFTEDTPS VGQRLLNSVL NTLIMISVIV

151 VMTIFLVVLY KYRCYKFIHG WLIMSSLMLL FLFTYIYLGE VLKTYNVAMD

201 YPTLLLTVWN FGAVGMVCIH WKGPLVLQQA YLIMISALMA LVFIKYLPEW
                            ^^^^
              Conserved tetramer (KGPL 222-225)

251 SAWVILGAIS VYDLVAVLCP KGPLRMLVET AQERNEPIFP ALIYSSAMVW
                         ^^^^
              Conserved tetramer (KGPL 271-274)

301 TVGMAKLDPS SQGALQLPYD PEMEEDSYDS FGEPSYPEVF EPPLTGYPGE

351 ELEEEEERGV KLGLGDFIFY SVLVGKAAAT GSGDWNTTLA CFVAILIGLC
                                                    ^
              Putative N-linked Glycosylation Site (N 386)

401 LTLLLLAVFK KALPALPISI TFGLIFYFST DNLVRPFMDT LASHQLYI
```

*Fig. 5*

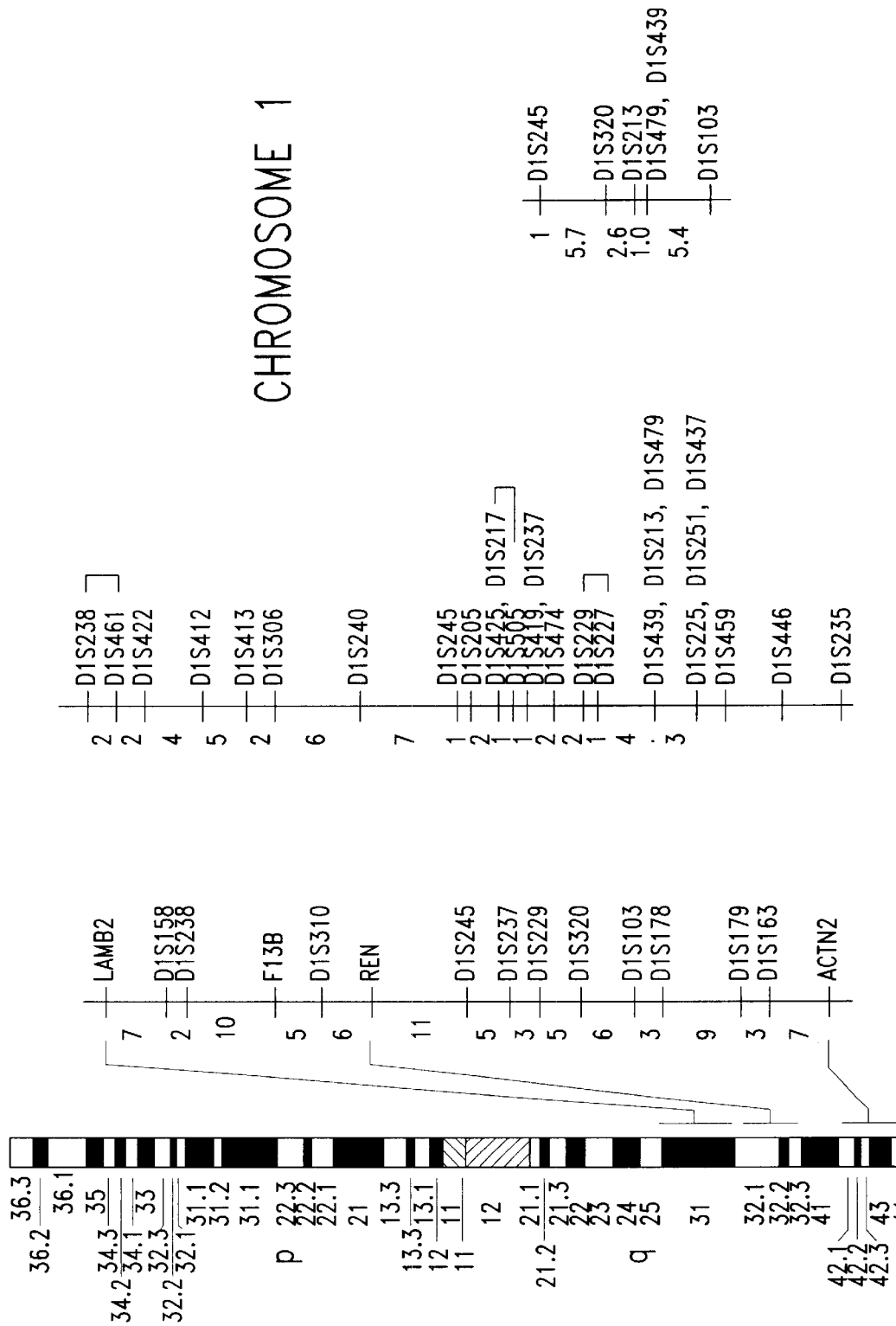

D1S103  ACGAACATTCTACAAGTTAC
        TTTCAGAGAAACTGACCTGT

D1S213  CATTATCCAAGGTCAGGAGG
        AGCTGTTAATCCAATCTATGATGTG d1s225  TGGCCTGAATAGACCATAAAAA
        GCCTGGGTGACAAAGCA

D1S227  AGCTGTGTCGGGTCTTGA
        GAGCGATTTCAGAATGTTGC

D1S229  GCTTGTTTCCATTTATGGTG
        ACTCTAGTTGTGTGTGAATGTATG

D1S320  TTTTGGCACCAGTAATATCTTG
        TTGCAGACTCTGAACTTAGAACA

D1S439  CACAGACTTCATTAGAGGGG
        GTTGAAATGGTGAATTTGGA d1s459  AGCTGGGGTGTTTTATGGAG
        GGGGACCCTGTTTCTGCTAC

D1S479  ACCCATTGCCACCATC
        GGGGAGATTTGGACTGG

*Fig. 9*

DNA SEQUENCES

7881IH5.SEQ

1   AGTGAAATCG TCCTGTGACC ACGCGTCAAG TGCTGATGGG GCACAGCAAC
51  TTCCGGGCCT ATCATATCTC CTTGACCTCG TCCCTCAAAT CTGGTAGTTT
101 CTGCACCGAG GGACACAGTC CACTGCGATG AAGTATGTTC AAAATCGTTT
151 TCTATAGGCA GGTCCTTCCA AAGTCCAATA GTGCAAGGTG GACGCTT

EST T03796

1   GAGAAGGTAA GAGCTGACCC TCAAATACGG AGCGANACGT NATCATGCTG
51  TTTGTGCCTG TCACTCTGTG CATGATCGTG GTGGTAGCCA CCATCAAGTC
101 TGTGCGCTTC TACACAGAGA AGAATGGACA GCTCATCTAC ACGCCATTCA
151 CTGAGGACAC ACCCTCGGTG GGCCAGCGCC TCCTCAACTC CGTGCTGAAC
201 ACCCTCATCA TGATCAGCGT CATCGTGGTT ATGACCATCT TCTTGGTGGT
251 GCTCTACAAG TACCGCTGCT ACAAGTTCAT CCATGGCTGG TTGATCATGT
301 CTTCACTGAT GCTGCTGTTC CTCTTCACCT ATATCTACCT TGGGGAAGTG
351 CTCAAGACCT ACAATGTGGC CATGGACTAC CCCACCCTCT TGCTGACTGT
401 CTGGGAACTT CGGGGCAGTG GGCATGGTGT GCATCCACTG AAGGGGCCTT
451 TGGTGCTGCA GAGGCCTACC TATCA

ELL1.1 DNA Sequence

GGTGGNGCTCTACAAGTACCGCTGCTACAAGGTGAGGCCCTGGCCTGCCCTCCAGCCACCCTTCTCTCCGTC
TGCCCCACACCATGGCGGCAGGGCCGTGAAACAGCCGCCTTTAGAAAAACACAAATTAGAGGAAAATAGACC
CAGATTTTTTGTACTCCTCCCCACCCCATCCTGTCTCCCACCGTGGATGACCTAATACTGTTGTCTTTTATT
TTTATTTATTTTCTTTTTCTTGAAACATGGTCTCACTCCATTGCCCAGGCTGGAGTGCAGTGGTGC

ELL1.2 DNA Sequence

TGCTGATATACTGTATGTTGTCTATATATCATCTAACACCCTCACACTGGAACACAATGCCCGTGGGCAGAG
ACTTTGCTAGCCTTGGTTCCAGAGCCTAGAACAGTGCCTGGCAAGTAGGAGACACCCAGCATTACCTTTCTA
AGTGAACCAGTAGAGATGGGGGGAGACGCAAGCTATGCCGGCAGACCTGAGGGAGTCCTGTCTGCATGCGCT
GCAGGATGACCTGAGGGGAACTCCTTGGACTTCTGTGCCCTCTTTATCTGTAAGGTGGCCACCTGATCCCTT
CCAGCGTAGGCATGAAGTAGCCTAATGAAGAGCATTCAGGCTTGGGTATCAGTCTCAGGATCCTGGGGGCCT
TAGAATTTGTGGCGCTTGGGGACACCTTGTGATCGNGNAATTTCNGTTGTCTAGNNCATCCATGG

*Fig. 10*

PCR PRIMERS

| | |
|---|---|
| WWF | GGA CAC ACC CTC GGT GGG CC |
| WWR | CAA GGT AGA TAT AGG TGA |
| EP1F | CTT GGT GGT GCT CTA CAA GTA C |
| EP1R | GTA GTC CAT GGC CAC ATT GT |
| WWF1L | TCC TCA ACT CCG TGC TGA AC |
| WWR1R | AGC ATC AGT GAA GAC ATG ATC |
| 1.3F | ACC ACC GGG GCA ACC TGA |
| 1.3R | AGG AAG CAG ATC TCA ATA GGA |
| EP2F | GAG AAG GTA AGA GCT GAC CC |
| EP2R | TGA TAG GTA GGC CTC TGC AGC |
| 921D12F | TCC AGC CAC CCT TCT CTC C |
| 921D12R | CAG TAT TAG GTC ATC CAC GGT |
| INT1R | GTG GGG CAG ACG GAG AGA A |
| ADC22L1 | CCC AAG TGT TCG TGG TGC TT |
| ADC22R1 | ACT GTG GAC ATA GCG GTC AGG |
| KM7749 | GGT AGA TAT AGG TGA AGA GG |
| KM7750 | TCA CTG AGG ACA CAC CCT CG |

*Fig. 11*

Genomic sequence of stm.genA ctgcgccctgggggccctgccctgccctccgcacgcctctggccacggtcccttccccgg
ctgtgggtctgcggcccctgcgtgcgcagctcctggcctctgcggccagcgcgggggcgg
agagaggagagtgcccggcaggcggcggctgggccggcccggaactgggtcgtggaaggn
tcgcggggagcggccctcaggccttcggctcactgcgtccccacttccctgcgcccgnct
gccgccgagccccggctgggggtgggcgcggcgcgagcggttaaagggccggtgcattta
aaggagcggtgcacgtgggtctctgaggcgtgtagcaggcgggggcgttttgttcttctt
ctctctcgccggagacctccgttgcgccgagtccattcggcctctagcaccgggtcctgg
gcatgctttccccgggaaggaggcgcgcgggggctctgcccgcacgtgaggggcagggcc
gcaggctcaagcctagagccggtttctgttagcagcggtgtttggctgttttatcaggca
tttccagcagtgaggagacagccagaagcaagcttttggagctgaaggaacctgagacag
aagctagtccccccctctgaattttactgatgaagaaactgaggccacagagctaaagtga
cttttcccaaggtcgcccaggtacgatatagcagagccaggcttcgacccccagtgtcctg
gcttctagatctgctgtccatccctccgagcagacctcacccctgtttattgccttaata
agtattccctttgaaaggtatgaacggtgttgagtgaagtaactgcatccctatttacaa
atggagaacctgagagcattccatagagacgattgtagactaacttaactcagaagcgac
agcctggggttgccaaggctgtctacgaagtaacttgattaggaccgaccccagcttcca
gtaaggaagcctctgatgcctctgtagccaattctgcagacacctgagcctccaaggcct
tcagccaagacctttggcggtaattggagtctcgggataagctgcttcaggtgtgtgagc
ctcaggttcttctctcctgaatgtggttgtgggcagccggtgactggcgcaggtgcagaa
ggggcctggttcttggccccacctcagagctgcgtcctcacgacgcccacgttgagcctt
gggttccagggcagagactggagtgagggcttgggggcatgttgctttgaagtgggatgg
atgtatcaggttttggggaaaactctgtacccttggtgttgaagtcccatgtgcca

*Fig. 13*

Genomic sequence of stm.genB cgggaatggaaacttgatctctggggcctggcctttgaagccagttcatgtgtctggtgg
ttcagcagatccgtaactttccaagaggcacatccataggctaccgtgtcctttctcact
gtgtccctcctccatttcatcttctttataactacgacttattgaacatctactgtgtgc
tggacactttacaggttatctctaggttttacgataatcttgcaaggtatgcctgttctg
cttttacagcagaggaaatgagctgtgtcagattagactgtctgaggcctcttggccag
ggagtatgtggttcaaatcacataggcaggcgatctgaaccctgtcagtctccaaagcct
ctgcttttgaccgctgacttgctgctgcttgtttaaaaataaatgtgtttctggagccta
ctccagaggggcgtgctaggggctccctctcccacttccccacaaaccacccttttccct
ggctgcttcaggaaatgagagaactctgcctgggccccaggcacttctgagtgggacagg
gctgttagaggtaagtctagagcctggcccaaaattcaggaggccccatcagagggcccc
tggggctgtggtccgggagggtggtagggcagtacctcacttccctttgagactcaggcc
ccagctctggcttaggccagggagaaccatccccaagtggtatgtgttactatatgagct
gagatggatggtcagctggaccaaatacatagtcgggtacccagggccaggggggaggaag
gtgagcagggaagctgtgggcaattgtctgggtatcacctgaccttagcaaactcttcct
tgttttaagcgaggacgtgggacttctcagacgtcaggagagtgatgtgagggagctgtg
tgaccatagaaagtgacgtgttaaaaaccagcgctgccctctttgaaagccagggagcat
cattcatttagcctgctgagaagaagaaaccaagtgtccgggattcagacctctctgcgg
ccccaagtgttcgtggtaagtgcagtgactcccaacctgcttttgaaccctcttttcca
ttaggattttctccgtggaggcagatttccatgggagtttgctgtggcattttgaaatct
gtttcttacctagttccattggcctttaaatgttaaggccaaagcctttacatttctctgt
aatgaaaagaaggtcgaggaaattgggtcattgggtttccataatgattgcaggaactgc
tgacacaagcacggctggggagattctctaggtcagactcccttggtttggctaattcag
cagtttgatcccattcagctgattaatgggaatgtgcagtggcttctttggatgtttgat
tttgcatcctaatccaaagcagctatcagcctcagcacttccttgttggaaggcttttcca
gaacgtagtctatgctggacacttccttctgcctctctgcattttcctgccacttctcta
gagaatgggggtgcaggggggtgggagacggggaaagctggtcgctgagtggctgatgggac
ttgacatcacccagccccacccccacctgcccgtgagtcagcctccggggagagttcatc
gcgtcaccggcactctaatgtggacagacacctagcagtgttgtttatctgcacacgttt
gggtggtgattttttccctccaaggatttcagagcaccagcaggcttcagagcagacttag
gtggcttgcaaagcaggccctcaggaattcagagggtagcagaagtccatcccagatgct
ctgttttccttcaggagctaggtaaatcagaggggctgagggacaaatgaaaaaagttac
agcctttgagtcccatctgctcctcctggccaatgagaggggatctgggaggggcagatg
tagaggaaaatctgtctaaatgttgatgctcgttattttcctttaaagaattaatagcct
aaaataaaccctacagataca

*Fig. 14* caccacagatgtttgctgattgaatgaatgagcacactgacagtttggagctgccctgac
tttcgtggctatgcgttttgcccccctgggatgtgagtcacctcaggccagccccaggcaa
ggccgctgctgcctccatggtaactctcaaggcctcttgttttatggcagtcgtttgatt
gacaggcatctcttggaagcttttggggcaggacttgtgtccaagtctccaggtcgcctc
cagccacccctgagtcctccactgcctttgtctcacaggaaagtggaacaaggtccttg
tgctccttttccaggtgcttccagaggcagggctatgctcacattcatggcctctgaca
gcgaggaagaagtgtgtgatgagcggacgtccctaatgtcggccgagagccccacgccgc
gctcctgccaggagggcaggcagggcccagaggatggagagaanactgcccagtgggtag
gtcccaccagcagctgggggccttcaaacaggtcctgcggctactgtaccttacagatga
aaaccagacattcattccctgatgcgggagggagaagggaagtaatgatgaggattggcc
gaaaaggtgggtggctggccatgatggaccttccatctgcagggtttcataggactgcgc
attcacagccagagatggacttggcagtgggctgaagacgctgtccactctgccaccttg
ggtttacctctctcatgcaggtcactgtttccactgtaataggagagtttgtttggatgc
ctgggtgctaggacaggtaacacagaagcttaggatggtagcaggggaagcatttttttgg
cagatggccagacatggtaagtgtgagaggagtctgcctgatacacgattgactttttgag
ctggggatatttgggcttcactgtgatcattcagcccccaggggaggagattgtaacgtt
agaaagagtaggatatcgttgggagagccacttagttgtgtcctttctctcccgatcagg
gcagaacatctgaatttgcctgaaccctgttctctgttttgcccattatagaattaaaaa
atgtctctgtgtggactgtttttttgcagccagtcttaatcctgcttgctgaaatttgag
ctcacttctccatgttctccttgagaacggaaccatcgtccctaagccctgagtgaaatc
acaccagcttaaggccactgctctgccactcctcagccttttcttgtttgttatctccgg
gaagttttgtacactttggttgtttcagtttctgttcatgagtagtcttctttcttggct
gaacgtctagattgggactctctctgcagagaaccggtactgaagcaactgtcattttca
gttttttgtttcatttggcttttttctttagctgttcaccttattagcaaggcagcccatga
ccttgacttgccacagttccaaaacacaaattcttacagatcggtttgtgctagtgtctg
gcaggtgtcctgccctccctcgttacctcctcatttgtgcctgcccaccttcccagagcc
tgcgtcttctcagatgcttaacacctgtttagcctctctagttcagagctacaaatttac
atgcttgattctgtggggcagaaagttcaaagtaatttcttcctctgcaaattcccagta
tcttagtcacacgcaaagagagtgtccctgtgcactgactcctctagctagtgatttgtc
agccaaaaatgtttatttatctcctggcctgtctcctcccatatcagtatggccacatga
acagaattgagtgacctcctgagtccctgtattaggaaggggaaagatctttttgattcat
taaccattaagttgattcattaaccattaagtcttgggcctgcagaccatagcaaccttc
cttccttcatttatggtgcttcatccagctccaaatcttctctactttgtcctcacaaac
ttttcatatgccctagtagctcatagactgctccttatatctggaaagcaacattcaaac
ttctcatttctggttccaaaaatccgtgcattacatggataggctgccntgggggacatt
cngcggccctcacgatgtggtttcccacagagaagccaggagaacgaggaggacggtgag
gaggaccctgaccgctatgtctgtagtgggttcccgggcggccgccaggcctggaggaa
gagctgaccctcaaatacggagcgaagcatgtgatcatgctgtttgtgcctgtcactctg
tgcatgatcgtggtggtagccaccatcaagtctgtgcgcttctacacagagaagaatgga
cagctgtgagttgggggctggggggagcagggtggggtgagggctgagttgccaggggg
tgggggcgcagcagcctgtgttggtcactgtacctgcagctccacaccagcagcggtaa

*Fig. 15A* agagcagggatgaagaaccgcccaggttcatggcctggctcactgcctcctggattgtga
cctacttgggcatgcttttaacatccctatgcctcagcttccttgttcgtataatgggtt
gataacgcagttactgggagaattaagtgagttaatatgagtgaagggcttagaagagtg
tctactgcacgtgagtgctcaggcaagctggatcctgctgcagaaagcaagctcttgatc
ctgggcatggctgtgccactgatccctgtgtgactgcaaacaaatcacttcctctctgag
tctctgcttccctgaatgtgaaacaaggtggttggaccagatatttctcagctcacttcc
agccttgtgaggaagacttataaagcctttcgtttattttagtaaaatacatgcagaggc
agcagcgtagaaaaatgagaagcttcctccacttcttcccccctcccctttctgtggtcct
cactgctaagcaccttctgtaaactttttttttttttttaaagttagggganttttgttt
catttcgtgtgtgttggttttttttgttgttgttgtttcttttaaagaaaggaataaggc
caggtgtggtgtctcatgcctgtaatcccagcactttgggagactgaggtgagaggatta
tttgagcccaggagtttgagaccagcctgggaaatgtggcgagaccctgtctgtacaaaa
aatgcaaaaattagccaggtgtggtggtacatgcctgtagtctcagctacttgggagact
gaggtggaagaacacgtgagcccagaagtcgaggctgcagtgagccatgattgcgccact
gcactgcagcctcagcaacagagtgagaccctgtctcaaaatttttttaa

*Fig. 15B*

Genomic sequence of stm.genD ctgctcatggggatggtgcccgcactccatcagggcagcatgtgggcagcatgggcatcc
caggcacctcccctagcaggtccagaatcactcaaggtggggagcctcgaggagcagtca
gggccgggagcatcagcccttttgccttctccctcagcatctacacgacattcactgagga
cacaccctcggtgggccagcgcctcctcaactccgtgctgaacaccctcatcatgatcag
cgtcatcgtggttatgaccatcttcttggtggtgctctacaagtaccgctgctacaaggt
gaggcccctggccctgccctccagccaccccttctctccgtctgccccacaccatggcggca
gggcccgtgaaacagccgccttttagaaaaacacaaattagaggaaaatagacccagattt
tttgtactcctccccaccccatcctgtctcccaccgtggatgacctaatactgttgtctt
ttatttttatttatttttctttttcttgaaacatggtctcactccattgcccaggctggag
tgcagtggtgcgatcatgactcactgcagcctcaacctcctgggctcaagaagttctccc
acccagcccctcaagtagctaggactacaggtgtgcaccaccatacctggctaattaaaa
aatttttttttgtgcaggctagatctcacagtgttgcccaggctggtctcaaactcctgg
actcaagtgatctcccaccttggcctcccaaagttctgggattacatgtgtgagccattg
catccagcctgttgtctttaaatttacacattatcccacttgagttcctcattgcagtg
ttccaagcatcatttctcatatttcaaagttaattttgttttgcttctctttctgaagtt
ctattttaggctcccctcaccccgatacttccctgaagatttattttagttttcctttt
tccttttcgggcaaggatgtgcagaggccatgctgaggtcttgcagccctgggagacttt
tggggttgtagctgcctatagctgccaagtagccccagggagtagtggaagggcagatccc
atctggccagaatcatgggcactgcctgtccccaaagatgccataagctttagacagcg
gcttcaggcttttctcccaggtaaggggttgaacccctaacgatggaaaggaaattaagc
tgggcattacctattttaaaactgtttacacacaggtgcctcacagcattttttgttcag
gccgctgccatccatggagcaggtagatagaagtgcagagtgcccaggctagagggatgg
gacagggacagtgcagggagggagctgagcccccttccagcgggggcagcagaggggaaa
gccatgggaggggctgcaggatgtgtctgagctgaagcttatcaacaagtaatgagta

*Fig. 16*

Genomic sequence of stm.genE cccctttggctgtgtgtgcagcagggccgtggaggctgcttttagtccaggtagaccag
ggccacgctgaggtcccagtgggctgagctggtgactgatgagttggtcctcaggggtga
ggctggtgggaagtgatgtcactgtcccgccgatggccagctaagggactgggttaggat
cagcccctcttgtccttcactctcccatccttggccaggagaagaggaacaggtctttc
tgaggacctgcttgtagacctttgggtaggaggggacttcccaggttctctgttgaggcc
actctatctaaaatagcaccccagtgagtctcctatcactgtatcctaacattatttct
ccatggccctcatcattacctgctgatatactgtatgtttgtctatatatcatctaacac
ccctcacactggaacacaatgcccgtgggcagagactttgctagccttggttccagagcc
tagaacagtgcctggcaagtaggagacacccagcattacctttctaagtgaaccagtaga
gatgggggggagaccgcaaggctatgccggcagacctgagggagtcctgtctgcatgcgct
gcaggatgacctgaggggaactccttggacttctgtgccctctttatctgtaaggtggcc
acctgatcccttccagcgtaggcatgaagtagcctaatgaagagcattcaggcttgggta
tcagtctcaggatcctgggggccttagaatttgtggcgcttggggacaccttgtgatcgt
gcaatttctgttgtctagttcatccatggctggttgatcatgtcttcactgatgctgctg
ttcctcttcacctatatctaccttgggtaagtgacagataagcagcagggtccctgggag
cccctctccatgtggcacaagtggacatgggcatgaggacctgggcggggaaagatgacc
atcgagctccagtcttccccagtgccagccgttttgggaacccaggcctccgtcgccctc
tctcatggccttgacacaggggagtggaagtggggctgcatggtggaccacatgtttctg
tctcgttcctgatttaaaatgaacccttcatggagaaggctctctgtgaacccccaggggg
atagaaaccccccaaaatttacattctgattttttaggctaggcctgggtactttctggtt
tgtgggaaaaattatctgttctatcgcccccttgatttgggatatcagcctgacccagggg
cccaaagagactgggaggacaagagaaaacactttcccaaggacctttccatgtgcacag
ggtcttccaggtcatgcccatgcacatttctgtgatctgttccaagcatccccaccttgt
tttagaaaatgctgcaaatggtaaattgtaaggacagtgaaggtcggggaaggaaatgtt
agtaaagagggccaggttgggactgaatggtggtaaactgctaggctgtaatgcctccac
tgagtcccagtcacaggctccaccttggtcctgcagggaagtgctcaagacctacaatgt
ggccatggactaccccaccctcttgctgactgtctggaacttcggggcagtgggcatggt
gtgcatccactggaagggccctctggtgctgcagcaggcctacctcatcatgatcagtgc
gctcatggccctagtgttcatcaagtacctcccagagtggtccgcgtgggtcatcctggg
cgccatctctgtgtatggtaggtgggcagcaaggctggtgggggcagtgggggcgatgtc
cagggccaaatcgtccccagtgctgcacaaggagggcaggtgctgaagggcttgcatccc
tttctgcagaggcctgggtgggatccctcctgagagagtcgcctttgtaaaacagaggg
ggtccactatttctggaacactcctggtggtctagataaaacgcagtagtcactgagctc
ctcatttactttttttttttttgagatggagtcttgctctgtcgcccaggctggagtgta
gtggcgccatcttggctgactgcaacctccgcctcccgggttcaagtgattctcctgcct
cagcctcctgagtagataggattataggcatgtgccaccacgctgggctaattttttgtat
ttttagtagagatggggtttcaccatgttggccaggctgatctcgaactcctgaccttgt
gatcggcccgcctcagcctcccaaagtactgggattacaggcatgagccactacacccag
cctcattttccattattactgctatgctgattgagcaagtgcactgttaagcactggaca
cgctgtaagtgatttgttcatcaagacagtccctttgggtaccatgca

*Fig. 17*

Genomic sequence of stm.genF agtccacccgggggctcctgtgctacagggcaggctcttcttcaggggggctgcccgggggat
agtttgacaaggatgtctctgtcttcctagatctcgtggctgtgctgtgtcccaaagggc
ctctgagaatgctggtagaaactgcccaggagagaaatgagcccatattccctgccctga
tatactcatgtgagtgagcccccgtgcctctgcctgactcggggtcagcaggcagcctg
tgggggggacagggggcctgcttcctggccgtggcttttcagagttgactgggcgatcccagg
agggtctccactttcagaagccaggggagggcagtatcttgttattacacagtaagaagct
tagaaagttaggacaggaagcaggcatctgctgggatgtgctgcagtccctgacttcatc
ccgtccatcctccagcggcatgctgcggtgcaggttgcattcctgtgatcccgcagccac
ccctcagctctccaggctcttgagaagggactttggagagggattcttcagggcagggggg
tcgggggagcaaggagcttctgggcttccttgacagcagcgtggctgattggcattaatcc
taactgaagggaaggcacacgggatggcccctggcctcgggggtcaatgtgtagagatttg
gacttacacatgcagtcaacaaaggcacatcaagtccccattttgtgacaggcactgtgc
taggcattggggggacccagcaggaaagaagaccacagggtcccaggcctcatggagctca
cggccctgtgattgtgatgccctcggtctgttgatggcgggggcttaaatagcctgaattt
ctggagctctggcgtctgcaaggtggcctgggaaagagtttatggaacagctacagagtt
ctaggtaccttcatgcagttgaggattcgagcccgtagaggagaattgcctgcagcgtgg
ccccacgggaaagcacattccaggcgcattccgaggatgagcggagaccatgtatggaaa
ggtagtgccaggactgtcatgagtgtcccagggctcgggggggattcacccgtgaacagtga
ggtcttggctctgatagacctggttcttatgctttaggaggggggagacaaacagtaacaga
atagacaaatgcaagagagagtgactctggaccccctcccacaacggcctcctaacaatgg
agcatgagcagatacctgcaggatggagggtcctgtgcaggctttctgggacgcagactg
gccacctcccccaggccctgcaggcagccactgttagcaccgcctgagacgtgaacctt
tctcctcccccagctgccatggtgtggacggttggcatggcgaagctggaccccctcctct
cagggtgccctccagctcccctacgacccggagatgggtgagtatcttggggagctaaca
gcctctcatcactgggggggcagctccctacctgcacccagctctgctcggcctggcttcc
ctgagaggcatgagttcaggagggggcagagggaaaggtccgttgaaaaccagccggacac
atgcggcttgaagattgagcaagtgttggaccctcggtcctctgccagcctctgttgcat
cgttctgctgggcgtgggtgggtggagtgggggggaagccctggtgtcaggtgctggtgctc
agggggggaccccttcttggagctttgttccctggtaacactctgaccagctgttgtttctc
tctcttgttgtcccctcctcacggtgatgacggacatcttctcttcctggacacccagaa
gaagactcctatgacagttttggggagccttcataccccgaagtctttgagcctcccttg
actggctacccaggggaggagctggaggaagaggaggaaagtaaggtgcccatgttcaca
cggcctgcttcagcctacggcgggagcggagacagagggtggaggctccctgcagcctgg
gtggaggagggcatgaggggagggggccccttttcccatcagaggcatctctgtgaaagta
gaagatgcctgcagcgct

Fig. 18

Genomic sequence of stm.genG cagggtctcgctctgttgcccaggctggagtgcagtagcacgattgtggctcactgcaaccttgacttcctgggc
tcaagtgatcctcccaccttggcctcctgagtagctgggattacaggcacgtgctaccacacctggctcatttat
attttagtagagacaaggttttgacttgttgcccgggctggtttcgaactcctgggctcaagtgatccacctgc
cttggccttccaaagtactgggattataggtctgagccacagcacctggccaaaattagttttattataagagat
gcaactcaggaccagccaaatgaagagacagtgaagaagtaatgctgatggatcacacctggtgggggaaggcgg
acagctggggccaggagcaggagggacacctgcagggctggaagggcaggggaggtgggcccccatggtttgtgt
ttattgcataaccattttttattgtctacagtgagcaaagttatcctataaacaagtgtcagggaccattgcacta
aagaaaacaaatgagagcattttggaagctctaatttcctgatcagtaatgggtagactaattcccagttatatt
tacctgttgtaaggtgaaaggttcttcagaggacctctgtcttggtgttatatgggcttttgaatgtactgaaat
taaattccctaaaaanctgtgattcagacttcatactaaattgtacagcagtgcccagcccaaggccttgcattt
ctatttgttgttttctttactctctaagtgcccaacactggttttacctgagtttcagaactgcccgcttttctc
tgcccaggttgtaagtcacccagtccacaggtgtccctgctttcccactggccactgatttggggaggcagctg
tccatgtccccagtccacatcttagcttctagaggcaggtggggtgggctgggctgggcaagagcagctgggcc
ttctgggccagagtttctcttcttttttccattctgtgcacgcctcttcagtacgggttactgtctctcctcacac
agggggcgtgaagcttggcctcggggacttcatcttctacagtgtgctggtgggcaaggcggctgccacgggcag
cggggactggaataccacgctggcctgcttcgtggccatcctcattgtgagtggctggggatgcgtccaactgcc
tcgtggtgggggccccaggtcctcattgtggtgggggcaggtctcaggatccctagggattttttcatttcttc
tcttccctctgagggacaagagcaggggagcgggctggaagggtcagcttgagaccaaggctcacaggaggtgtg
ctcgcccctaggtgggctccagcctgtggaggacagtgcaggggagggtgaggagtgtaccggccccagcgtggc
tgagcacacagcctccaggccgaggacccagctgacagctttgcgcagtgatgatacctcgaggtggttgtgat
gacatcagatttgcagaaaagaaaattgcttaagggccttgcccatgggcgcaaagctagtgaggaccatgtttt
cccctcctccatgccattgggacaccacagggtctgaatctggggcactaggggtggccccgttactgtgaacc
acagcagtgaaatgtggaggccctgtagtcagttaacgtggccagatacacataatggggagacgtcctgccgtg
acttcatctcagagatttcgctgtcacgttagaggaggaggagcgtctgagccgtgcgcttggcatctgcccctt
agtgaaaaccctgggcatggcatgattaaggttgatgctccagtgtccagaaggttttcttttgcccacaagta
tatcagggatgggatggtggacccaggctcctccaccaccagactgccttacctgagccctgctggccccaaaga
tatagaaggcaccctggttccctgtgctcacctggaccactgcctgcatcagctgggtcaggggaggatgggcag
cccccacacctgcttcccaggggcaggttgcctggcggtctgattcccttggtgccagctgctgagaaccttac
tgccatttcagttgagcccacctagctctcatataaatacatgttccctgagggcatcttaccatcccatgtgac
cactccagccagacaggggaggcagcacggcctcggggcacagcactgctccaggagtcaggaggcctgccttct
ggttcactcactaacaggtgaggtgatctaatggggtgagaacttctgaccttaacacctcaagagctgttgca
ggaccagggaagataatggggtgtctagcgccgttatccgactggtcctcgaacaagctcctgtgcccagggact
agaccatgactcacagctcctgtccacaccagggatcaccacgctcaccctcccctccatgtcctgcagggcttg
tgtctgaccctcctgctgcttgctgtgttcaagaaggcgctgcccgccctcccatctccatcacgttcgggctc
atcttttacttctccacggacaaccctggtgcggccgttcatggacaccctggcctcccatcagctctacatctga
gggacatggtgtgccacaggctgcaagctgcagggaattttcattggatgcagttgtatagttttacactctagt
gccatatattttaagacttttcttttccttaaaaaataaagtacgtgtttacttggtgaggaggaggcagaacca
gctctttggtgccagctgtttcatcaccagactttggctcccgctttggggagcgcctcgcttcacggacaggaa
gcacagcaggtttatccagatgaactgagaaggtcagattagggcggggagaagagcatccggcatgagggctga

Fig. 19A gatgcgcaaagagtgtgctcgggagtggcccctggcacctgggtgctctggctggagaggaaaagccagttccct
acgaggagtgttcccaatgctttgtccatgatgtccttgttattttattgcctttagaaactgagtcctgttctt
gttacggcagtcacactgctgggaagtggcttaatagtaatatcaataaatagatgagtcctgttagaatcttgg
agtttggtccgttgtaaatgttgaccccctctccctgcatcttgggcacccctgggataacttgtgctgtgagccc
aggatggaggcagtttgccctgtttgaaggaacttttaatgatctcgcctctctgcacacatttctttaactaga
aagtttcctaagcaaaggagttaggagagcagggtggcctgacatctgccagccctgagctgtaaggctgtggat
gctgagcaggtccctggactcagttgtgcacggtggcacagacactgccaggtggttgccaaaacatccagtggt
tccttcagcaagtgttcaccctctgcagaagcctgtgagggcctgagctcagaaaccactctcctttccttctct
ggctttggccctgggcactgtggtgggagagtggacagtttggctttgccttctctgtacatcaatcatgggttg
caaagagaatctcagaagtgcctcttcctgagcacagtggctcacacctgtaatcccaatacttcgggaggtcga
gtcggaaggatcacttgagcccaggagtttgagaccagccggggcaacatagtgagactttgtacaaaaaaaaat
ttaaaaattagccaagcatggtggcatgcatctgtagtctcagctactctggaggctgaggtgggaggatcactt
aagcccaggaggctgaggctgcaatgagccgagatcaagcaggtgttaggtatatcagacagctgagaagacgca
agtgtgccctggggttcaaactggtacccctgtctccctgttccaggaataacatgagtgccgggacaatgcatc
tttattatgagaggaatgagaattgt

*Fig. 19B*

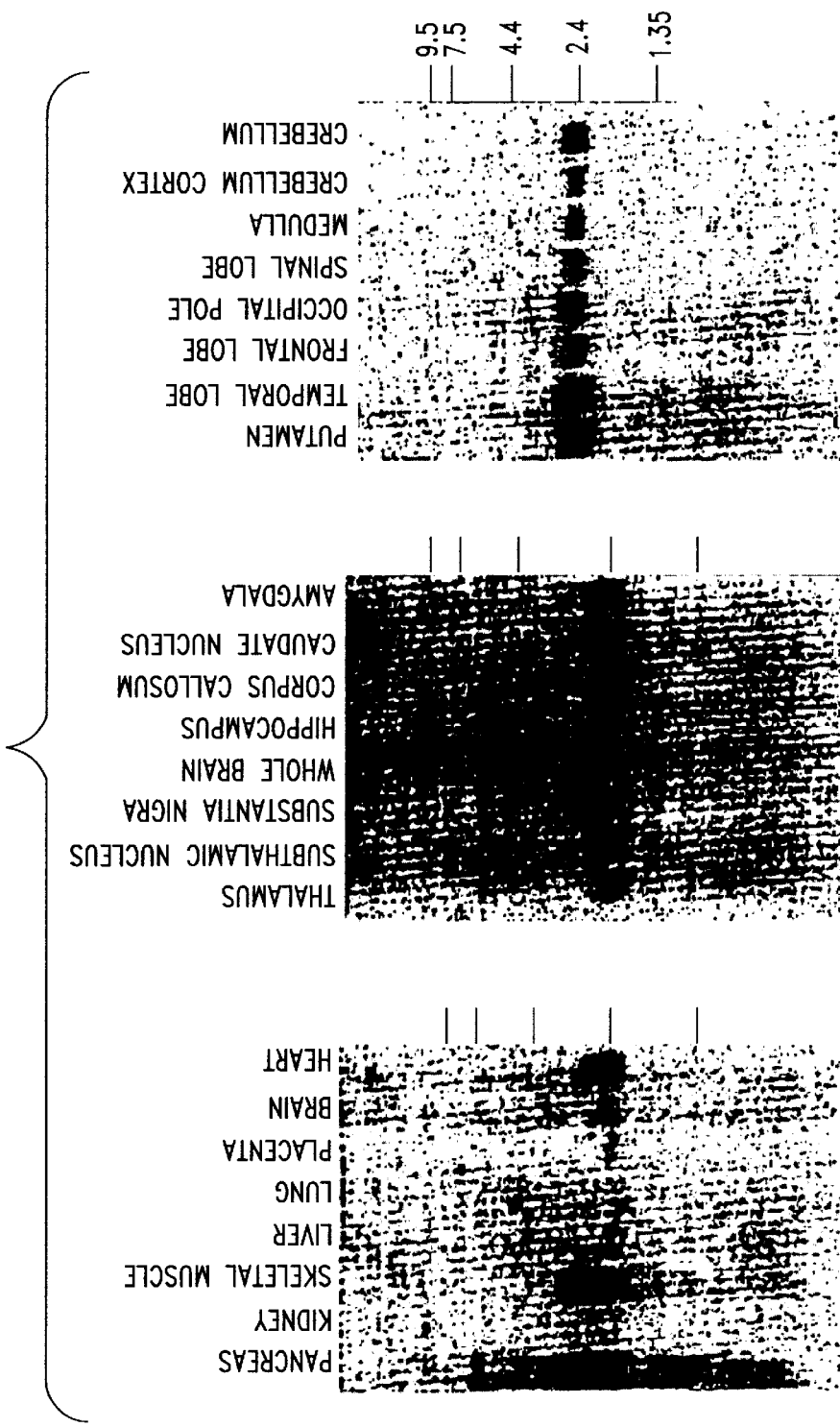
Fig. 20 GENE STRUCTURE AND EXPRESSION OF STM2

CHROMOSONE 1 GENE AND GENE PRODUCTS RELATED TO ALZHEIMER'S DISEASE

CROSS-REFERENCE TO RELATED APPLICATION

This application is a continuation of U.S. patent application No. 08/675,876, filed Jul. 5, 1996, now abandoned, which claims the benefit of U.S. Provisional Application No. 60/002,328 filed Aug. 14, 1995; U.S. Provisional Application No. 60/002,174 filed Aug. 11, 1995; U.S. Provisional Application No. 60/001,675 filed Jul. 28, 1995; and U.S. Provisional Application No. 60/000,956 filed Jul. 7, 1995.

TECHNICAL FIELD

The present invention relates generally to Alzheimer's disease, and more specifically to methods and compositions for use in diagnosis and treatment of Alzheimer's Disease.

BACKGROUND OF THE INVENTION

Alzheimer's disease (AD) is a devastating, neurodegenerative progressive disorder first recognized in 1907 (Alzheimer, *Algemeine Zeitschrift fur Psychiatrie* 64:146–148, 1907). AD is a common disease in the elderly and is the predominant cause of dementia in people over 65 years of age. The prevalence of AD is estimated to be as high as 18.7% and 47.2% for the 75–84 year and ≧85 year age groups respectively. Thus, there is a large affected population in most countries of the world.

Clinical symptoms of the disease typically begin with subtle short term memory problems. As the disease progresses, difficulty with memory, language, and orientation worsen to the point of interfering with the ability of the person to function independently. Other symptoms, which are variable, include myoclonus and seizures. Duration of AD from the first symptoms of memory loss until death is 10 years on average, but may range from 6–8 years to more than 20 years. AD always results in death, often from respiratory-related illness.

The pathology in AD is confined exclusively to the central nervous system (CNS). The predominant features are amyloid deposits (plaques) and neurofibrillary tangles (NFT). In AD, amyloid is found associated with the vascular system of the CNS and as focal deposits in the parenchyma. The major molecular component of amyloid is a highly hydrophobic peptide called the Aβ peptide. This peptide aggregates into filaments in an anti-β-pleated sheet structure resulting in the birefringent nature of the AD amyloid. While Aβ is the major component of AD amyloid, a partial list of other proteins associated with the amyloid includes α-1-antichymotrypsin (Abraham, et al., *Cell* 52:487–501, 1988), cathepsin D (Cataldo, et al., *Brain Res.* 513:181–192, 1990), non-amyloid component protein (Ueda, et al., *Proc. Natl Acad. Sci. USA* 90:11282–11286, 1993), apolipoprotein E (apoE) (Namba, et al., *Brain Res.* 541:163–166, 1991; Wisniewski and Frangione, *Neurosci. Lett.* 135:235–238, 1992; Strittmatter, et al., *Proc. Nat. Acad. Sci. USA* 90:1977–1981, 1993), apolioprotein J (Choi-Mura, et al., *Acta Neuropathol.* 83:260–264, 1992; McGeer, et al., *Brain Res.* 579:337–341, 1992), heat shock protein 70 (Hamos, et al., *Neurology* 41:345–350, 1991), complement components (McGeer and Rogers, *Neurology* 43:447–449, 1992), α$_2$-macroglobin (Strauss, et al., *Lab. Invest.* 66:223–230, 1992), interleukin-6 (Strauss, et al., *Lab. Invest.* 66:223–230, 1992), proteoglycans (Snow, et al., *Lab. Invest.* 58:454–458, 1987), and serum amyloid P (Coria, et al., *Lab. Invest.* 58:454–458, 1988). Surrounding many plaques are dystrophic neurites, which are nerve endings containing abnormal filamentous structures. Plaques are often surrounded by astrocytes and activated microglial cells expressing immune-related proteins, such as the MHC class II glycoproteins HLA-DR, HLA-DP, and HLA-DQ as well as MHC class I glycoproteins, interleukin-2 (IL-2) receptors, and IL-1. The other dominant feature of AD neuropathology is the presence of NFTs. These consist of abnormal filaments bundled together in neuronal cell bodies. "Ghost" NFTs are also observed in AD brains, which presumably mark the location of dead neurons. Other neuropathological features include granulovacuolar changes, neuronal loss, gliosis and the variable presence of Lewy bodies.

In the AD brain, the destructive process of the disease is evident on a gross level. In the late-stage of AD, ventricular enlargement and shrinkage of the brain can be observed by magnetic resonance imaging. On autopsy, extensive gliosis and neuronal loss are observed. Thus, the amyloid plaque structures and NFTs observed at autopsy are most likely the end-points of a lengthy disease process, far removed from the initiating events of AD. Also, the cells remaining at autopsy are grossly different from those of a normal brain. Neurons, which were possibly involved in initiating events, are absent and other cell types, such as the activated microglial cells and astroctyes, have gene expression patterns not observed in the normal brain. Thus, attempts using biochemical methods to identify key proteins and genes in the initiating steps of the disease are hampered by the fact that it is not possible to actually observe these critical initiating events. Rather, biochemical dissection of the AD brain at autopsy is akin to molecular archeology, attempting to reconstruct the pathogenic pathway by comparing the normal brain to the end-stage disease brain.

Substantial evidence has suggested that inherited genetic defects are involved in AD. Numerous early-onset kindreds have been described (Bird, et al., *Ann. Neurol.* 23:25–31, 1988; Bird, et al., *Ann. Neurol.* 25:12–25, 1989; Cook, et al., *Neurology* 29:1402–1412, 1979; Feldman, et al., *Neurology* 13:811–824, 1960; Goudsmit, *J. Neuro.l Sci.* 49:79-, 1981; Heston and White, *Behavior Genet.* 8:315–331, 1978; Martin, et al., *Neurology* 41:62–68, 1991; Nee, et al., *Arch. Neurol.* 40:203–208, 1983; van Bogaeert, et al., *Mschr. Psychait. Neurol.* 102:249–301, 1940; Wheelan, *Ann. Hum. Genet.* 23:300–309, 1959). (Early-onset is defined herein as onset prior to 65 years.) Families with multiple late-onset AD cases have also been described (Bird, et al., *Ann. Neurol.* 25:12–25, 1989; Heston and White, *Behavior Genet.* 8:315–331, 1978; Pericak-Vance, et al., *Exp. Neurol.* 102:271–279, 1988). In addition, twin studies have documented that monozygotic twins are more concordant in their AD phenotype than dizygotic twins (Nee, et al., *Neurology* 37:359–363, 1987; [133]). Also, the families of concordant twins have more secondary cases of AD than families of discordant twins (Rapoport, et al., *Neurology* 41:1549–1553, 1991).

Genetic dissection of AD has been complicated by the complexity of the disease and the limited accuracy of its diagnosis. Because AD is common in the elderly, clustering of cases in a family may occur by chance, representing possible confounding non-allelic genetic heterogeneity, or etiologic heterogeneity with genetic and non-genetic cases co-existing in the same kindred. In addition, the clinical diagnosis of AD is confounded with other dementing diseases common in the elderly.

Despite the problems associated with resolving complex genetic diseases, 2 causative AD loci and 1 risk-modifying gene have been identified. Mutations in the amyloid precursor protein (APP) gene on chromosome 21 cause early-onset (<65 years) autosomal dominant AD (Goate, et al., *Nature* 349:704, 1991). Mutations in a recently identified gene (AD3) on chromosome 14 also result in early-onset autosomal dominant AD (Schellenberg, et al., *Science* 258:668, 1992; Sherrington, et al., *Nature* 375:754–760, 1995). For late-onset AD, the APOE gene has been identified as a genetic modifying factor (Strittmatter, et al., *Proc. Natl. Acad. Sci. USA* 90:1977, 1993; Corder, et al., *Science* 261:921, 1993; Corder, et al., *Nat. Genet.* 7:180–184, 1994; Benjamin, et al., *Lancet* 344:473, 1994; Smith, et al., *Lancet* 344:473–474, 1994).

The known genetic loci for AD do not account for all cases of AD. For example, in late-onset AD approximately half of AD cases do not have the APOE ε4 allele (Brousseau, et al., *Neurology* 342, 1994; Kuusisto, et al., *Brit. Med J.* 309:636, 1994; Tsai, et al., *Am. J. Hum. Genet.* 54: 643, 1994; Liddel, et al., *J Med. Genet.* 31:197, 1994). Also, in the Volga German (VG) kindreds (Cook, et al., *Neurology* 29:1402, 1979; Bird, et al., *Ann. Neurol.* 23:25, 1988; Bird, et al., *Ann. Neurol.* 25:12, 1989; Bird, *Am. Hist. Soc. Germ. Russia J.* 49:1991; Bird, et al., in *Heterogeneity of Alzheimer's Disease*, F. Boller, et al., Eds. (Spring-Verlag, Heidelberg, 1992) pp. 118–129), as in several other families with high incidence of AD, the known AD loci have been excluded as possible causes (Schellenberg, et al., *Science* 258:668, 1992; Lannfelt, et al., *Nat. Genet.* 4:218–219, 1993; van Duijn, et al., *Am. J. Hum. Genet.* 55:714–727, 1994; Schellenberg, et al., *Science* 241:1507, 1988; Schellenberg, et al., *Am. J. Hum. Genet.* 48:563, 1991; Schellenberg, et al., *Am. J. Hum. Genet.* 49:511–517, 1991; Kamino, et al., *Am. J. Hum. Genet.* 51:998, 1992; Schellenberg, et al., *Am J. Hum. Genet.* 53:619, 1993; [13]; Schellenberg, et al., *Ann. Neurol.* 31:223, 1992; Yu, et al., *Am. J. Hum. Genet.* 54:631, 1994). Identification of new genes should add considerably to the unfolding of the genetic determinants and enable biochemical and genetic approaches to diagnosis and treatment.

The present invention provides a novel, previously unidentified locus for AD, methods and compositions for diagnosis and treatment of AD, and further provides other, related advantages.

SUMMARY OF THE INVENTION

Briefly stated, the present invention provides isolated nucleic acid molecules encoding an AD4 (also known as STM2) gene product. Within one embodiment, a representative nucleic acid molecule is provided in FIGS. 1A and B (hereinafter referred to as FIG. 1). SEQ ID NO:1 Within other embodiments, nucleic acid molecules are provided which encode a mutant AD4 gene product that increases the probability of Alzheimer's Disease (in a statistically significant manner). One representative illustration of such a mutant is an amino acid subsitution at residue 141, wherein, for example, an isoleucine may be substituted for an aspargine.

Within other aspects of the present invention, isolated nucleic acid molecules are provided, selected from the group consisting of (a) an isolated nucleic acid molecule as set forth in FIG. 1 (SEQ ID NO:1) or complementary sequence thereof, (b) an isolated nucleic acid molecule that specifically hybridizes to the nucleic acid molecule of (a) under conditions of high stringency, and (c) an isolated nucleic acid that encodes an AD4 gene product. As utilized herein, it should be understood that a nucleic acid molecule hybridizes "specifically" to an AD4 gene (or related sequence) if it hybridizes detectably to such a sequence, but does not significantly or detectably hybridize to the AD3 gene sequence under the same conditions. Within other aspects, isolated DNA molecules are provided that contain genomic sequences, such as the sequences presented in FIGS. 13–19. (SEQ ID NOS:34–40)

Within other aspects, expression vectors are provided comprising a promoter operably linked to one of the nucleic acid molecule described above. Representative examples of suitable promoters include tissue-specific promoters, as well as promoters such as the CMV I-E promoter, SV40 early promoter and MuLV LTR. Within related aspects, viral vectors are provided that are capable of directing the expression of a nucleic acid molecule as described above. Representative examples of such viral vectors include herpes simplex viral vectors, adenoviral vectors, adenovirus-associated viral vectors and retroviral vectors. Also provided are host cells (e.g., human, dog, monkey, rat or mouse cells) which carry the above-described vectors.

Within other aspects of the present invention, isolated proteins or polypeptides are provided comprising an AD4 gene product, as well as AD4 peptides of greater than 12, 13, or 20 amino acids. Within one embodiment, a protein is provided that has the amino acid sequence set forth in FIG. 2. (SEQ ID NO:2) Within another embodiment, the protein is a mutant AD4 gene product that increases the probability of Alzheimer's Disease. Such mutants include those with an amino acid subsitution at residue 141 (e.g., an aspargine to isoleucine substitution). Within yet a further embodiment, AD4 peptides are provided which are composed of 13 to 20 amino acids derived or selected from the N-terminal, internal, or carboxy-terminal hydrophilic regions.

Within yet another aspect of the present invention, methods of treating or preventing Alzheimer's Disease are provided, comprising the step of administering to a patient a vector containing or expressing a nucleic acid molecule as described above, thereby reducing the likelihood or delaying the onset of Alzheimer's Disease in the patient. Within a related aspect, methods of treating or preventing Alzheimer's Disease are provided, comprising the step of administering to a patient a protein as described above, thereby reducing the likelihood or delaying the onset of Alzheimer's Disease in the patient. Within yet another related aspect, methods are provided for treating or preventing Alzheimer's Disease comprising the step of administering to a patient an antibody specific for an AD4 protein as described above, thereby reducing the likelihood or delaying the onset of Alzheimer's Disease in the patient. Within certain embodiments, the above methods may be accomplished by in vivo administration.

Also provided by the present invention are pharmaceutical compositions comprising a nucleic acid molecule, vector, host cell, protein, or antibody as described above, along with a pharmaceutically acceptable carrier or diluent.

Within other aspects of the present invention, antibodies are provided which specifically bind to an AD4 protein, or to unique peptides derived from the N-terminal, internal, or carboxy-terminal hydrophilic regions. As utilized herein, it should be understood that an antibody is specific for an AD4 protein if it binds detectably, and with a $K_A$ of $10^{-7}M$ or less (e.g., $10^{-8}M$, $10^{-9}M$, etc.), but does not bind detectably (or with an affinity of greater than $10^{-7}M$, (e.g., $10^6M$, $10^5M$, etc.) to the AD3 protein. Also provided are hybridomas which are capable of producing such antibodies.

Within other aspects of the present invention, nucleic acid probes are provided which are capable of specifically hybridizing (as defined above) to an AD4 gene under conditions of high stringency. Within one related aspect, such probes comprise at least a portion of the nucleotide sequence shown in FIG. 1 or its complementary sequence, the probe being capable of specifically hybridizing to a mutant AD4 gene under conditions of high stringency. Within one particularly preferred aspect, probes are provided that are capable of specifically hybridizing to a mutant AD4 gene in which amino acid residue 141 is changed from asparagine to isoleucine, under conditions of very high stringency. Within other related aspects, probe are provided which are capable of specifically hybridizing to at least a portion of the nucleic sequence shown in any of FIGS. 13–19. (SEQ ID NOS:34–40) Representative probes of the present invention are generally at least 12 nucleotide bases in length, although they may be 14, 16, 18 bases or longer. Also provided are primer pairs capable of specifically amplifying all or a portion of any of the nucleic acid molecules disclosed herein.

Within other aspects of the invention, methods are provided for diagnosing a patient having an increased likelihood of contracting Alzheimer's Disease, comprising the steps of (a) obtaining from a patient a biological sample containing nucleic acid; (b) incubating the nucleic acid with a probe which is capable of specifically hybridizing to a mutant AD4 gene under conditions and for time sufficient to allow hybridization to occur, and (c) detecting the presence of hybridized probe, and thereby determining that said patient has an increased likelihood of contracting Alzheimer's Disease. Within another aspect, methods are provided comprising the steps of (a) obtaining from a patient a biological sample containing nucleic acid, (b) amplifying a selected nucleic acid sequence associated with a mutant AD4 gene, and (c) detecting the presence of an amplified nucleic acid sequence, and thereby determining that the patient has an increased likelihood of contracting Alzheimer's Disease. Within yet another aspect, methods are provided comprising the steps of (a) contacting a biological sample obtained from a patient with an antibody that specifically binds to a mutant AD4 protein, under conditions and for a time sufficient to allow binding of the antibody to the protein, and (b) detecting the presence of the bound antibody. Suitable biological samples include nucleated cells obtained from the peripheral blood, from buccal swabs, or brain tissue.

Within another aspect, peptide vaccines are provided which comprise a portion of a mutant AD4 gene product containing a mutation, in combination with a pharmaceutically acceptable carrier or diluent.

Within yet another aspect, transgenic animals are provided whose germ cells and somatic cells contain an AD4 gene which is operably linked to a promoter effective for the expression of the gene, the gene being introduced into the animal, or an ancestor of the animal, at an embryonic stage. Within one embodiment, the animal is a mouse, rat or dog. Within other embodiments, the AD4 gene is expressed from a vector as described above. Within yet another embodiment, the AD4 gene encodes a mutant AD4 gene product.

These and other aspects of the present invention will become evident upon reference to the following detailed description and attached drawings. In addition, various references are set forth herein which describe in more detail certain procedures or compositions (e.g., plasmids, etc.), and are therefore incorporated by reference in their entirety.

BRIEF DESCRIPTION OF THE DRAWINGS

FIGS. 1A and 1B depict the nucleotide sequence of an AD4 gene. (SEQ ID NO:1)

FIG. 2 depicts the amino acid sequence of an AD4 gene product. (SEQ ID NO:2)

FIG. 3 depicts the sequence alignment of a representative AD4 gene product (SEQ ID NO:2) to the AD3 gene product. (SEQ ID NO:3) Vertical bars between the sequences indicate sequence identity. Colons between the sequences indicate strong sequence similarity. Dots between the sequences indicate medium sequence similarity. Dots inserted into either sequence indicate gaps inserted into a sequence so as to maximize the score of the alignment.

FIG. 5 depicts certain sequence features of a representative AD4 gene product, (SEQ ID NO:2) including a conserved sequence of 4 amino acids (KPGL) in positions 202–205 and 251–254, each of which lie at the C-terminus of a putative membrane spanning regions and are conserved in the human and mouse AD3 gene products. FIG. 5 also depicts a putative glycosylation site (asparagine 366).

FIG. 8 depicts the location of chromosome 1 markers. Distances are given in centimorgans (sex-averaged) with the use of the Kosambi map function. The 3 maps are not independent as all contain some common genotypes.

FIG. 9 sets forth the sequences of primers (SEQ ID NO.4) used to amplify polymorphic regions of chromosome 1.

FIG. 10 presents the DNA sequence of clone 788iih5, (SEQ ID NO:13) EST TO3796 (SEQ ID NO:14) and clones Ell1.1 (SEQ ID NO:15) and ELL1.2. (SEQ ID NO:16)

FIG. 11 presents the DNA sequences of primers (SEQ ID NOS:17 to 33) used in PCR or sequencing of the AD4 gene sequence.

Figure 4:
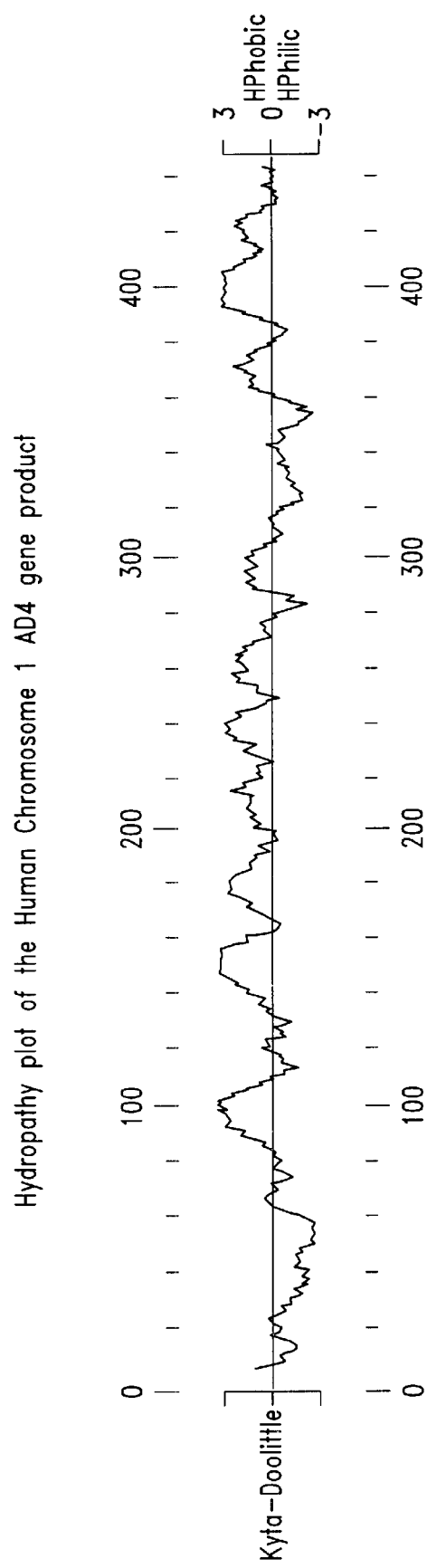
FIG. 4 depicts a hydropathy plot of an AD4 gene product. The plot indicates that there are 7 putative transmembrane regions of this gene product, and indicates a mutation at residue 141 (asparagine to isoleucine).
Figure 6:
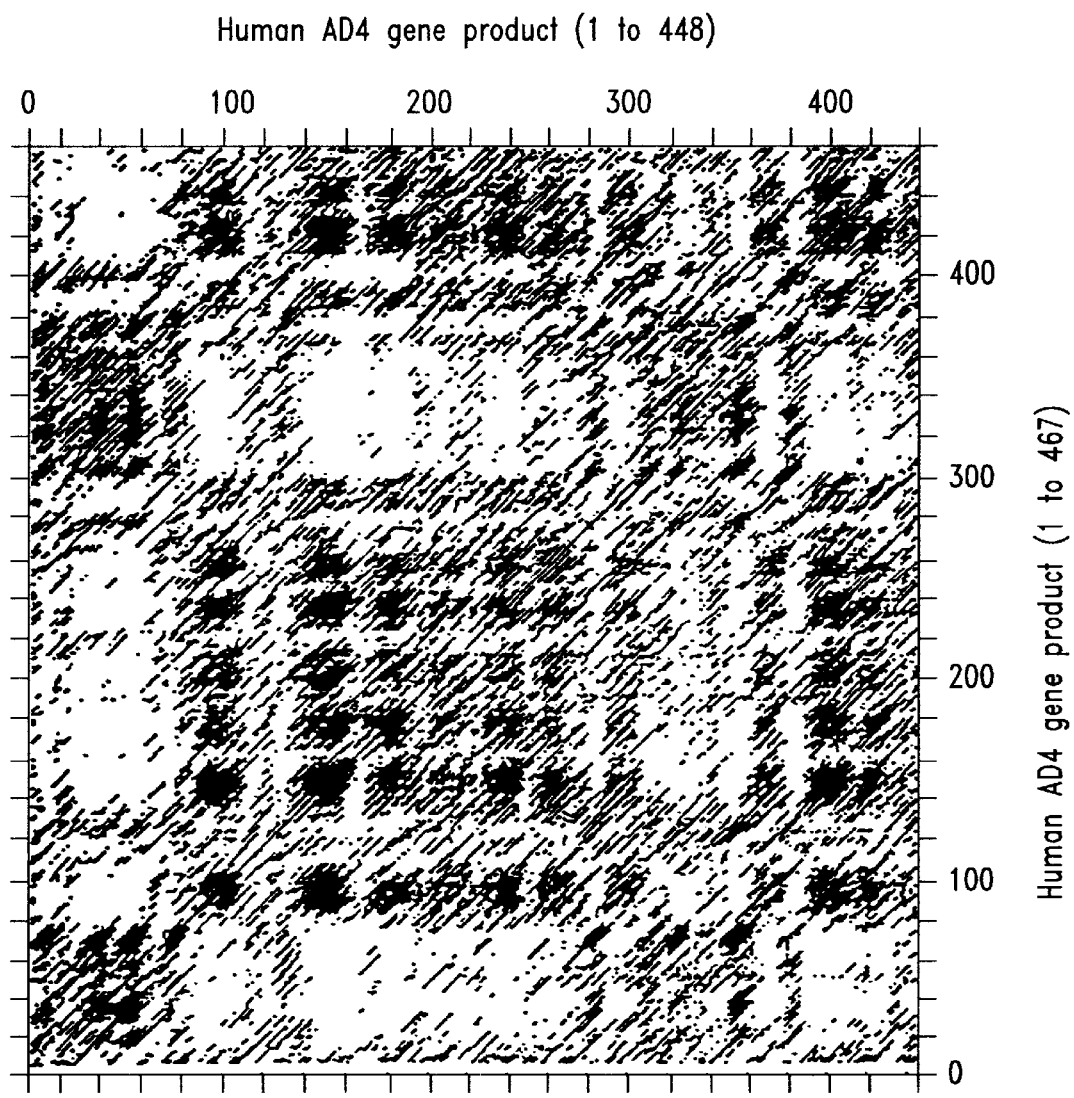
FIG. 6 is a dotplot which compares the human AD3 gene product and a representative AD4 gene product. The dark blocks indicate sequence similarity between the putative membrane spanning regions.

6, affected, onset at 52 years; 7, affected, onset 46 years; 8, affected, onset 49 years.

FIG. 13 presents a partial genomic DNA sequence of AD4. (SEQ ID NO:34)

FIG. 14 presents a partial genomic DNA sequence of AD4. (SEQ ID NO:35)

FIG. 15 presents a partial genomic DNA sequence of AD4. (SEQ ID NO:36)

FIG. 16 presents a partial genomic DNA sequence of AD4. (SEQ ID NO:37)

FIG. 17 presents a partial genomic DNA sequence of AD4. (SEQ ID NO:38)

FIG. 18 presents a partial genomic DNA sequence of AD4. (SEQ ID NO:39)

FIG. 19 presents a partial genomic DNA sequence of AD4. (SEQ ID NO:40)

FIG. 20 shows expression pattern of STM2 in different tissues.

DETAILED DESCRIPTION OF THE INVENTION

DEFINITIONS

Prior to setting forth the invention in detail, it may be helpful to an understanding thereof to set forth definitions of certain terms and to list and to define the abbreviations that will be used hereinafter.

"Genetic marker" is any segment of a chromosome that is distinguishably unique in the genome, and polymorphic in the population so as to provide information about the inheritance of linked DNA sequences, genes and/or other markers.

"Autosomal dominant" means that a trait is encoded on one of the non-sex chromosomes (autosomes) and is dominant for the phenotype it dictates for an individual having a heterozygous state.

"LOD score" is a standard measure in genetics of the likelihood of a trait being localized in the interval being scored. Is the logarithm of a calculated probability.

"Vector" refers to an assembly which is capable of directing the expression of an AD4 gene, as well as any additional sequence(s) or gene(s) of interest. The vector must include transcriptional promoter elements which are operably linked to the genes of interest. The vector may be composed of either deoxyribonucleic acids ("DNA"), ribonucleic acids ("RNA"), or a combination of the two (e.g., a DNA-RNA chimeric). Optionally, the vector may include a polyadenylation sequence, one or more restriction sites, as well as one or more selectable markers such as neomycin phosphotransferase or hygromycin phosphotransferase. Additionally, depending on the host cell chosen and the vector employed, other genetic elements such as an origin of replication, additional nucleic acid restriction sites, enhancers, sequences conferring inducibility of transcription, and selectable markers, may also be incorporated into the vectors described herein.

Abbreviations: AD, Alzheimer's disease; APP, amyloid precursor protein gene; APLP1 and APLP2, amyloid precursor like proteins; CNS, central nervous system; DS, Down syndrome; FAD, familial AD; HCHWA-D, hereditary cerebral hemorrhage with amyloidosis—Dutch type; ($Z_{max}$), maximum LOD score; NFT's, neurofibrillary tangles; STRP, short tandem repeat polymorphism; Θ, recombination fraction; VG, Volga German; AD3, the designation given to the chromosome 14 early-onset FAD gene; YAC, yeast artificial chromosome; EST, espressed sequence tag; PCR, polymerase chain reaction; RT-PCR, PCR process in which RNA is first transcribed into DNA at the first step using reverse transcriptase (RT); cDNA, any DNA made by copying an RNA sequence into DNA form.

As noted above, the present invention provides methods and compositions for the detection and treatment of Alzheimer's Disease. These methods and compositions are based upon the discovery of a gene which is located on chromosome 1, which when mutated increases the probability of Alzheimer's Disease. This gene, designated AD4, was found to be located on chromosome 1 at locus 1q31-42.

Although one embodiment of an AD4 gene is disclosed in FIG. 1, (SEQ ID NO:1)it should be understood that the present invention is not so limited. In particular, within the context of the present invention reference to the AD4 gene should be understood to include derivatives, analogs, or allelic variants of the gene disclosed in FIG. 1 that are substantially similar. As used herein, a nucleic acid molecule is deemed to be "substantially similar" if: (a) the nucleotide sequence is derived from the coding region of the described gene and includes portions of the sequence or allelic variations of the sequences discussed above; (b) the nucleotide sequence is capable of hybridization to nucleotide sequences of the present invention under high or very high stringency (see Sambrook et al., *Molecular Cloning: A Laboratory Manual*, 2nd ed., Cold Spring Harbor Laboratory Press, NY, 1989); or (c) the DNA sequences are degenerate as a result of the genetic code to the DNA sequences defined in (a) or (b). In addition, the genomic sequence may contain only polymorphisms, either in the coding or non-translated region, or insertions, deletions and the like. Further, the AD4 gene includes both complementary and non-complementary sequences, provided the sequences otherwise meet the criteria set forth herein. Within the context of the present invention, high stringency means standard hybridization conditions (e.g., 5×SSPE, 0.5% SDS at 65° C., or the equivalent), such that an appropriate nucleotide sequence is able to selectively hybridize to nucleotide sequences from the AD-related gene, and to mutant nucleotide sequences. Very high stringency means the nucleotide sequence is able to selectively hybridize to a single allele of the AD-related gene.

The AD4 gene may be isolated from genomic DNA or cDNA. Genomic DNA libraries constructed in vectors, such as YACs (yeast artificial chromosomes), bacteriophage vectors, such as λEMBL3, λgt10, cosmids or plasmids, are suitable for use. cDNA libraries constructed in bacteriophage vectors, plasmids, or others, are suitable for screening. Such libraries may be constructed using methods and techniques known in the art (see Sambrook et al., *Molecular Cloning: A Laboratory Manual*, Cold Spring Harbor Press, 1989) or purchased from commercial sources (e.g., Clontech). Within one embodiment, the AD4 gene is isolated by PCR performed on genomic DNA, cDNA or libraries, or by probe hybridization of genomic DNA or cDNA libraries. Primers for PCR and probes for hybridization screening may be designed based on the DNA sequence of AD4 presented herein. The DNA sequence of an AD4 gene is presented in FIG. 1A and B; (SEQ ID NO:1) and the predicted amino acid sequence is presented in FIG. 2. (SEQ ID NO:2) Primers for PCR should be derived from sequences in the 5' and 3' untranslated region in order to isolate a full-length cDNA. The primers should not have self-complementary sequences nor have complementary sequences at their 3' end (to prevent primer-dimer formation). Preferably, the primers have a GC content of about 50% and contain restriction sites. The primers are annealed to cDNA and sufficient cycles of PCR are performed to yield a product readily visualized by gel electrophoresis and staining. The amplified fragment is purified and inserted into a vector, such as λ gt10 or pBS(M13+), and propagated. An oligonucleotide hybridization probe suitable for screening genomic or cDNA libraries may be designed based on the sequence provided herein. Preferably, the oligonucleotide is 20–30 bases long. Such an oligonucleotide may be synthesized by automated synthesis. The oligonucleotide may be conveniently labeled at the 5' end with a reporter molecule, such as a radionuclide, (e.g., $^{32}$P) or biotin. The library is plated as colonies or phage, depending upon the vector, and the recombinant DNA is transferred to nylon or nitrocellulose membranes. Following denaturation, neutralization, and fixation of the DNA to the membrane, the membranes are hybridized with the labeled probe. The membranes are washed and the reporter molecule detected. The hybridizing colonies or phage are isolated and propagated. Candidate clones or PCR amplified fragments may be verified as containing AD4 DNA by any of various means. For example, the candidate clones may be hybridized with a second, nonoverlapping probe or subjected to DNA sequence analysis. In these ways, clones containing AD4 gene, which are suitable for use in the present invention are isolated.

The structure of the proteins encoded by the nucleic acid molecules described herein may be predicted from the primary translation products using the hydrophobicity plot function of, for example, P/C Gene or Intelligenetics Suite (Intelligenetics, Mountain View, Calif.), or according to the methods described by Kyte and Doolittle (*J. Mol. Biol.* 157:105–132, 1982). One such structure is depicted in FIG. 4, which is a hydropathy plot of an AD4 gene product. As is evident from this figure, the plot depicts a protein with an extracellular domain, three extracellular loop domains, three intracellular loop domains, seven transmembrane regions, and an intracellular domain.

AD4 proteins of the present invention may be in the form of acidic or basic salts, or in neutral form. In addition, individual amino acid residues may be modified by oxidation or reduction. Furthermore, various substitutions, deletions, or additions may be made to the amino acid or nucleic acid sequences, the net effect of which is to retain or further enhance or decrease the biological activity of the mutant or wild-type protein. Moreover, due to degeneracy in the genetic code, there may be considerable variation in nucleotide sequences encoding the same amino acid sequence.

Other derivatives of the AD4 proteins disclosed herein include conjugates of the proteins along with other proteins or polypeptides. This may be accomplished, for example, by the synthesis of N-terminal or C-terminal fusion proteins which may be added to facilitate purification or identification of AD4 proteins (see U.S. Pat. No. 4,851,341, see also, Hopp et al., *Bio/Technology* 6:1204, 1988.) Alternatively, fusion proteins such as AD4-βgalactosidase or AD4-luciferase may be constructed in order to assist in the identification, expression, and analysis of AD4 proteins.

AD4 proteins of the present invention may be constructed using a wide variety of techniques including for example, that described in Example 5. Further, mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

Alternatively, oligonucleotide-directed site-specific (or segment specific) mutagenesis procedures may be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, Jan. 12–19, 1985,); Smith et al. (*Genetic Engineering: Principles and Methods*, Plenum Press, 1981); and Sambrook et al. (supra). Deletion or truncation derivatives of AD4 proteins (e.g., a soluble extracellular portion) may also be constructed by utilizing convenient restriction endonuclease sites adjacent to the desired deletion. Subsequent to restriction, overhangs may be filled in, and the DNA relegated. Exemplary methods of making the alterations set forth above are disclosed by Sambrook et al. (*Molecular Cloning: A Laboratory Manual*, 2d Ed., Cold Spring Harbor Laboratory Press, 1989).

Mutations, which are made in the nucleic acid molecules of the present invention preferably preserve the reading frame of the coding sequences. Furthermore, the mutations will preferably not create complementary regions that could hybridize to produce secondary mRNA structures, such as loops or hairpins, that would adversely affect translation of the mRNA. Although a mutation site may be predetermined, it is not necessary that the nature of the mutation per se be predetermined. For example, in order to select for optimum characteristics of mutants at a given site, random mutagenesis may be conducted at the target codon and the expressed mutants screened for indicative biological activity. Alternatively, mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

AD4 proteins may also be constructed utilizing techniques of PCR mutagenesis, chemical mutagenesis (Drinkwater and Klinedinst, *PNAS* 83:3402–3406, 1986), by forced nucleotide misincorporation (e.g., Liao and Wise *Gene* 88:107–111, 1990), or by use of randomly mutagenized oligonucleotides (Horwitz et al., *Genome* 3:112–117, 1989). Particularly preferred methods for constructing Alzheimer Disease Proteins are set forth in more detail below in the Examples.

Proteins can be isolated by, among other methods, culturing suitable host and vector systems to produce the recombinant translation products of the present invention. Supernatants from such cell lines, or protein inclusions or whole cells where the protein is not excreted into the supernatant, can then be treated by a variety of purification procedures in order to isolate the desired proteins. For example, the supernatant may be first concentrated using commercially available protein concentration filters, such as an Amicon or Millipore Pellicon ultrafiltration unit. Following concentration, the concentrate may be applied to a suitable purification matrix such as, for example, an anti-protein antibody bound to a suitable support. Alternatively, anion or cation exchange resins may be employed in order to purify the protein. As a further alternative, one or more reverse-phase high performance liquid chromatography (RP-HPLC) steps may be employed to further purify the protein. Other methods of isolating the proteins of the present invention are well known in the skill of the art.

A protein is deemed to be "isolated" within the context of the present invention if no other (undesired) protein is detected pursuant to SDS-PAGE analysis followed by Coomassie blue staining. Within other embodiments, the desired protein can be isolated such that no other (undesired) protein is detected pursuant to SDS-PAGE analysis followed by silver staining.

The present invention also provides for the manipulation and expression of the above described genes by culturing host cells containing a vector capable of expressing the above-described genes. Such vectors or vector constructs include either synthetic or cDNA-derived nucleic acid molecules encoding AD4 proteins, which are operably linked to suitable transcriptional or translational regulatory elements. Suitable regulatory elements may be derived from a variety of sources, including bacterial, fungal, viral, mammalian, insect, or plant genes. Selection of appropriate regulatory elements is dependent on the host cell chosen, and may be readily accomplished by one of ordinary skill in the art. Examples of regulatory elements include: a transcriptional promoter and enhancer or RNA polymerase binding sequence, a transcriptional terminator, and a ribosomal binding sequence, including a translation initiation signal.

Nucleic acid molecules that encode any of the AD4 proteins described above may be readily expressed by a wide variety of prokaryotic and eukaryotic host cells, including bacterial, mammalian, yeast or other fungi, viral, insect, or plant cells. Methods for transforming or transfecting such cells to express foreign DNA are well known in the art (see, e.g., Itakura et al., U.S. Pat. No. 4,704,362; Hinnen et al., *Proc. Natl. Acad. Sci. USA* 75:1929–1933, 1978; Murray et al., U.S. Pat. No. 4,801,542; Upshall et al., U.S. Pat. No. 4,935,349; Hagen et al., U.S. Pat. No. 4,784,950; Axel et al., U.S. Pat. No. 4,399,216; Goeddel et al., U.S. Pat. No. 4,766,075; and Sambrook et al. *Molecular Cloning: A Laboratory Manual*, 2nd edition, Cold Spring Harbor Laboratory Press, 1989; for plant cells see Czako and Marton, *Plant Physiol.* 104:1067–1071, 1994; and Paszkowski et al., *Biotech.* 24:387–392, 1992).

Bacterial host cells suitable for carrying out the present invention include *E coli, B. subtilis, Salmonella typhimurium*, and various species within the genus' Pseudomonas, Streptomyces, and Staphylococcus, as well as many other bacterial species well known to one of ordinary skill in the art. Representative examples of bacterial host cells include DH5α(Stratagene, LaJolla, Calif.).

Bacterial expression vectors preferably comprise a promoter which functions in the host cell, one or more selectable phenotypic markers, and a bacterial origin of replication. Representative promoters include the β-lactamase (penicillinase) and lactose promoter system (see Chang et al., *Nature* 275:615, 1978), the T7 RNA polymerase promoter (Studier et al., *Meth. Enzymol.* 185:60–89, 1990), the lambda promoter (Elvin et al., *Gene* 87:123–126, 1990), the trp promoter (Nichols and Yanofsky, *Meth. in Enzymology* 101:155, 1983) and the tac promoter (Russell et al., *Gene* 20: 231, 1982). Representative selectable markers include various antibiotic resistance markers such as the kanamycin or ampicillin resistance genes. Many plasmids suitable for transforming host cells are well known in the art, including among others, pBR322 (see Bolivar et al., *Gene* 2:95, 1977), the pUC plasmids pUC18, pUC19, pUC118, pUC119 (see Messing, *Meth. in Enzymology* 101:20–77, 1983 and Vieira and Messing, *Gene* 19:259–268, 1982), and pNH8A, pNH16a, pNH18a, and Bluescript M13 (Stratagene, La Jolla, Calif.).

Yeast and fungi host cells suitable for carrying out the present invention include, among others, *Saccharomyces pombe, Saccharomyces cerevisiae*, the genera Pichia or Kluyveromyces and various species of the genus Aspergillus (McKnight et al., U.S. Pat. No. 4,935,349). Suitable expression vectors for yeast and fungi include, among others, YCp50 (ATCC No. 37419) for yeast, and the amdS cloning vector pV3 (Turnbull, *Bio/Technology* 7:169, 1989), YRp7 (Struhl et al., *Proc. Natl. Acad. Sci. USA* 76:1035–1039, 1978), YEp13 (Broach et al., *Gene* 8:121–133, 1979), pJDB249 and pJDB219 (Beggs, *Nature* 275:104–108, 1978) and derivatives thereof.

Preferred promoters for use in yeast include promoters from yeast glycolytic genes (Hitzeman et al., *J. Biol. Chem.* 255:12073–12080, 1980; Alber and Kawasaki, *J. Mol. Appl. Genet.* 1:419–434, 1982) or alcohol dehydrogenase genes (Young et al., in *Genetic Engineering of Microorganisms for Chemicals*, Hollaender et al. (eds.), p. 355, Plenum, New York, 1982; Ammerer, *Meth. Enzymol.* 101:192–201, 1983). Examples of useful promoters for fungi vectors include those derived from *Aspergillus nidulans* glycolytic genes, such as the adh3 promoter (McKnight et al., *EMBO J.* 4:2093–2099, 1985). The expression units may also include a transcriptional terminator. An example of a suitable terminator is the adh3 terminator (McKnight et al., ibid., 1985).

As with bacterial vectors, the yeast vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include leu2 (Broach et al., ibid), ura3 (Botstein et al., *Gene* 8:17, 1979), or his3 (Struhl et al., ibid.). Another suitable selectable marker is the cat gene, which confers chloramphenicol resistance on yeast cells.

Techniques for transforming fungi are well known in the literature, and have been described, for instance, by Beggs (ibid.), Hinnen et al. (*Proc. Natl. Acad. Sci. USA* 75:1929–1933, 1978), Yelton et al. (*Proc. Natl. Acad. Sci. USA* 81:1740–1747, 1984), and Russell (*Nature* 301:167–169, 1983). The genotype of the host cell may contain a genetic defect that is complemented by the selectable marker present on the expression vector. Choice of a particular host and selectable marker is well within the level of ordinary skill in the art.

Protocols for the transformation of yeast are also well known to those of ordinary skill in the art. For example, transformation may be readily accomplished either by preparation of spheroplasts of yeast with DNA (see Hinnen et al., *PNAS USA* 75:1929, 1978) or by treatment with alkaline salts such as LiCl (see Itoh et al., *J. Bacteriology* 153:163, 1983). Transformation of fungi may also be carried out using polyethylene glycol as described by Cullen et al. (*Bio/Technology* 5:369, 1987).

Viral vectors include those which comprise a promoter that directs the expression of an isolated nucleic acid molecule that encodes an Alzheimer Disease Protein as described above. A wide variety of promoters may be utilized within the context of the present invention, including for example, promoters such as MoMLV LTR, RSV LTR, Friend MuLV LTR, Adenoviral promoter (Ohno et al., *Science* 265: 781–784, 1994), neomycin phosphotransferase promoter/enhancer, late parvovirus promoter (Koering et al., *Hum. Gene Therap.* 5:457–463, 1994), Herpes TK promoter, SV40 promoter, metallothionein IIa gene enhancer/promoter, cytomegalovirus immediate early promoter, and the cytomegalovirus immediate late promoter. Within particularly preferred embodiments of the invention, the promoter is a tissue-specific promoter (see e.g., WO 91/02805; EP 0,415,731; and WO 90/07936). Representative examples of suitable tissue specific promoters include neural specific enolase promoter, platelet derived growth factor beta promoter, bone morpho-genetic protein promoter, human alpha1-chimaerin, promoter, synapsin I promoter and synapsin II promoter. In addition to the above-noted promoters, other viral-specific promoters (e.g., retroviral promoters (including those noted above, as well as others such as HIV promoters), hepatitis, herpes (e.g., EBV), and bacterial, fungal or parasitic (e.g., malarial) -specific promoters may be utilized in order to target a specific cell or tissue which is infected with a virus, bacteria, fungus or parasite.

Thus, AD4 proteins of the present invention may be expressed from a variety of viral vectors, including for example, herpes viral vectors (e.g., U.S. Pat. No. 5,288,641), adenoviral vectors (e.g., WO 94/26914, WO 93/9191; Kolls et al., *PNAS* 91(1):215–219, 1994; Kass-Eisler et al., *PNAS* 90(24):11498–502, 1993; Guzman et al., *Circulation* 88(6):2838–48, 1993; Guzman et al., *Cir. Res.* 73(6):1202–1207, 1993; Zabner et al., *Cell* 75(2):207–216, 1993; Li et al., *Hum Gene Ther.* 4(4):403–409, 1993; Caillaud et al., *Eur. J. Neurosci.* 5(10:1287–1291, 1993; Vincent et al., *Nat. Genet.* 5(2): 130–134, 1993; Jaffe et al., *Nat. Genet.* 1(5): 372–378, 1992; and Levrero et al, *Gene* 101(2): 195–202, 1991), adeno-associated viral vectors (WO 95/13365; Flotte et al., *PNAS* 90(22): 10613–10617, 1993), baculovirus vectors, parvovirus vectors (Koering et al., *Hum. Gene Therap.* 5:457–463, 1994), pox virus vectors (Panicali and Paoletti, *PNAS* 79:4927–4931, 1982; and Ozaki et al., *Biochem. Biophys. Res. Comm.* 193(2): 653–660, 1993), and retroviruses (e.g., EP 0,415,731; WO 90/07936; WO 91/0285, WO 94/03622; WO 93/25698; WO 93/25234; U.S. Patent No. 5,219,740; WO 93/11230; WO 93/10218. Viral vectors may likewise be constructed which contain a mixture of different elements (e.g., promoters, envelope sequences and the like) from different viruses, or non-viral sources. Within various embodiments, either the viral vector itself, or a viral particle which contains the viral vector may be utilized in the methods and compositions described below.

Mammalian cells suitable for carrying out the present invention include, among others: PC12 (ATCC No. CRL1721), N1E-115 neuroblastoma, SK-N-BE(2)C neuroblastoma, SHSY5 adrenergic neuroblastoma, NS20Y and NG108-15 murine cholinergic cell lines, or rat F2 dorsal root ganglion line, COS (e.g., ATCC No. CRL 1650 or 1651), BHK (e.g., ATCC No. CRL 6281; BHK 570 cell line (deposited with the American Type Culture Collection under accession number CRL 10314), CHO (ATCC No. CCL 61), HeLa (e.g., ATCC No. CCL 2), 293 (ATCC No. 1573; Graham et al., *J. Gen. Virol.* 36:59–72, 1977) and NS-1 cells. Other mammalian cell lines may be used within the present invention, including Rat Hep I (ATCC No. CRL 1600), Rat Hep II (ATCC No. CRL 1548), TCMK (ATCC No. CCL 139), Human lung (ATCC No. CCL 75.1), Human hepatoma (ATCC No. HTB-52), Hep G2 (ATCC No. HB 8065), Mouse liver (ATCC No. CCL 29.1), NCTC 1469 (ATCC No. CCL 9.1), SP2/0-Ag14 (ATCC No. 1581), HIT-T15 (ATCC No. CRL 1777), and RINm 5AHT$_2$B (Orskov and Nielson, *FEBS* 229(1): 175–178, 1988).

Mammalian expression vectors for use in carrying out the present invention will include a promoter capable of directing the transcription of a cloned gene or cDNA. Preferred promoters include viral promoters and cellular promoters. Viral promoters include the cytomegalovirus immediate early promoter (Boshart et al., *Cell* 41:521–530, 1985), cytomegalovirus immediate late promoter, SV40 promoter (Subramani et al., *Mol. Cell. Biol.* 1:854–864, 1981), MMTV LTR, RSV LTR, metallothionein-1, adenovirus Ela. Cellular promoters include the mouse metallothionein-1 promoter (Palmiter et al., U.S. Pat. No. 4,579,821), a mouse V$_\kappa$ promoter (Bergman et al., *Proc. Natl. Acad. Sci. USA* 81:7041–7045, 1983; Grant et al., *Nucl. Acids Res.* 15:5496, 1987) and a mouse V$_H$ promoter (Loh et al., *Cell* 33:85–93, 1983). The choice of promoter will depend, at least in part, upon the level of expression desired or the recipient cell line to be transfected.

Such expression vectors may also contain a set of RNA splice sites located downstream from the promoter and upstream from the DNA sequence encoding the peptide or protein of interest. Preferred RNA splice sites may be obtained from adenovirus and/or immunoglobulin genes. Also contained in the expression vectors is a polyadenylation signal located downstream of the coding sequence of interest. Suitable polyadenylation signals include the early or late polyadenylation signals from SV40 (Kaufman and Sharp, ibid.), the polyadenylation signal from the Adenovirus 5 E1B region and the human growth hormone gene terminator (DeNoto et al., *Nuc. Acids Res.* 9:3719–3730, 1981). The expression vectors may include a noncoding viral leader sequence, such as the Adenovirus 2 tripartite leader, located between the promoter and the RNA splice sites. Preferred vectors may also include enhancer sequences, such as the SV40 enhancer and the mouse Ig heavy chain enhancer (Gillies, *Cell* 33:717–728, 1983). Expression vectors may also include sequences encoding the adenovirus VA RNAs. Suitable expression vectors can be obtained from commercial sources (e.g., Stratagene, La Jolla, Calif.).

Vector constructs comprising cloned DNA sequences can be introduced into cultured mammalian cells by, for example, calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841–845, 1982), or DEAE-dextran mediated transfection (Ausubel et al. (eds.), *Current Protocols in Molecular Biology*, John Wiley and Sons, Inc., NY, 1987). To identify cells that have stably integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. Preferred amplifiable selectable markers are the DHFR gene and the neomycin resistance gene. Selectable markers are reviewed by Thilly (*Mammalian Cell Technology*, Butterworth Publishers, Stoneham, Mass., which is incorporated herein by reference).

Mammalian cells containing a suitable vector are allowed to grow for a period of time, typically 1–2 days, to begin expressing the DNA sequence(s) of interest. Drug selection is then applied to select for growth of cells that are expressing the selectable marker in a stable fashion. For cells that have been transfected with an amplifiable, selectable marker the drug concentration may be increased in a stepwise manner to select for increased copy number of the cloned sequences, thereby increasing expression levels. Cells expressing the introduced sequences are selected and screened for production of the protein of interest in the desired form or at the desired level. Cells that satisfy these criteria can then be cloned and scaled up for production.

Protocols for the transfection of mammalian cells are well known to those of ordinary skill in the art. Representative methods include calcium phosphate mediated transfection, electroporation, lipofection, retroviral, adenoviral and protoplast fusion-mediated transfection (see Sambrook et al., supra).

Numerous insect host cells known in the art can also be useful within the present invention, in light of the subject specification. For example, the use of baculoviruses as vectors for expressing heterologous DNA sequences in insect cells has been reviewed by Atkinson et al. (*Pestic. Sci.* 28:215–224,1990).

Numerous plant host cells known in the art can also be useful within the present invention, in light of the subject specification. For example, the use of *Agrobacterium rhizogenes* as vectors for expressing genes in plant cells has been reviewed by Sinkar et al., (*J Biosci.* (*Bangalore*) 11:47–58, 1987).

AD4 proteins may be prepared by growing (typically by culturing) the host/vector systems described above, in order to express the recombinant Alzheimer Disease Proteins. Recombinantly produced AD4 proteins may be further purified as described in more detail below.

Within related aspects of the present invention, AD4 proteins may be expressed in a transgenic animal whose germ cells and somatic cells contain an AD4 gene which is operably linked to a promoter effective for the expression of the gene may also be expressed in non-human transgenic animals such as mice, rats, rabbits, sheep, dogs and pigs (see Hammer et al. *Nature* 315:680–683, 1985, Palmiter et al. *Science* 222:809–814, 1983, Brinster et al. *Proc. Natl. Acad. Sci. USA* 82:4438–4442, 1985, Palmiter and Brinster *Cell* 41:343–345, 1985 and U.S. Pat. Nos. 5,175,383, 5,087,571, 4,736,866, 5,387,742, 5,347,075, 5,221,778, and 5,175, 384). Briefly, an expression vector, including a nucleic acid molecule to be expressed together with appropriately positioned expression control sequences, is introduced into pronuclei of fertilized eggs, for example, by microinjection. Integration of the injected DNA is detected by blot analysis of DNA from tissue samples. It is preferred that the introduced DNA be incorporated into the germ line of the animal so that it is passed on to the animal's progeny. Tissue-specific expression may be achieved through the use of a tissue-specific promoter, or through the use of an inducible promoter, such as the metallothionein gene promoter (Palmiter et al., 1983, ibid), which allows regulated expression of the transgene.

Vectors of the present invention may contain or express a wide variety of additional nucleic acid molecules in place of or in addition to an AD4 protein as described above, either from one or several separate promoters. For example, the viral vector may express a lymphokine or lymphokine receptor, antisense or ribozyme sequence or toxins. Representative examples of lymphokines include IL-1, IL-2, IL-3, IL-4, IL-5, IL-6, IL-7, IL-8, IL-9, IL-10, IL-11, IL-12, IL-13, IL-14, IL-15, GM-CSF, G-CSF, M-CSF, alpha-interferon, beta-interferon, gamma interferon, and tumor necrosis factors, as well as their respective receptors. Representative examples of antisense sequences include anti-sense sequences which block the expression of AD4 protein mutants. Representative examples of toxins include: ricin, abrin, diphtheria toxin, cholera toxin, saporin, gelonin, pokeweed antiviral protein, tritin, Shigella toxin, and Pseudomonas exotoxin A.

Within other aspects of the invention, antisense oligo-nucleotide molecules are provided which specifically inhibit expression of mutant AD4 nucleic acid sequences (see generally, Hirashima et al. in *Molecular Biology of RNA: New Perspectives* (M. Inouye and B. S. Dudock, eds., 1987 Academic Press, San Diego, p. 401); *Oligonucleotides: Antisense Inhibitors of Gene Expression* (J. S. Cohen, ed., 1989 MacMillan Press, London); Stein and Cheng, *Science* 261:1004–1012 (1993); WO 95/10607; U.S. Pat. No. 5,359, 051; WO 92106693; and EP-A2-612844). Briefly, such molecules are constructed such that they are complementary to, and able to form Watson-Crick base pairs with, a region of transcribed AD4 mutant mRNA sequence containing an AD4 mutation. The resultant double-stranded nucleic acid interferes with subsequent processing of the mRNA, thereby preventing protein synthesis.

Within other related aspects of the invention, ribozyme molecules are provided wherein an antisense oligonucleotide sequence is incorporated into a ribozyme which can specifically cleave mRNA molecules transcribed from a mutant AD4 gene (see generally, Kim et al. *Proc. Nat. Acad. Sci. USA* 84:8788 (1987); Haseloff, et al. *Nature* 234:585 (1988), Cech, *JAMA* 260:3030 (1988); Jeffries, et al. *Nucleic Acids Res.* 17:1371 (1989); U.S. Pat. No. 5,093,246; U.S. Pat. No. 5,354,855; U.S. Pat. No. 5,144,019; U.S. Pat. No. 5,272,262; U.S. Pat. No. 5,254,678; and U.S. Pat. No. 4,987,071). According to this aspect of the invention, the antisense sequence which is incorporated into a ribozyme includes a sequence complementary to, and able to form Watson-Crick base pairs with, a region of the transcribed mutant AD4 mRNA containing an AD4 mutation. The antisense sequence thus becomes a targeting agent for delivery of catalytic ribozyme activity specifically to mutant AD4 mRNA, where such catalytic activity cleaves the mRNA to render it incapable of being subsequently processed for AD4 protein translation.

HOST CELLS

As discussed above, nucleic acid molecules which encode the AD4 proteins of the present invention (or the vectors which contain and/or express related mutants) may readily be introduced into a wide variety of host cells. Representative examples of such host cells include plant cells, eukaryotic cells, and prokaryotic cells. Within preferred embodiments, the nucleic acid molecules are introduced into cells from a vertebrate or warm-blooded animal, such as a human, macaque, dog, cow, horse, pig, sheep, rat, hamster, mouse or fish cell, or any hybrid thereof.

Preferred prokaryotic host cells for use within the present invention include *E. coli*, Salmonella, Bacillus, Shigella, Pseudomonas, Streptomyces and other genera. Techniques for transforming these hosts and expressing foreign DNA sequences cloned therein are well known in the art (see, e.g., Maniatis et al., *Molecular Cloning: A Laboratory Manual*, Cold Spring Harbor Laboratory, 1982, which is incorporated herein by reference; or Sambrook et al., supra). Vectors used for expressing cloned DNA sequences in bacterial hosts will generally contain a selectable marker, such as a gene for antibiotic resistance, and a promoter that functions in the host cell. Appropriate promoters include the trp (Nichols and Yanofsky, *Meth. Enzymol.* 101: 155–164, 1983), lac (Casadaban et al., *J. Bacteriol.* 143:971–980, 1980), and phage λ (Queen, *J. Mol. Appl. Genet.* 2:1–10, 1983) promoter systems. Plasmids useful for transforming bacteria include the pUC plasmids (Messing, *Meth. Enzymol.* 101:20–78, 1983; Vieira and Messing, *Gene* 19:259–268, 1982), pBR322 (Bolivar et al., *Gene* 2:95–113, 1977), pCQV2 (Queen, ibid.), and derivatives thereof Plasmids may contain both viral and bacterial elements.

Preferred eukaryotic cells include cultured mammalian cell lines (e.g., rodent or human cell lines) and fungal cells, including species of yeast (e.g., Saccharomyces spp., particularly *S. cerevisiae*, Schizosaccharomyces spp., or Kluyveromyces spp.) or filamentous fungi (e.g., Aspergillus spp., Neurospora spp.). Strains of the yeast *Saccharomyces cerevisiae* are particularly preferred. Methods for producing recombinant proteins in a variety of prokaryotic and eukaryotic host cells are generally known in the art (see, "Gene Expression Technology," *Methods in Enzymology*, Vol. 185, Goeddel (ed.), Academic Press, San Diego, Calif., 1990; see also, "Guide to Yeast Genetics and Molecular Biology," *Methods in Enzymology*, Guthrie and Fink (eds.), Academic Press, San Diego, Calif., 1991). In general, a host cell will be selected on the basis of its ability to produce the protein of interest at a high level or its ability to carry out at least some of the processing steps necessary for the biological activity of the protein. In this way, the number of cloned DNA sequences that must be introduced into the host cell can be minimized and overall yield of biologically active protein can be maximized.

The nucleic acid molecules (or vectors) may be introduced into host cells by a wide variety of mechanisms, including for example calcium phosphate-mediated transfection (Wigler et al., *Cell* 14:725, 1978), lipofection; gene gun (Corsaro and Pearson, *Somatic Cell Gen.* 7:603, 1981; Graham and Van der Eb, *Virology* 52:456, 1973), electroporation (Neumann et al., *EMBO J.* 1:841–845, 1982), retroviral, adenoviral, protoplast fusion-mediated transfection or DEAE-dextran mediated transfection (Ausubel et al., (eds.), *Current Protocols in Molecular Biology*, John Wiley and Sons, Inc., NY, N.Y., 1987).

Host cells containing vector constructs of the present invention are then cultured to express a DNA molecule as described above. The cells are cultured according to standard methods in a culture medium containing nutrients required for growth of the chosen host cells. A variety of suitable media are known in the art and generally include a carbon source, a nitrogen source, essential amino acids, vitamins and minerals, as well as other components, e.g., growth factors or serum, that may be required by the particular host cells. The growth medium will generally select for cells containing the DNA construct(s) by, for example, drug selection or deficiency in an essential nutrient which is complemented by the selectable marker on the DNA construct or co-transfected with the DNA construct.

Suitable growth conditions for yeast cells, for example, include culturing in a chemically defined medium, comprising a nitrogen source, which may be a non-amino acid nitrogen source or a yeast extract, inorganic salts, vitamins and essential amino acid supplements at a temperature between 4° C. and 37° C., with 30° C. being particularly preferred. The pH of the medium is preferably maintained at a pH greater than 2 and less than 8, more preferably pH 5–6. Methods for maintaining a stable pH include buffering and constant pH control. Preferred agents for pH control include sodium hydroxide. Preferred buffering agents include succinic acid and Bis-Tris (Sigma Chemical Co., St. Louis, Mo.). Due to the tendency of yeast host cells to hyperglycosylate heterologous proteins, it may be preferable to express the nucleic acid molecules of the present invention in yeast cells having a defect in a gene required for asparagine-inked glycosylation. Such cells are preferably grown in a medium containing an osmotic stabilizer. A preferred osmotic stabilizer is sorbitol supplemented into the medium at a concentration between 0.1 M and 1.5 M, preferably at 0.5 M or 1.0 M.

Cultured mammalian cells are generally cultured in commercially available serum-containing or serum-free media. Selection of a medium and growth conditions appropriate for the particular cell line used is well within the level of ordinary skill in the art.

ANTIBODIES

Antibodies to the AD4 proteins discussed above may readily be prepared given the disclosure provided herein. Such antibodies may, within certain embodiments, specifically recognize wild-type AD4 protein rather than mutant AD4 protein, mutant AD4 protein rather than wild-type AD4 protein, or equally recognize both wild-type and mutant AD4 protein. Within the context of the present invention, antibodies are understood to include monoclonal antibodies, polyclonal antibodies, anti-idiotypic antibodies, antibody fragments (e.g., Fab, and F(ab')$_2$, F$_v$ variable regions, or complementarity determining regions). As discussed above, antibodies are understood to be specific against an AD4 protein if it binds with a K$_a$ of greater than or equal to $10^{-7}$M, preferably greater than of equal to $10^{-8}$M. The affinity of a monoclonal antibody or binding partner can be readily determined by one of ordinary skill in the art (see Scatchard, *Ann. N.Y. Acad. Sci.* 51:660–672, 1949).

Briefly, polyclonal antibodies may be readily generated by one of ordinary skill in the art from a variety of warm-blooded animals such as horses, cows, various fowl, rabbits, mice, or rats. Typically, an AD4 protein or unique AD4 peptide of 13–20 amino acids (preferably conjugated to keyhole limpet hemocyanin by cross-linking with glutaraldehyde) is utilized to immunize the animal through intraperitoneal, intramuscular, intraocular, or subcutaneous injections, an adjuvant such as Freund's complete or incomplete adjuvant. Following several booster immunizations, samples of serum are collected and tested for reactivity to the AD4 protein. Particularly preferred polyclonal antisera will give a signal on one of these assays that is at least three times greater than background. Once the titer of the animal has reached a plateau in terms of its reactivity to the protein, larger quantities of antisera may be readily obtained either by weekly bleedings, or by exsanguinating the animal.

Monoclonal antibodies may also be readily generated using conventional techniques (see U.S. Pat. Nos. RE 32,011, 4,902,614, 4,543,439, and 4,411,993 which are incorporated herein by reference; see also *Monoclonal Antibodies, Hybridomas: A New Dimension in Biological Analyses*, Plenum Press, Kennett, McKearn, and Bechtol (eds.), 1980, and *Antibodies: A Laboratory Manual*, Harlow and Lane (eds.), Cold Spring Harbor Laboratory Press, 1988, which are also incorporated herein by reference).

Briefly, within one embodiment a subject animal such as a rat or mouse is injected with an AD4 protein or portion thereof as described above. The protein may be admixed with an adjuvant such as Freund's complete or incomplete adjuvant in order to increase the resultant immune response. Between one and three weeks after the initial immunization the animal may be reimmunized with another booster immunization, and tested for reactivity to the protein utilizing assays described above. Once the animal has reached a plateau in its reactivity to the injected protein, it is sacrificed, and organs which contain large numbers of B cells such as the spleen and lymph nodes are harvested.

Cells which are obtained from the immunized animal may be immortalized by transfection with a virus such as the Epstein-Barr virus (EBV) (see Glasky and Reading, *Hybridoma* 8(4): 377–389, 1989). Alternatively, within a preferred embodiment, the harvested spleen and/or lymph node cell suspensions are fused with a suitable myeloma cell in order to create a "hybridoma" which secretes monoclonal antibody. Suitable myeloma lines include, for example, NS-1 (ATCC No. TIB 18), and P3X63-Ag8.653 (ATCC No. CRL 1580).

Following the fusion, the cells may be placed into culture plates containing a suitable medium, such as RPMI 1640, or DMEM (Dulbecco's Modified Eagles Medium) (JRH Biosciences, Lenexa, Kans.), as well as additional ingredients, such as Fetal Bovine Serum (FBS, i.e., from Hyclone, Logan, Utah, or JRH Biosciences). Additionally, the medium should contain a reagent which selectively allows for the growth of fused spleen and myeloma cells such as HAT (hypoxanthine, aminopterin, and thymidine) (Sigma Chemical Co., St. Louis, Mo.). After about seven days, the resulting fused cells or hybridomas may be screened in order to determine the presence of antibodies which are reactive against an AD4 protein. A wide variety of assays may be utilized to determine the presence of antibodies which are reactive against the proteins of the present invention, including for example countercurrent immunoelectrophoresis, radioimmunoassays, radioimmunoprecipitations, enzyme-linked immunosorbent assays (ELISA), dot blot assays, Western blots, immunoprecipitation, inhibition or competition assays, and sandwich assays (see U.S. Pat. Nos. 4,376,110 and 4,486,530; see also *Antibodies: A Laboratory Manual*, Harlow and Lane (eds.), Cold Spring Harbor Laboratory Press, 1988). Following several clonal dilutions and reassays, a hybridoma producing antibodies reactive against the AD4 protein may be isolated.

Other techniques may also be utilized to construct monoclonal antibodies (see William D. Huse et al., "Generation of a Large Combinational Library of the Immunoglobulin Repertoire in Phage Lambda," *Science* 246:1275–1281, December 1989; see also L. Sastry et al., "Cloning of the Immunological Repertoire in *Escherichia coli* for Generation of Monoclonal Catalytic Antibodies: Construction of a Heavy Chain Variable Region-Specific cDNA Library," *Proc. Natl. Acad. Sci. USA* 86:5728–5732, August 1989; see also Michelle Alting-Mees et al., "Monoclonal Antibody Expression Libraries: A Rapid Alternative to Hybridomas," *Strategies in Molecular Biology* 3:1–9, January 1990; these references describe a commercial system available from Stratacyte, La Jolla, Calif., which enables the production of antibodies through recombinant techniques). Briefly, mRNA is isolated from a B cell population, and utilized to create heavy and light chain immunoglobulin cDNA expression libraries in the λ ImmunoZap(H) and λImmunoZap(L) vectors. These vectors may be screened individually or co-expressed to form Fab fragments or antibodies (see Huse et al., supra; see also Sastry et al., supra). Positive plaques may subsequently be converted to a non-lytic plasmid which allows high level expression of monoclonal antibody fragments from *E. coli*.

Similarly, portions or fragments, such as Fab or $F_v$ fragments, of antibodies may also be constructed utilizing conventional enzymatic digestion or recombinant DNA techniques to incorporate the variable regions of a gene which encodes a specifically binding antibody. Within one embodiment, the genes which encode the variable region from a hybridoma producing a monoclonal antibody of interest are amplified using nucleotide primers for the variable region. These primers may be synthesized by one of ordinary skill in the art, or may be purchased from commercially available sources. Stratacyte (La Jolla, Calif.) sells primers for mouse and human variable regions including, among others, primers for $V_{Ha}$, $V_{Hb}$, $V_{Hc}$, $V_{Hd}$, $C_{H1}$, $V_L$ and $C_L$ regions. These primers may be utilized to amplify heavy or light chain variable regions, which may then be inserted into vectors such as ImmunoZAP™ H or ImmunoZAP™ L (Stratacyte), respectively. These vectors may then be introduced into *E. coli*, yeast, or mammalian-based systems for expression. Utilizing these techniques, large amounts of a single-chain protein containing a fusion of the $V_H$ and $V_L$ domains may be produced (see Bird et al., *Science* 242:423–426, 1988). In addition, such techniques may be utilized to change a "murine" antibody to a "human" antibody, without altering the binding specificity of the antibody.

Once suitable antibodies have been obtained, they may be isolated or purified by many techniques well known to those of ordinary skill in the art (see *Antibodies: A Laboratory Manual*, Harlow and Lane (eds.), Cold Spring Harbor Laboratory Press, 1988). Suitable techniques include peptide or protein affinity columns, HPLC or RP-HPLC, purification on protein A or protein G columns, or any combination of these techniques.

Antibodies of the present invention have many uses. For example, antibodies may be utilized in flow cytometry to sort cells bearing such an AD4 protein. Briefly, in order to detect the protein or peptide of interest on cells, the cells are incubated with a labeled monoclonal antibody which specifically binds to the protein of interest, followed by detection of the presence of bound antibody. These steps may also be accomplished with additional steps such as washings to remove unbound antibody. Labels suitable for use within the present invention are well known in the art including, among others, flourescein isothiocyanate (FITC), phycoerythrin (PE), horse radish peroxidase (HRP), and colloidal gold. Particularly preferred for use in flow cytometry is FITC, which may be conjugated to purified antibody according to the method of Keltkamp in "Conjugation of Fluorescein Isothiocyanate to Antibodies. I. Experiments on the Conditions of Conjugation," *Immunology* 18:865–873, 1970. (See also Keltkamp, "Conjugation of Fluorescein Isothiocyanate to Antibodies. II. A Reproducible Method," *Immunology* 18:875–881, 1970; Goding, "Conjugation of Antibodies with Fluorochromes: Modification to the Standard Methods," *J. Immunol. Methods* 13:215–226, 1970.).

ASSAYS

Assays useful within the context of the present invention include those assays for detecting agonists or antagonists of AD4 protein activity. Other assays are useful for the screening of peptide or organic molecule libraries. Still other assays are useful for the identification and/or isolation of nucleic acid molecules and/or peptides within the present invention, or for diagnosis of a patient with an increased likelihood of contracting Alzheimer's Disease.

A. Nucleic Acid Based Diagnostic Tests

Briefly, another aspect of the present invention provides probes and primers for detecting the AD4 genes and/or mutants thereof. In one embodiment of this aspect, probes are provided that are capable of specifically hybridizing to RNA or DNA from the AD4 gene. For purposes of the present invention, probes are "capable of hybridizing" to AD4 genes DNA or RNA if they hybridize to an AD4 gene under conditions of either high or moderate stringency (see Sambrook et al., supra) but not significantly or detectably to the AD3 gene. Preferably, the probe may be utilized to hybridize to suitable nucleotide sequences under high stringency conditions, such as 5×SSPE, 1×Denhardt's solution (Sambrook et al., supra), 0.1% SDS at 65° C. and at least one wash to remove excess probe in the presence of 0.2×SSC, 1×Denhardt's solution, 0.1% SDS at 65° C. Except as otherwise provided herein, probe sequences are designed to allow hybridization to AD4 genes, but not to DNA or RNA sequences from other genes, such as AD3. The probes are used, for example, to hybridize to nucleic acid that is present in a biological sample isolated from a patient. The hybridized probe is then detected, thereby indicating the presence of the desired cellular nucleic acid. Preferably, the cellular nucleic acid is subjected to an amplification procedure, such as PCR, prior to hybridization. Alternatively, the AD4 gene may be amplified and the amplified product subjected to DNA sequencing. Mutants of AD4 may be detected by DNA sequence analysis or hybridization with allele-specific oligonucleotide probes under conditions and for time sufficient to allow hybridization to the specific allele. Typically, the hybridization buffer and wash will contain tetramethyl ammonium chloride or the like (see Sambrook et al., supra).

Nucleic acid probes of the present invention may be composed of either deoxyribonucleic acids (DNA), ribonucleic acids (RNA), nucleic acid analogues (e.g., peptide nucleic acids), or any combination thereof, and may be as few as about 12 nucleotides in length, usually about 14 to 18 nucleotides in length, and possibly as large as the entire sequence of an AD4 gene. Selection of probe size is somewhat dependent upon the use of the probe, and is within the skill of the art.

Suitable probes can be constructed and labeled using techniques that are well known in the art. Shorter probes of, for example, 12 bases can be generated synthetically and labeled with $^{32}$P using $T_4$ polynucleotide kinase. Longer probes of about 75 bases to less than 1.5 kb are preferably generated by, for example, PCR amplification in the presence of labeled precursors such as [$\alpha$-$^{32}$P]dCTP, digoxigenin-dUTP, or biotin-dATP. Probes of more than 1.5 kb are generally most easily amplified by transfecting a cell with a plasmid containing the relevant probe, growing the transfected cell into large quantities, and purifying the relevant sequence from the transfected cells. (See Sambrook et al., supra.)

Probes can be labeled by a variety of markers, including for example, radioactive markers, fluorescent markers, enzymatic markers, and chromogenic markers. The use of 32P is particularly preferred for marking or labeling a particular probe.

It is a feature of this aspect of the invention that the probes can be utilized to detect the presence of AD4 mRNA or DNA within a sample. However, if the nucleic acid is present in only a limited number, then it may be beneficial to amplify the relevant sequence so that it may be more readily detected or obtained.

A variety of methods may be utilized in order to amplify a selected sequence, including, for example, RNA amplification (see Lizardi et al., *Bio/Technology* 6:1197–1202, 1988; Kramer et al., *Nature* 339:401–402, 1989; Lomeli et al., *Clinical Chem.* 35(9): 1826–1831, 1989; U.S. Pat. No. 4,786,600), and DNA amplification utilizing LCR or Polymerase Chain Reaction ("PCR") (see, U.S. Pat. Nos. 4,683,195, 4,683,202, and 4,800,159) (see also U.S. Pat. Nos. 4,876,187 and 5,011,769, which describe an alternative detection/amplification system comprising the use of scissile linkages), or other nucleic acid amplification procedures that are well within the level of ordinary skill in the art. With respect to PCR, for example, the method may be modified as known in the art. Transcriptional enhancement of PCR may be accomplished by incorporation of bacteriophage T7 RNA polymerase promoter sequences in one of the primary oligonucleotides, and immunoenzymatic detection of the products from the enhanced emitter may be effected using anti-RNA:DNA antibodies (Blais, *Appl. Environ. Microbiol.* 60:348–352, 1994). PCR may also be used in combination with reverse dot-blot hybridization (Iida et al., *FEMS Microbiol. Lett.* 114:167–172, 1993). PCR products may be quantitatively analyzed by incorporation of dUTP (Duplaa et al., *Anal. Biochem.* 212:229–236, 1993), and samples may be filter sampled for PCR-gene probe detection (Bej et al., *Appl. Environ. Microbiol.* 57:3529–3534, 1991).

Within a particularly preferred embodiment, PCR amplification is utilized to detect AD4 DNA. Briefly, as described in greater detail below, a DNA sample is denatured at 95° C. in order to generate single-stranded DNA. Specific primers are then annealed to the single-stranded DNA at 37° C. to 70° C., depending on the proportion of AT/GC in the primers. The primers are extended at 72° C. with Taq DNA polymerase in order to generate the opposite strand to the template. These steps constitute one cycle, which may be repeated in order to amplify the selected sequence.

Within an alternative preferred embodiment, LCR amplification is utilized for amplification. LCR primers are synthesized such that the 5' base of the upstream primer is capable of hybridizing to a unique base pair in a desired gene to specifically detect an AD4 gene.

Within another preferred embodiment, the probes are used in an automated, non-isotopic strategy wherein target nucleic acid sequences are amplified by PCR, and then desired products are determined by a colorimetric oligonucleotide ligation assay (OLA) (Nickerson et al., *Proc. Natl. Acad. Sci. USA* 81:8923–8927, 1990).

Primers for the amplification of a selected sequence should be selected from sequences that are highly specific to AD4 (an not AD3) and form stable duplexes with the target sequence. The primers should also be non-complementary, especially at the 3' end, should not form dimers with themselves or other primers, and should not form secondary structures or duplexes with other regions of DNA. In general, primers of about 18 to 20 nucleotides are preferred, and can be easily synthesized using techniques well known in the art. PCR products, and other nucleic acid amplification products, may be quantitated using techniques known in the art (Duplaa et al., *Anal. Biochem.* 212:229–236, 1993; Higuchi et al., *Bio/Technology* 11:1026–1030).

Within a particularly preferred embodiment, restriction enzyme analysis is used to detect a mutant AD4 gene. For example, within one embodiment the N141I mutation in AD4 creates a Sau3A I restriction site. cDNA, genomic DNA, or amplified AD4 cDNA or genomic DNA is restricted with Sau3 A I. If the AD4 gene contains the N141I alteration, the Sau3A I fragment or amplified product containing codon 141 will be cleaved into two smaller fragments. The cleavage is readily detected by electrophoresis in agarose or acrylamide gels and visualized by ethidium bromide fluorescence or probe hybridization using AD4 gene fragments or oligonucleotides.

B. Antibody-based Diagnostic Tests

Still another aspect of the present invention provides antibodies, as discussed above, for the detection of AD4 gene products in diagnostic tests. A variety of assays can be utilized in order to detect antibodies that specifically bind to the desired protein or peptide. Exemplary assays are described in detail in *Antibodies: A Laboratory Manual*, Harlow and Lane (eds.), Cold Spring Harbor Laboratory Press, 1988. Representative examples of such assays include: countercurrent immuno-electrophoresis (CIEP), radioimmunoassays, radioimmunoprecipitations, enzyme-linked immuno-sorbent assays (ELISA), dot blot assays, inhibition or competition assays, and sandwich assays, immunostick (dipstick) assays, simultaneous immunoassays, immunochromatographic assays, immunofiltration assays, latex bead agglutination assays, immunofluorescent assays, biosensor assays, and low-light detection assays (see U.S. Pat. Nos. 4,376,110 and 4,486,530; see also *Antibodies: A Laboratory Manual*, supra).

A fluorescent antibody test (FA-test) uses a fluorescently-labeled antibody able to bind to one of the proteins of the invention. For detection, visual determinations are made by a technician using fluorescence microscopy, yielding a qualitative result. In a preferred embodiment, this assay is used for the examination of tissue samples and histological sections.

In latex bead agglutination assays, antibodies to one or more of the proteins of the present invention are conjugated to latex beads. The antibodies conjugated to the latex beads are then contacted with a sample under conditions permitting antibodies to bind to desired proteins in the sample, if any. The results are then read visually, yielding a qualitative result. In a preferred embodiment, this format can be used in the field for on-site testing.

Enzyme immunoassays (EIA) include a number of different assays able to utilize the antibodies provided by the present invention. For example, a heterogeneous indirect EIA uses a solid phase coupled with an antibody of the invention and an affinity purified, anti-IgG immunoglobulin preparation. Preferably, the solid phase is a polystyrene microtiter plate. The antibodies and immunoglobulin preparation are then contacted with the sample under conditions permitting antibody binding, which conditions are well known in the art. The results of such an assay can be read visually, but are preferably read using a spectrophotometer, such as an ELISA plate reader, to yield a quantitative result.

An alternative solid phase EIA format includes a plastic-coated ferrous metal beads able to be moved during the procedures of the assay by means of a magnet. Yet another alternative is a low-light detection immunoassay format. In this highly sensitive format, the light emission produced by appropriately labeled bound antibodies are quantitated automatically. Preferably, the reaction is performed using microtiter plates.

In a capture-antibody sandwich enzyme assay, the desired protein is bound between an antibody attached to a solid phase, preferably a polystyrene microtiter plate, and a labeled antibody. Preferably, the results are measured using a spectrophotometer, such as an ELISA plate reader.

In an alternative embodiment, a radioactive tracer is substituted for the enzyme mediated detection in an EIA to produce a radioimmunoassay (RIA).

In a sequential assay format, reagents are allowed to incubate with the capture antibody in a step wise fashion. The test sample is first incubated with the capture antibody. Following a wash step, an incubation with the labeled antibody occurs. In a simultaneous assay, the two incubation periods described in the sequential assay are combined. This eliminates one incubation period plus a wash step.

A dipstick/immunostick format is essentially an immunoassay except that the solid phase, instead of being a polystyrene microtiter plate, is a polystyrene paddle or dipstick. Reagents are the same and the format can either be simultaneous or sequential.

In a chromatographic strip test format, a capture antibody and a labeled antibody are dried onto a chromatographic strip, which is typically nitrocellulose or nylon of high porosity bonded to cellulose acetate. The capture antibody is usually spray dried as a line at one end of the strip. At this end there is an absorbent material that is in contact with the strip. At the other end of the strip the labeled antibody is deposited in a manner that prevents it from being absorbed into the membrane. Usually, the label attached to the antibody is a latex bead or colloidal gold. The assay may be initiated by applying the sample immediately in front of the labeled antibody.

Immunofiltration/immunoconcentration formats combine a large solid phase surface with directional flow of sample/reagents, which concentrates and accelerates the binding of antigen to antibody. In a preferred format, the test sample is preincubated with a labeled antibody then applied to a solid phase such as fiber filters or nitrocellulose membranes or the like. The solid phase can also be precoated with latex or glass beads coated with capture antibody. Detection of analyte is the same as standard immunoassay. The flow of sample/reagents can be modulated by either vacuum or the wicking action of an underlying absorbent material.

A threshold biosensor assay is a sensitive, instrumented assay amenable to screening large number of samples at low cost. In one embodiment, such an assay comprises the use of light addressable potentiometric sensors wherein the reaction involves the detection of a pH change due to binding of the desired protein by capture antibodies, bridging antibodies and urease-conjugated antibodies. Upon binding, a pH change is effected that is measurable by translation into electrical potential ($\mu$volts). The assay typically occurs in a very small reaction volume, and is very sensitive. Moreover, the reported detection limit of the assay is 1,000 molecules of urease per minute.

C. Other Assays

Transmembrane receptors are involved in many cellular communication process and have been the targets of numerous pharmacologic screening assays for the identification and development of new therapeutic agents. Many of these screening assays look for ligand induced changes in cell lines expressing the recombinant receptor. In some cases second messengers are assayed directly while in others, receptor is transfected into a cell line carrying a reporter gene construct whose expression level can be influenced (positively or negatively) by functional activation of the receptor. One common result of the stimulation of many different second messenger systems is transient changes in intracellular calcium homeostasis. this can be the result of Ca++ release from various intracellular compartments or from the influx of extracellular calcium.

Calcium transients offer a highly sensitive and selective method for characterization of AD4 gene function. Expression of recombinant AD4 in cell lines previously transfected with an aequorin reporter construct can be used to screen for and identify an AD4 ligand. Aequorin is a 21 kDa photoprotein that upon Ca++ binding undergoes an irreversible reaction with the production of light in the visible range. Because the fractional rate of aequorin consumption is proportional in the physiological [Ca++], it has been used for many years as a sensitive indicator of intracellular calcium. More recently, several different aequorin cDNA's have been engineered which allow selective targetting of aequorin expression to different intracellular compartments, including the cytoplasm, the nucleus and the endoplasmic reticulum. This allows for a variety of second messenger coupled pathways/compartments to be screened.

Therefore, within one embodiment a cell line which expresses mutant AD4 may be utilized in order to identify compounds which modify the mutant protein function in a way that mimics wild-type AD4 activity.

LABELS

AD4 proteins, nucleic acid molecules which encodes such proteins, anti-AD4 protein antibodies and agonists or antagonists, as described above and below, may be labeled with a variety of molecules, including for example, fluorescent molecules, toxins, and radionuclides. Representative examples of fluorescent molecules include fluorescein, Phycobili proteins, such as phycoerythrin, hodamine, Texas red and luciferase. Representative examples of toxins include ricin, abrin diphtheria toxin, cholera toxin, gelonin, pokeweed antiviral protein, tritin, Shigella toxin, and Pseudomonas exotoxin A. Representative examples of radionuclides include Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212 and Bi-212. In addition, the antibodies described above may also be labeled or conjugated to one partner of a ligand binding pair. Representative examples include avidin-biotin, and riboflavin-riboflavin binding protein.

Methods for conjugating or labeling the AD4 proteins, nucleic acid molecules which encodes such proteins, anti-AD4 protein antibodies and agonists or antagonists, as discussed above, with the representative labels set forth above may be readily accomplished by one of ordinary skill in the art (see Trichothecene Antibody Conjugate, U.S. Pat. No. 4,744,981,; Antibody Conjugate, U.S. Pat. No. 5,106,951; Fluorogenic Materials and Labeling Techniques, U.S. Pat. No. 4,018,884; Metal Radionuclide Labeled Proteins for Diagnosis and Therapy, U.S. Pat. No. 4,897,255; and Metal Radionuclide Chelating Compounds for Improved Chelation Kinetics, U.S. Pat. No. 4,988,496; see also Inman, *Methods In Enzymology*, Vol. 34, *Affinity Techniques, Enzyme Purification*: Part B, Jakoby and Wilchek (eds.), Academic Press, New York, p. 30, 1974; see also Wilchek and Bayer, "The Avidin-Biotin Complex in Bioanalytical Applications," *Anal. Biochem.* 171:1–32, 1988).

PHARMACEUTICAL COMPOSITIONS

As noted above, the present invention also provides a variety of pharmaceutical compositions, comprising one of the above-described AD4 proteins, nucleic acid molecules, vectors, antibodies, host cells, agonists or antagonists, along with a pharmaceutically or physiologically acceptable carrier, excipients or diluents. Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents.

In addition, the pharmaceutical compositions of the present invention may be prepared for administration by a variety of different routes, although intracranial routes are typically preferred. In addition, pharmaceutical compositions of the present invention may be placed within containers, along with packaging material which provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) which may be necessary to reconstitute the pharmaceutical composition.

METHODS OF TREATING OR PREVENTING ALZHEIMER DISEASE

The present invention also provides methods for treating or preventing Alzheimer Disease, comprising the step of administering to a patient a vector (e.g., expression vector, viral vector, or viral particle containing a vector) or nucleic acid molecules alone, as described above, thereby reducing the likelihood or delaying the onset of Alzheimer's Disease.

Similarly, therapeutic peptides, peptidomimetics, or small molecules may be used to delay onset of Alzheimer's disease, lessen symptoms, or halt or delay progression of the disease. Such therapeutics may be tested in a transgenic animal model that expresses mutant protein, wild-type and mutant protein, or in an in vitro assay system.

One such in vitro assay system measures the amount of amyloid protein produced. Briefly, by way of illustration, a cell expressing both AD4 gene product and amyloid is cultured in the presence of a candidate therapeutic molecule. The AD4 protein expressed by the cell may be either wild-type or mutant protein. In either case, the amount of amyloid protein that is produced is measured from cells incubated with or without (control) the candidate therapeutic. Briefly, by way of example, cells are labeled in medium containing $^{35}$S-methionine and incubated in the presence (or absence) of candidate therapeutic. Amyloid protein is detected in the culture supernatent by immunoprecipitation and SDS-PAGE electrophoresis or by ELISA. A statistically significant reduction of amyloid protein compared to the control signifies a therapeutic suitable for use in preventing or treating Alzheimer's disease.

Alternatively, transgenic animals expressing Alzheimer's disease protein may be used to test candidate therapeutics. Amyloid protein is measured or, if the animals exhibit other disease symptoms, such as memory or learning deprivation, an increase in memory or learning is measured. Memory and learning are tested in rodents by the Morris water maze (Stewart and Morris in *Behavioral Neuroscience*, R. Saghal, Ed. (IRLPress, 1993, p. 107) and the Y-maze (Brits et al., *Brain Res. Bull.* 6:71, 1981). Therapeutics are administered to animals prior to testing. The response time in trials are measured and an improvement in memory and learning is demonstrated by a statistically significant decrease in the timed trials.

As noted above, the present invention provides methods for treating or preventing Alzheimer's disease through the administration to a patient of a therapeutically effective amount of an antagonist or pharmaceutical composition as described herein. Such patients may be identified through clinical diagnosis based on symptoms of dementia or learning and memory loss which are not attributable to other causes. In addition, patients are also identified through diagnosis of brain atrophy as determined by magnetic resonance imaging.

Cognitive behavior in AD may be measured by any one of several tests (See Gershon et al., *Clinical Evaluation of Psychotropic Drugs: Principles and Guidelines*, Prien and Robinson (eds.), Raven Press, Ltd., New York, 1994, p. 467). One such test, BCRS, is designed to measure only cognitive functions: concentration, recent memory, past memory, orientation, functioning, and self-care. This test, as well as the Weschler Memory Scale and the Alzheimer's Disease-Associated Scale, may be used to determine improvement following therapeutic treatment. "Improvement" in Alzheimer's disease is present if there is a statistically significant difference in the direction of normality in the Weschler Memory Scale test. For example, test results of the performance of treated patients as are compared to members of the placebo group or between subsequent tests given to the same patient. Improvement within the present invention also encompasses a delay in the age of onset of Alzheimer's disease.

As will be evident to one of skill in the art, the amount and frequency of administration will depend, of course, on such factors as the nature and severity of the indication being treated, the desired response, the condition of the patient, and so forth. Typically, the compositions may be administered by a variety of techniques, although intra-cronial routes are often preferred.

Within other embodiments of the invention, the vectors which contain or express the nucleic acid molecules which encode the AD4 proteins described above, or even the nucleic acid molecules themselves may be administered by a variety of alternative techniques, including for example administration of asialoosomucoid (ASOR) conjugated with poly (L-lysine) DNA complexes (Cristano et al., *PNAS* 92122–92126, 1993), DNA linked to killed adenovirus (Curiel et al., *Hum. Gene Ther.* 3(2): 147–154, 1992), cytofectin-mediated introduction (DMRIE-DOPE, Vical, Calif.), direct DNA injection (Acsadi et al., *Nature* 352:815–818, 1991); DNA ligand (Wu et al., *J. of Biol. Chem.* 264:16985–16987, 1989); lipofection (Felgner et al., *Proc. Natl. Acad. Sci. USA* 84:7413–7417, 1989); liposomes (Pickering et al., *Circ.* 89(1): 13–21, 1994; and Wang et al., *PNAS* 84:7851–7855, 1987); microprojectile bombardment (Williams et al., *PNAS* 88:2726–2730, 1991); and direct delivery of nucleic acids which encode the AD4 protein itself either alone (Vile and Hart, *Cancer Res.* 53: 3860–3864, 1993), or utilizing PEG-nucleic acid complexes.

The following examples are offered by way of illustration, and not by way of limitation.

EXAMPLES

Example 1

Genetic Mapping of the AD Locus From the Volga German Kindred

The Volga German kindreds are a group of 7 related families with autosomal dominant early-onset Alzheimer's disease (AD). These families come from a group of Germans, who, in the 1760's, emigrated to the Volga river region of Russia. The VG remained culturally distinct from the surrounding Russian population and has apparently been genetically relatively isolated until this century. In 1987, Bird and collegues (Bird, et al., *Ann. Neurol.* 23:25–31, 1988) identified 5 VG kindreds with early-onset AD. Subsequently 2 additional early-onset VG families were identified (Bird, et al., *Ann. Neurol.* 25:12–25, 1989). In addition, other families with early-onset disease have been identified in which, similarly to the VG kindred, the APP gene and the chromosome 14 locus have been excluded as harboring the causative gene. These families include 4 Swedish families with a mean age-of-onset ranging from 55 to 64 and 2 Dutch families with mean onsets of 52 and 59 years. The 7 VG families are descendents of inhabitants of 3 adjacent villages from the Volga region of Russia. Although a common ancestor could not be traced, the unique ethnic origin coupled with 150 years of relative genetic isolation suggests that AD in these families is likely the result of a common genetic founder. Inheritance of AD in these kindreds appears to be autosomal dominant. Onset of AD in these families ranges from 40 to 81 years with family mean age-of-onsets ranging from 51 to 65 years (Bird et al., supra, Table 1). Numerous affected subjects in these families have been extensively characterized, both clinically and neuropathologically, and at least 1 affected subject from each family has had autopsy confirmation of the diagnosis of AD. Except for the relatively early age-of-onset, AD in the VG is clinically and pathologically indistinguishable from typical AD. Neurofibrillary tangles, A$\beta$ neuritic plaques, and other changes associated with AD have been observed in multiple autopsies.

TABLE 1

VG kindreds used for linkage analysis.

| Family | Affected (n) | Autopsied (n) | Affecteds sampled | Total subjects | Mean age of onset + SD, (n), range |
|---|---|---|---|---|---|
| H | 8 | 3 | 4 (2) | 4 | 59.5 + 3.9 (6) 56–68 |
| HB | 23 | 5† | 6 (2) | 30 | 60.8 + 7.1 (22) 54–75 |
| HD | 19 | 2 | 6 | 20 | 59.6 + 10.3 (17) 46–82 |
| KS | 14 | 3 | 8 (1) | 29 | 64.8 + 5.4 (13) 55–71 |
| R | 20 | 5 | 9 (3) | 37 | 50.2 + 7.3 (17) 40–67 |
| W | 4 | 2 | 2 | 4 | 59.2 + 10.5 (4) 48–79 |
| WFL | 6 | 2 | 2 | 15 | 63.8 + 7.6 (6) 55–76 |
| Totals | 94 | 22 | 37 (8) | 139 | 59.1 + 9.1 (86) 40–82 |

*Includes 1 unaffected subject autopsied.
†Numbers in parentheses indicates DNA samples obtained from autopsy material, either as paraffin blocks or frozen brain.

The locus responsible for AD in the VG kindreds has not been previously mapped genetically. Linkage analysis, as well as mutational analysis, of the VG families with chromosome 21 and chromosome 14 markers (AD3 locus and APOE locus) has yielded negative results. Moreover, the locus responsible for AD in the VG kindreds does not cosegregate with markers at the APP locus, and no mutations have been detected in the APP gene.

Linkage analysis was used to scan the genome for the locus causing AD in these VG families. DNA was prepared from lymphoblastoid cell lines from 139 individuals including 37 affected subjects. When suggestive evidence for linkage was found, autopsy-derived tissue, either frozen or embedded in paraffin, was used to prepare DNA from 8 additional affected subjects for whom no other tissue was available. Markers on all chromosomes were genotyped and analyzed using the lod score method (Morton, *Am. J. Hum. Genet.* 7:277, 1955; Hodge, et al., *Am. J. Hum. Genet.* 35:1139, 1983). For the genome screen, evidence for linkage was evaluated assuming autosomal dominant inheritance with age-dependent penetrance and a 0% sporadic rate. Lod scores were also computed using a low (1%) penetrance model, which makes no assumption about the disease status of at-risk individuals and thus serves as a check that information about linkage derives primarily from the affected individuals (in whom the genotype at the disease locus is more accurately known compared to that of at-risk subjects). Published marker allele frequencies (Genome Database) were used unless critical allele frequencies were significantly lower than those estimated in the VG. In this case, frequencies obtained from the VG pedigrees using all subjects (affecteds, at-risk and spouses) were used. This conservative approach was taken during screening since underestimation of the frequency of an allele co-segregating with the disease can cause false positive evidence for linkage (Ott, *Am. J. Hum. Genet.* 51:283, 1992). However, this approach will underestimate lod scores if the true allele frequency is lower than assumed. In this study, 162 publically available markers were genotyped. Among these were 70 STRP markers with heterozygosity values mostly >0.70 spaced ≧20 cM apart.

This work demonstrates the presence of a previously unmapped AD locus on chromosome 1 q31-42.

Initial suggestive lod scores for chromosome 1 were obtained for markers D1S103 ($Z_{max}$=1.79, θ=0.10) and D1S249 ($Z_{max}$=1.76, θ=0.20) (Table 2), which are separated by approximately 26 cM (FIG. 1). Subsequently, 21 other markers in this region spanning 55 cM were analyzed (Table 2). Using the conservative screening analysis conditions, significant evidence for linkage ($Z_{max}$≧3.0) was obtained with D1S479 ($Z_{max}$=4.40, θ0.11). This lod score was similar to that predicted by earlier power analyses. Most of the evidence for linkage comes from families HB and R, with positive lod scores also observed for families W, H, and HD (Table 3). Subsequently, a 112 bp allele of D1S479 co-segregated with the disease in 5 of 7 families, which is consistent with a common genetic founder. Other markers in the region also gave positive though non-significant lod scores (e.g. D1S439, $Z_{max}$=2.82, θ=0.17; D1S320, $Z_{max}$=1.87, θ=0.14; D1S103, $Z_{max}$=2.40, θ=0.008; Table 2).

Table 2 demonstrates that FAD is linked to chromosome 1 markers. Genotypes were performed by conventional methods, such as by PCR. All genotypes for D1S479 were determined in duplicate. For markers D1S227, D1S320, D1S213, D1S439, D1S479, D1S225, and D1S103, genotypes were determined for 8 samples from affected subjects either derived from either paraffin blocks or frozen brain material (not all samples amplified with all markers). Lod scores were computed using the computer program LIPED (Ott, *Am. J. Hum. Genet.*, 26:588, 1974) assuming age-dependent penetrance (Morton, *Am. J. Hum. Genet.*, 7:277, 1955).

TABLE 2

Lod scores for linkage of FAD to chromosome 1 markers*.

| Locus | Het.[†] | \multicolumn{7}{c}{Recombination fraction (θ)} | | | | | | |
|---|---|---|---|---|---|---|---|---|
| | | 0.001 | 0.05 | 0.10 | 0.15 | 0.20 | 0.30 | 0.40 |
| D1S238 | 0.86 | −9.29 | −1.99 | −0.34 | 0.42 | 0.76 | 0.81 | 0.43 |
| D1S422 | 0.76 | −7.25 | −1.70 | −0.28 | 0.38 | 0.67 | 0.65 | 0.27 |
| D1S412 | 0.71 | −7.82 | −1.66 | 0.18 | 1.00 | 1.31 | 1.17 | 0.54 |
| D1S306 | 0.61 | −14.71 | −7.75 | −4.69 | −2.88 | −1.71 | −0.43 | 0.01 |
| D1S310 | 0.57 | −6.03 | −1.75 | −0.79 | −0.31 | −0.06 | 0.14 | 0.11 |
| D1S249 | 0.87 | −9.76 | −1.12 | 0.65 | 1.44 | 1.76 | 1.60 | 0.81 |
| D1S245 | 0.82 | −12.15 | −2.56 | −0.42 | 0.58 | 1.05 | 1.11 | 0.55 |
| D1S205 | 0.80 | −11.66 | −3.39 | −1.45 | −0.48 | 0.04 | 0.38 | 0.20 |

TABLE 2-continued

Lod scores for linkage of FAD to chromosome 1 markers*.

| Locus | Het.[†] | 0.001 | 0.05 | 0.10 | 0.15 | 0.20 | 0.30 | 0.40 |
|---|---|---|---|---|---|---|---|---|
| D1S425 | 0.81 | −8.36 | −2.38 | −1.02 | −0.32 | 0.05 | 0.27 | 0.15 |
| D1S217 | 0.66 | −3.87 | −0.97 | −0.27 | 0.10 | 0.30 | 0.32 | 0.11 |
| D1S237 | 0.76 | −4.77 | −1.88 | −0.76 | −0.13 | 0.20 | 0.36 | 0.20 |
| D1S229 | 0.77 | −6.54 | −1.42 | −0.34 | 0.12 | 0.28 | 0.18 | −0.08 |
| D1S227 | 0.67 | −2.23 | 0.23 | 0.80 | 0.92 | 0.83 | 0.34 | −0.07 |
| D1S320 | 0.70 | −8.99 | −1.23 | 0.36 | 1.03 | 1.27 | 1.09 | 0.42 |
| D1S213 | 0.86 | −3.80 | −1.57 | −0.80 | −0.37 | −0.13 | 0.05 | 0.04 |
| D1S479 | 0.80 | −0.05 | 3.91 | 4.39 | 4.25 | 3.81 | 2.50 | 0.99 |
| D1S439 | 0.80 | −5.59 | 1.05 | 2.36 | 2.78 | 2.76 | 1.97 | 0.73 |
| D1S251 | 0.82 | −15.43 | −5.19 | −2.67 | −1.31 | −0.51 | 0.14 | 0.14 |
| D1S225 | 0.79 | −10.44 | −2.62 | −0.48 | 0.60 | 1.12 | 1.16 | 0.52 |
| D1S103 | 0.80 | 0.33 | 1.60 | 1.79 | 1.74 | 1.57 | 1.05 | 0.46 |
| D1S459 | 0.79 | −20.40 | −5.86 | −2.87 | −1.39 | −0.59 | 0.02 | 0.07 |
| D1S446 | 0.69 | −12.37 | −4.50 | −1.99 | −0.71 | −0.02 | 0.46 | 0.32 |
| D1S235 | 0.68 | −7.54 | −1.09 | 0.27 | 0.85 | 1.06 | 0.88 | 0.34 |

*Lod scores were computed using published allele frequencies except for D1S479. For this marker, the allele frequency for the 112 bp allele was derived from the VG subjects as a group, while frequencies for the other alleles were from published values (17).
[†]Het., heterozygosity.

In Table 3, the family lod score for linkage of AD to the marker D1S479 is presented. Conditions 1 and 2 are age-dependent penetrance with VG and CEPH allele frequencies respectively; conditions 3 and 4 are age-dependent penetrance with a sporadic correction function using VG and CEPH allele frequencies, respectively. For the H, HB, and R families, maximum lod score were obtained with D1 S479. For other families, maximum lod values were obtained with other markers (HD; D1S103, $Z_{max}$=1.75, θ=0.001, condition 4), D1S249 (KS; D1S412, $Z_{max}$=1.20, θ=0.10, condition 2), and D1S439/D1S227 (W; D1S227 and D1S439, $Z_{max}$=0.78, θ=0.001, condition 4). No marker was positive for the WFL family under any condition. Under the low (1%) penetrance model, $Z_{max}$ values were 3.04 (θ=0.10) and 1.27 (θ=0.15) for the control and VG allele frequencies, respectively.

TABLE 3

Family lod score for linkage of AD to D1S479.

| Family | Condition | 0.001 | 0.05 | 0.10 | 0.15 | 0.20 | 0.30 | 0.40 |
|---|---|---|---|---|---|---|---|---|
| H | 1 | 0.45 | 0.36 | 0.28 | 0.21 | 0.15 | 0.06 | 0.01 |
| | 2 | 0.44 | 0.36 | 0.28 | 0.21 | 0.15 | 0.06 | 0.01 |
| | 3 | 0.90 | 0.78 | 0.66 | 0.54 | 0.42 | 0.21 | 0.06 |
| | 4 | 0.90 | 0.78 | 0.66 | 0.54 | 0.42 | 0.21 | 0.05 |
| HB | 1 | 1.67 | 1.78 | 1.71 | 1.54 | 1.33 | 0.80 | 0.26 |
| | 2 | 1.60 | 1.72 | 1.64 | 1.49 | 1.27 | 0.76 | 0.25 |
| | 3 | 2.38 | 2.47 | 2.37 | 2.18 | 1.93 | 1.31 | 0.59 |
| | 4 | 2.31 | 2.40 | 2.30 | 2.12 | 1.87 | 1.27 | 0.57 |
| HD | 1 | −1.84 | −0.45 | −0.22 | −0.12 | −0.08 | −0.05 | −0.02 |
| | 2 | −0.32 | −0.13 | −0.05 | −0.02 | −0.02 | −0.03 | −0.02 |
| | 3 | −1.30 | 0.07 | 0.28 | 0.34 | 0.32 | 0.19 | 0.07 |
| | 4 | 0.22 | 0.40 | 0.45 | 0.44 | 0.38 | 0.21 | 0.07 |
| KS | 1 | −1.57 | −0.28 | −0.06 | 0.03 | 0.05 | 0.03 | 0.00 |
| | 2 | −1.40 | −0.26 | −0.05 | 0.03 | 0.05 | 0.03 | 0.00 |
| | 3 | −1.57 | −0.28 | −0.06 | 0.03 | 0.05 | 0.03 | 0.00 |
| | 4 | −1.40 | −0.26 | −0.05 | 0.03 | 0.05 | 0.03 | 0.00 |
| R | 1 | 1.07 | 2.32 | 2.49 | 2.40 | 2.19 | 1.55 | 0.70 |
| | 2 | 1.34 | 2.51 | 2.58 | 2.46 | 2.22 | 1.56 | 0.71 |
| | 3 | 1.46 | 2.69 | 2.84 | 2.73 | 2.48 | 1.76 | 0.83 |
| | 4 | 1.73 | 2.88 | 2.94 | 2.78 | 2.52 | 1.78 | 0.83 |
| W | 1 | 0.67 | 0.59 | 0.50 | 0.42 | 0.34 | 0.18 | 0.05 |
| | 2 | 0.67 | 0.59 | 0.50 | 0.42 | 0.34 | 0.18 | 0.05 |
| | 3 | 0.67 | 0.59 | 0.50 | 0.42 | 0.34 | 0.18 | 0.05 |
| | 4 | 0.67 | 0.59 | 0.50 | 0.42 | 0.34 | 0.18 | 0.05 |

TABLE 3-continued

Family lod score for linkage of AD to D1S479.

| Family | Condition | 0.001 | 0.05 | 0.10 | 0.15 | 0.20 | 0.30 | 0.40 |
|---|---|---|---|---|---|---|---|---|
| WFL | 1 | −0.50 | −0.41 | −0.32 | −0.24 | −0.17 | −0.07 | −0.02 |
|  | 2 | −0.50 | −0.41 | −0.32 | −0.24 | −0.17 | −0.07 | −0.02 |
|  | 3 | −0.49 | −0.40 | −0.31 | −0.24 | −0.17 | −0.07 | −0.02 |
|  | 4 | −0.49 | −0.40 | −0.31 | −0.24 | −0.17 | −0.07 | −0.02 |
| Totals | 1 | −0.05 | 3.91 | 4.39 | 4.25 | 3.81 | 2.50 | 0.99 |
|  | 2 | 2.05 | 5.92 | 6.29 | 5.99 | 5.37 | 3.61 | 1.57 |
|  | 3 | 1.83 | 4.37 | 4.60 | 4.34 | 3.85 | 2.50 | 0.99 |
|  | 4 | 3.94 | 6.39 | 6.49 | 6.09 | 5.41 | 3.60 | 1.56 |

In the VG pedigrees, genotypes are not available from many deceased individuals who are related to sampled subjects (e.g. all individuals in generations I–III in FIG. 2). Because of this missing data problem, marker allele frequencies can influence linkage analysis results. For most of the markers used, allele frequencies in the VG families were similar to those from controls. However, D1S479, in 5 of the families (H, HB, HD, R, and W), was substantially more frequent in the affected subjects (0.32 in affected subjects, 0.18 in all VG subjects,) compared to a frequency of 0.04 in controls. Such an increase in frequency for a closely linked marker allele is expected. When control frequencies based on VG unaffected spouses were used for the 112 bp D1S479 allele, the maximum lod score for D1S479 increased from $Z_{max}=4.40$ ($\theta=0.11$) to $Z_{max}=6.29$ ($\theta=0.10$) (Table 3).

Linkage analysis may be affected by the presence in the pedigrees of phenocopies (non-AD dementia cases or AD caused by something other than the major gene segregating in these families). Phenocopies can reduce the power to detect linkage and increase the estimated θ (Cavalli-Sforza and King, *Am. J. Hum. Genet.* 38:599, 1986). Phenocopies are a potential problem in the VG kindreds since the range of onset ages for AD in these families extends up to 82 years of age (Table 1), which overlaps with common late-onset AD. To correct for the presence of late-onset AD cases in the families, a phenocopy correction model was used (Schellenberg, et al., *Am J. Hum. Genet.* 53:619, 1993), which assumes that as the age-of-onset of a subject increases, the probability that the case is a phenocopy is increased. Despite the fact that in the absence of true phenocopies this model reduces the power to detect linkage, for all markers analyzed, the lod scores increased (Margaritte,et al., *Am. J. Hum. Genet.* 50:1231, 1992). For D1S479, $Z_{max}$ values increased from 6.29 to 6.51 and from 4.40 to 4.60 using the control and VG allele frequency for the 112 bp allele, respectively. Under this model, the maximum D1S479 lod score for a single family for D1S479 was 2.95 ($\theta=0.09$) for the R family. These results support the hypothesis that at least some of the AD cases in these families are probably phenocopies.

Figure 7:
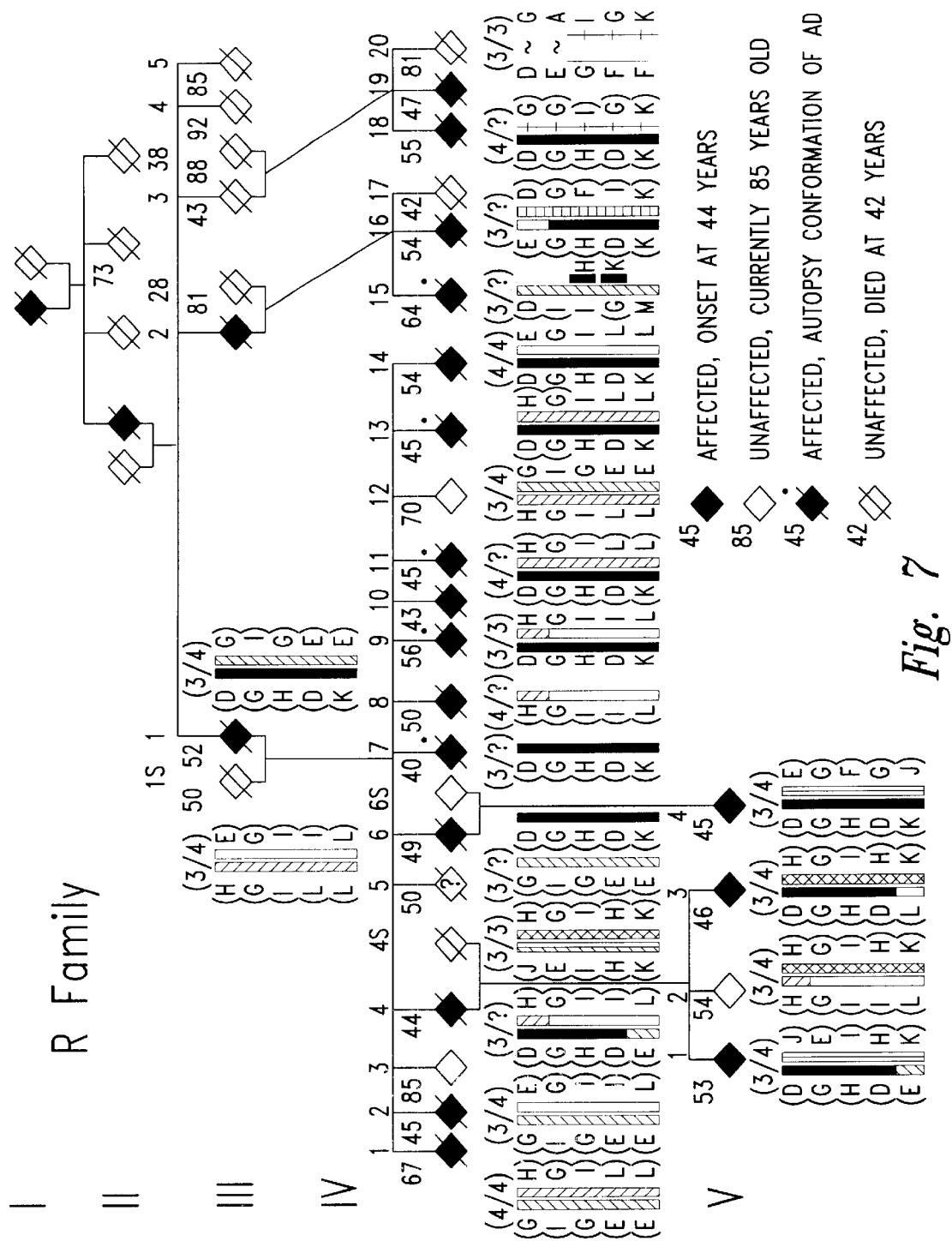
FIG. 7 depicts a family tree showing the segregation of chromosome 1 markers in the R family. The bars beneath each subject represent minimum recombinant haplotypes constructed using the 23 markers from D1S238 to D1S235 (Table 2). Alleles shown (from top to bottom) are for D1S249, D1S237, D1S479, D1S439 and D1S225, where A is the largest published allele. The solid bar represents the haplotypes segregating with the disease. Other haplotypes are represented by bars with different hatching or marking. A partially missing bar indicates markers not genotyped (subject IV-15). A " " symbol represents regions where the phase cannot be assigned. APOE genotypes are shown directly above the haplotypes with 3 and 4 being the $\epsilon$3 and $\epsilon$4 alleles, respectively. Recombinants were observed on the disease haplotypes between D1S479/D1S439 and D1S225 in subjects V-1 and V-3, and between D1S306 and D1S310 in subject IV-18 (not shown). In IV-16 there is a recombination between D1S217 and D1S237. A total of 4 recombinations (3 on non-disease related chromosomes) were observed between D1S249 and D1S237 in the 27 chromosomes in generation IV. The distance between these markers is 12 cM and the chance that up to 4 recombinants would be observed is 41%.

Haplotypes were constructed for the R family using the 23 markers spanning approximately 55 cM of chromosome 1 (FIG. 7). A common haplotype between D1S439/D1S479 and D1S306 was observed in all but 1 of the affected subjects (IV-1, FIG. 7). This individual did not share the disease haplotype across the entire region, had an age-of-onset of 67 years, which is greater than 2 SD above the family mean, and had an ∊4/∊4 genotype at the APOE locus. This APOE genotype is associated with lower age-of-onset for late-onset AD (Corder, et al., *Science* 261:921, 1993). Thus, this subject may be a phenocopy. In other families, definite assignment of a common disease haplotype was difficult because of missing data, and will require extensive multipoint analysis. However, for D1S479, the 112 bp allele segregated with he disease in the H, HB, HD, W, and R pedigrees. In the HD family, the 1 affected subject who did not have the 112 bp allele, had an age-of-onset of 75 years and was ∊3/∊4 at the APOE locus. However, age-of-onset alone could not be used to unambiguously determine whether a subject is a phenocopy. In the HB family, subjects with onsets of up to 75 years shared the D1S479 112 allele with other younger affected subjects. The KS family is the only VG kindred in which no affected subject had the D1S479 112 bp allele. Analysis of this family is complicated because of the late age-of-onset (64.8 years) and because of the 8 affected subjects, 3 were APOE ∊4/∊4 homozygotes (onset ages of 57, 58, and 67 years) and 4 were ∊4 heterozygotes (onset ages 67, 68, 68 and 71 years). Thus, the KS family could be an example of genetic heterogeneity within the VG kindreds, although group heterogeneity tests did not detect heterogeneity. In summary, the finding of the same rare allele segregating with AD in most of the VG pedigrees supports the hypothesis of a common genetic founder for most of the families. As described herein, the sequence data from VG patients confirms this hypothesis.

Taken together, these data demonstrate the presence of an AD locus at 1q31-42. Analysis of recombinants in the R family define the candidate region as between D1S225 (subjects VI-3 and V-3 in FIG. 2) and D1S217 (subject IV-16), a region spanning 14 cM (FIG. 8).

Example 2

Cloning of the AD4 Gene From Chromosome 1 Using YACS

YAC clones derived from chromosome 1 were obtained from the CEPH-Genethon library and were identified for the region spanning D1S229 to D1S103 by 2 different methods.

In the first method, the CEPH-Genethon YAC library was arrayed for PCR-based screening. This publically available library (Bellanne-Chantelot, et al., *Cell* 70, 1059–1068, 1992) was obtained from Glen Evans (Salk Institute) as 21,792 clones in 227 96-well plates. For DNA preparation, colonies were grown separately in 1.5 ml liquid media, harvested, and pooled. Spheroplasts were made by digestion with lyticase. DNA was purified by phenol/chloroform/isoamyl alcohol extractions and precipitated by the addition of sodium acetate and ethanol. After resuspension and RNase treatment, the DNA was ready for PCR amplification.

A two-dimensional YAC pooling scheme allowed the identification of specific YAC addresses by PCR screening (Amemiya, et al., *Nucl. Acids. Res.* 20:2559–2563, 1992). The library was subdivided into five sets (4×48 and 1×35 trays). Duplicates were made of each set. One replica of each of the 5 sets was used for the first dimension basic horizontal pools (each pool represents all clones from a single 96-well plate). The second replica was used for second dimension basic vertical pools (pools containing clones from a specific well position such as A1 for plates from a set). The pools within each set were further combined to facilitate PCR screening. For each set, horizontal pools were combined to generated to 4 super-horizontal pools. Each super-horizontal pool contained clones from 12 consecutive plates (plates 1–12, 13–24, 25–36, 37–48). The second dimension was combined to produce 8 super-vertical pools per set. Each super vertical pool contained clones from each row in a set (A, B, C, . . . etc.). Hence the entire library was reduced to 19 super horizontal pools (4×4 sets +3×1 set), and 40 super vertical pools (8×5 sets). In this way, candidate clones can be found after two rounds of PCR i.e. a first round with super pools and a second round with the basic pools. When multiple hits occur, a final round of PCR is necessary.

The YAC library was screened using primers for the STS D1S320 and D1S479 as shown in FIG. 9. (SEQ. ID NOS:9 and 12) This screening yielded the following YACs: 920e7, 859b6, 904f3.

In the second method, a data base was queried. The CEPH-Genethon INFO clone data base contains information concerning the genetic marker and STS content of YACs in the CEPH-Genethone YAC library. This database was queried with the following markers: D1S229, D1S227, D1S213, D1S479, D1S439, D1S225, D1S103, D1S495. The YACs identified were 857h3, 934f2, 957g10, 881b8, 913e10, 810e5, 921d12, 865c8, 920e7, 859b6, 736b6, 746d7, 748h9, 748e2, 753a5, 753d8, 753d9, 753f9, 753f12, 753h3, 757d8, 759b10, 757f9, 761h10, 767b1, 767d, 767g1, 769f11, 786a8, 786f11, 820g5, 824g8, 824g9, 824g11, 826b3, 826b5, 831e4, 849a7, 856a7, 880d12, 897f9, 899f1, 899h1, 920g1, 904f3, 915e8, 922a10, 933a8, 958e10, 978g10, and 979f3. Some of these YACs contain the marker used in the query and some are connected to YACs which contain the marker used in the database query. A total of 60 YACs were identified by the combined methods.

YAC DNA was prepared from each YAC clone. The YAC DNA was then amplified using the primers shown in FIG. 9. (SEQ ID NOS:4–12) A YAC contig map partially covering the region from D1S229 to D1S103 was constructed.

EST T03796 (FIG. 10), SEQ ID NO:14 was identified in the EST GenBank database as a sequence with homology to the chromosome 14 AD gene clones both at the nucleotide level and the amino acid level. Oligonucleotide primers, EP1F and EP1R, and KM7749 and KM7750 were used for PCR amplification (FIG. 11). SEQ ID NOS:19, 20, 32, 33 Given the EST sequence, the expected size was approximately 140 bp (for primers EP1F and EP1R) or 190 bp (for primers KM7749 and KM7750). When human genomic DNA was amplified, a 1,300 bp band was observed. Amplification of the YACs from the chromosome 1 Volga German gene region with the same primers yielded a 2.5 kb fragment from four different isolates of YAC 921d12. One isolate of 921d12 did not yield this fragment, but it was smaller and presumably deleted for the 2.5 kb fragment. YAC 921d12 has been previously shown to contain the markers D1S439 and D1S479.

In addition, a panel of rodent-human hybrid cell lines obtained from the Coriell Institute for Medical Research were also amplified with the same primers. These cell lines contain one or a few human chromosomes on a rodent background (either mouse or hamster). Only cells containing human chromosome 1 had the 2.5 kb band.

DNA from YAC 921d12 was amplified with primers EP1F and EP1R and subsequently with WWF and WWR (FIG. 11) SEQ ID NOS:19, 20, 17 and 18 to produce a 2.5 kb fragment. DNA sequence analysis of this 2.5 kb fragment was performed with primers WWF and WWF1L FIG. 11; SEQ ID NOS:17 and 21 to give sequence ELL1.1; (FIG. 10) SEQ ID NO:15 this sequence contained at its 5' end a portion of the EST T03796. This 2.5 kb fragment was also sequenced with primers WWR and WWR1R (SEQ ID NOS:18 and 22) yielding the sequence ELL1.2, (SEQ ID NO:16) which also contained a part of the DNA sequence from T03796. The 2.5 kb band from YAC 921d12 was reamplified, purified and sequenced using the primers: WWF, WWF1L, WWR and WWR1R. (SEQ ID NOS:17, 21, 18 and 22 respectively) The sequence of these DNA molecules is shown in FIG. 10. (SEQ ID NOS:13 to 16) In this fragment, 119 bp on the 5' and 69 bp on the 3' end were identical to the EST sequence. In addition, a splice acceptor and donor sequence were observed at both junctions of the EST sequence, suggesting that the intervening sequence is an intron of the chromosome 1 gene. Thus, EST T03796 is on YAC 921D12, and is a candidate for containing at least part of the Volga German AD gene.

cDNAs encoding the AD gene were isolated as follows. One million clones from a Werner syndrome fibroblast cDNA library or B616 human brain cDNA library were plated and transferred to Duralon membranes (Stratagene). The filters were pre-hybridized for one half hour in Church-Gilbert Hybridization solution (0.5M Na phosphate, pH7.0, 7% (w/v)SDS, 1% (w/v)BSA) at 65° C. and screened using 500,000 cpm/ml of a 140 base pair PCR product amplified from the EP1 primers (140 bp of the EST T03796) or a 190 bp PCR product amplified from KM7749 and KM7750 primers. Probe was labeled using a random primed method (Boehringer-Mannheim) for half an hour and unincorporated nucleotides were removed by a Microspin s-200 HR column (Pharmacia). The filters were hybridized for 16 hours and then washed 15 minutes each at 65° C. in 2×SSC/0.1% SDS followed by a wash in 0.1×SSC/0.1% SDS. Autoradiographs were exposed for 16 hours and four primary candidates from the fibroblast library and five primaries from the brain library were isolated. The primary candidates were positive upon rescreening. Secondary positives were picked into SM buffer and rescued using published protocols (Stratagene).

In addition, 600,000 clones in an arrayed version (Munroe,et al., *Proc. Natl. Acad. Sci USA* 92:2209–2213, 1995) of the above fibroblast cDNA library were screened using PCR methods. The EP1 and WW1 primer pairs were used to screen the plate pools (1–48). The EP1 primer pair gave positives in plates 11, 17 and 36, while the WW1 primers gave positives in plates 17 and 36. When PCR was done to determine column and row addresses only two addresses could be determined: plate 17 C7 (both primer pairs) and 17 C11 (WW1 only). Confirmatory PCR on the individual wells showed product for only 17C11. Both wells were plated for tertiary screening to obtain plaque purified phage. The EP1 PCR product was used for screening as above; positive plaques were isolated for 17 C11 and were rescued as above. Positive plaques eventually purified were designated 11, 15A, 15B, and C11, PS2-6, PS2-10, and PS2-41.

The sequence from chromosome 1 was then used to screen several cDNA libraries. Positive clones 2.2 kb in length were isolated and sequenced. The sequence, shown in FIG. 1, (SEQ ID NO:1) shows clear overlap with the ends of the PCR fragment. Additional EST sequences with overlapping sequence, and additional cDNA sequences were obtained by further library screening.

Example 3

Mutations in Affected VG Patients

Using RT-PCR, the entire gene has been amplified from both affected VG individuals and unaffected individuals. The unaffected individuals are from VG families and from unrelated lineages. The sequences obtained have been analyzed. In affected individuals, there is a nucleotide change in codon 141 (AAC→ATC) resulting in an amino acid alteration from asparagine to isoleucine (N141I). No such change was found in any unaffected individuals of comparable age. The amino acid sequence in the region of the alteration is LLNSVLNTLIMISVIVVMTI (SEQ ID NO:41) in the unaffected and LLNSVLITLIMISVIVVMTI (SEQ ID NO:42) in the affected individuals examined. Affected subjects carrying the N141I mutation were identified in 5 (H, HB, HD, R, W) of the 7 VG families initially screened. ALL subjects with the N141I mutation also carried the D1S479 112 bp allele (allele H, FIG. 7). Subsequently, 2 additional VG families (E and BE) were screened for the N141I mutation. In both kindreds, the affected subjects carried. the N141I mutation and the D1S479 112 bp allele. In total, the N141I mutation was directly observed in 20 affected subjects and inferred to be present from spouse/children genotypes in an additional 6 AD subjects; onset ages for the 26 subjects ranged from 44 to 75 years. The N141I mutation was also observed in 15 at-risk subjects (blood relatives of affected N141I carriers) with ages ranging from 23 to 67 years. No VG spouse (n=17) had the N141I mutation. Additional populations screened included 84 normal Caucasians, spouses, at-risk subjects and affected subjects from 67 late-onset familial FAD families (n=223 affected subjects), and 48 affected sporadic subjects from an AD clinic population.

In addition to the N 141I mutation, three other variants were identified at nucleotide 436 (C→T, subject HB), 496 (C→T, subjects HD and W) and 628 (C→T, subjects HD and W). These variants did not change the amino acid encoded at these sites (alanine, asparagine, and histidine, respectively).

Example 4

Characterization of the AD4 Gene and its Protein Product

The sequence of the VG from chromosome 1 was constructed from sequence of several clones as described. The sequence is shown in FIG. 1. (SEQ ID NO:1) The amino acid sequence deduced from this DNA sequence is shown in FIG. 2. (SEQ ID NO:2) Comparison of this sequence with the sequence of the AD3 gene (SEQ ID NO:3) from chromosome 14 shows sequence homology. An alignment of the proteins and genes as constructed using the program GAP from the Wisconsin package of sequence analysis software (Ver. 8.0.1—UNIX, September 1994) is shown in FIG. 3. The amino acid sequence of AD4 exhibits approximately 67% identity to the AD3 gene product. Some notable characteristics of the AD4 gene product are shown in FIG. 5.

The protein encoded by the chromosome 1 AD gene is a membrane protein, as judged by the seven hydophobic segments presumed to be membrane spanning regions (FIG. 4). The AD4 protein is also referred to as STM2. For STM2, all the putative transmembrane helices are capped at the carboxyl-terminal end by a lysine residue, found either at the very end or within a few residues of the end of the transmembrane domains. The N141I mutation, a change from a hydrophilic asparagine residue to a hydrophobic isoleucine residue, is at a position directly adjacent to the first predicted transmembrane domain.

A northern blot (Clontech) containing 2 μg of human poly A-plus mRNA derived from heart brain placenta, lung, liver, skeletal muscle, and pancreas was hybridized with the 2.3 kb AD4 cDNA clone as a probe. Hybridization was performed in 0.75M NaCl, 0.05M $NaH_2PO_4$, 5 mM $Na_2EDTA$, 10×Denhardt's solution, 100 microgram/ml salmon sperm DNA, 50% formamide, 2% SDS at 42° C. for 18 hours. Filters were washed with 0.1×SSC, 0.1% SDS at 65° C. Northern blot analysis of RNA from a variety of human tissues revealed two AD4-related transcripts which were approximately 2.4 and 2.8 kb in size. The larger transcript appears to be primarily expressed in placenta, skeletal muscle and heart, while the smaller transcript is detected in heart, brain, placenta, liver, skeletal muscle and kidney but not lung. A sequence-tagged site (STS) from the 3' untranslated region was used to confirm that AD4 maps to chromosome 1 and to YAC 921d12. The two transcripts observed are possibly the result of alternative polyadenylation since two putative polyadenylation signals were identified in the 3' untranslated region, at nucleotides 1834 and 2309. The message sizes for STM2 from Northern blot analysis (2.4 and 2.8 kb) are slightly larger than the 2.3 kb size predicted from the full-length DNA sequence and the 1.8 kb size predicted by the second polyadenylation site observed in the sequence. This apparent discrepancy may be due to the anomalous migration of size markers which has been previously observed with this type of Northern blot.

The normal cellular function of STM2 is unknown. If this protein is functionally similar to spe4, the *C. elegans* gene with sequence similarity to STM2, it may play a role in the cytoplasmic partitioning of proteins. Mutations in STM2 could alter intracellular protein trafficking of APP and ultimately lead to altered APP processing and increased production of Aβ1-40 or Aβ1-42 (amyloid β protein). Consistent with this notion, recent work with fibroblast cell lines from AD3 carriers has shown that secretion of Aβ ending at position 42 is increased relative to non-carrier cell lines. Alternatively, STM2 may function as a G-protein coupled receptor or as an ion channel.

Example 5

Cloning of AD Gene on Chromosome 1

The gene may be obtained from genomic or cDNA libraries or from genomic DNA or mRNA. The nucleotide sequence of the gene provided herein may be used to design oligonucleotides. The primers are optimally 18–25 nucleotides in length and preferably contain not more than 50% AT base pairs, do not end in A, and should not have self-complementary regions.

The oligonucleotides may be used as hybridization probes on cDNA or genomic libraries. For cDNA libraries, mRNA from a specific source, such as a cell line or tissue sample, is transcribed into cDNA and inserted into an appropriate vector (e.g., λgt10, λZAP, pBS, or pSPORT). (see Sambrook et al., Molecular Cloning, Cold Spring Harbor, 1989). The recombinant vector is introduced into an appropriate bacterial strain (e.g., DH5a or KW257) and the cells plated on growth medium. Alternatively, cDNA libraries representing RNA from various sources are obtained commercially (e.g., Clontech Laboratories). In either case, colonies (for plasmids) or plaques (for phage) are transferred to a nitrocellulose or nylon membrane and prepared for hybridization (Sambrook, supra). Oligonucleotide probes are labeled at their 5' end with $^{32}P$ using T4 polynucleotide kinase. Hybridization and washes are performed under standard conditions for the length and GC content of the probe (see Sambrook et al., supra).

For isolation of genomic clones containing the AD4 gene, genomic libraries are constructed by standard methods (Sambrook et al., supra) or obtained from commercial sources (Clontech, Stratagene, Research Genetics and Genome Systems). Libraries are constructed in phage, cosmids, P1, BACs, or YACs and probed as described for cDNA libraries. Colonies or phages that hybridize are picked, purified and grown for preparation of DNA.

If a full-length sequence is not obtained by the cloning and screening methods described, full-length sequences may be obtained by screening additional clones, by RACE (Frohman and Martin, *Proc. Natl. Acad. Sci. USA*

85:8998–9002, 1988), ligation-anchored PCR (Troutt et al., *Proc. Natl. Acad. Sci. USA* 89:9823–9825, 1992) or other similar methods. Verification that a clone contains AD4 sequence may be obtained by determining the DNA sequence of the clone and comparing it to the sequence of AD4 provided herein. Sequence identity of 90% or better indicates that the clone encodes AD4. Some mismatch may be due to polymorphisms or DNA sequence errors.

Example 6

Detection of Mutations

Mutations in the AD4 gene may be determined by nucleotide sequence analysis. Peripheral blood cells are obtained from patients by venipuncture and hypotonic lysis of erythrocytes. DNA or mRNA is isolated from these cells and the AD4 gene isolated by amplification. Oligonucleotide primers are chosen based on the cDNA sequence provided herein or genomic sequence. A computer program such as Primer 2.2, which is publically available from the web-server at the Whitehead/MIT Center for Genome Research, assists in choosing oligonucleotide primers. If mRNA is used as a source of nucleic acids, first strand cDNA if synthesized by standard methods. Amplification of DNA is performed and the DNA sequence of the PCR product is determined. A comparison of the sequence obtained from the patient and from a normal control allows identification of mutations.

In addition, the N141I mutation in AD4 gene creates a Sau3A I restriction site, which may be used to rapidly screen for mutant alleles. Genomic DNA or cDNA may be directly screened for the Sau3A I restriction site or amplified by PCR using primers which flank the 141 codon. DNA or amplified DNA is restricted with Sau3A I and electrophoresed in an appropriate percentage agarose gel. The presence of the Sau3A I site is detected by ethidium bromide fluorescence for amplified products or by probe hybridization following transfer of the gel to nylon membrane. Suitable probes are oligonucleotides or DNA fragments containing sequence near or encompassing the 141 codon. Preferably, in the case of an oligonucleotide probe, there is at least 24 bases that do not span codon 141.

Figure 12:
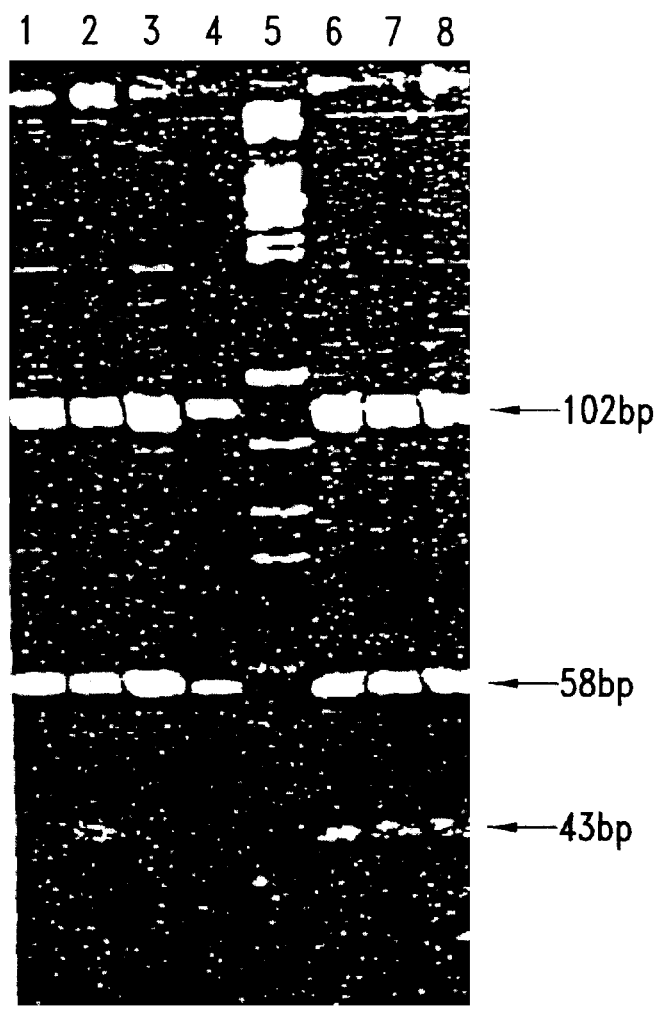
FIG. 12 presents an ethidium bromide stained gel of genomic DNA amplified with WWF and INTIR primers. Lanes are: 1, at-risk, 79 years; 2, affected, onset 60 years; 3, at-risk, 67 years of age; 4, affected, onset 75 years (presumed phenocopy); 5, Boehringer Mannheim DNA size standard V.

As shown in FIG. 12, the N141I mutation is detectable after amplification. Approximately 60–100 ng of genomic DNA was amplified with primers WWF and INTIR (intronic primer 5'-GTGGGGCAGACGGAGAGAA-3') at 40 ng (SEQ ID NO:43) each, 1.5 mM MgCl$_2$ and 200 µMdNTPs. Amplification was performed with an initial incubation at 95° C. for 3 min. followed by 35 cycles of 45 sec. at 94° C., 45 sec. at 60° C., and 45 sec. at 72° C., with a final incubation for 10 min, at 72°. The 160 bp PCR product (in 20 ul) was digested with 10 U Sau3A and the fragments resolved by electrophoresis in a non-denaturing 12% polyacrylamide gel. Fragments were visualized by ethidium bromide staining. The N141I mutation results in fragments of 102 bp, 58 bp, 43 bp and 15 bp (not shown) while non-carriers have only the 102 and 58 bp fragments. Lanes are: 1, at-risk, 79 years; 2, affected, onset 60 years; 3, at-risk, 67 years of age; 4, affected, onset 75 years (presumed phenocopy); 5, Boehringer Mannheim DNA size standard V; 6, affected, onset at 52 years; 7, affected, onset 46 years; 8, affected, onset 49 years.

Example 7

Determination of the DNA Sequence of the AD4 Genomic Region

A 2.5 kb fragment of DNA from the AD4 gene was amplified from YAC 921d12 DNA using primers WWF and WWR and radioactively labeled by nick-translation (Sambrook, et al. supra). A human genomic clone hybridizing to this fragment was identified in a commercially available library (Genome Systems P1 library). The hybridization was carried out according to the manufacturers instructions. PCR amplification using primers specific for the 5' and 3' ends of the AD4 cDNA confirmed that the P1 clone (clone #6004 in the nomenclature of Genome Systems) carried the entire AD4 gene.

DNA from P1 clone 6004 was sheared and subcloned into M13mp18 vector prepared by digestion with SmaI and dephosphorylation. The vector was purchased from Novagen (Catalog #69996-1) and the fragments were cloned according to the manufacturers instructions. Approximately 1600 clones were isolated. The sequence of the insert was determined by fluorescent detection on an ABI373A according to the manufacturers instructions. The data was assembled using the program Xgap (Staden, R. (1994) The Staden package, In "Methods in molecular biology" A. M. Griffin and H. G. Griffin, Eds., Vol 25, pp. 9–170, Humana Press). Exons were identified by entering the cDNA sequence into the assembly.

The sequences of the 12 exons and the flanking intron sequence of the AD4 gene are shown in FIGS. 13 to 19. (SEQ ID NOS:34 to 40) The relative positions of the exons in these sequences are listed in Table 4.

TABLE 4

Position of exons in the genomic sequence

| Exon | Genomic sequence | Exon position | Exon length |
|---|---|---|---|
| exon1 | stm.genA | 546 | 143 |
| exon2 | stm.genB | 850 | 186 |
| exon3 | stm.genC | 327 | 161 |
| exon4 | stm.genC | 2140 | 215 |
| exon5 | stm.genD | 168 | 142 |
| exon6 | stm.genE | 808 | 68 |
| exon7 | stm.genE | 1555 | 221 |
| exon8 | stm.genF | 102 | 99 |
| exon9 | stm.genF | 1345 | 84 |
| exon10 | stm.genF | 1809 | 102 |
| exon11 | stm.genG | 1053 | 117 |
| exon12 | stm.genG | 2470 | 683 |

Example 8

Isolation of the Gene From Patient DNA and Detection of Polymorphisms

Treatment of Alzheimer's disease is more effective if begun prior to the onset of neural degeneration. However, current diagnostics only effectively identify patients after substantial loss of cognitive function. Basically, loss of cognitive function in an older patient without any detectable cause is the primary indicator of Alzheimer's disease. Strict confirmation of the diagnosis is made by autopsy. Any treatment which blocks the initiation or progression of Alzheimer's disease will be much more effective if an earlier diagnosis is made.

One dominant mutation of the AD4 gene is known to cause early-onset Alzheimer's disease. Other mutations in this gene or in other members of the same gene family may cause or contribute to Alzheimer's disease. We provide herein methods for detection of mutations in the AD4 gene. The same techniques will allow detection of mutations in other members of the gene family.

Ten pairs of oligonucleotide primers used to PCR amplify ten fragments carrying the 12 AD4 exons are listed in Table 5. DNA is isolated from patient blood samples and individual PCR reactions carried out with each set of primers using the Perkin-Elmer PCR kit according to the manufacturers instructions in a Perkin-Elmer 9600 PCR machine with the following cycle conditions: 2 minutes at 92° C., 35 cycles of 20 seconds at 92° C., 45 seconds at the indicated annealing temperature, and 3 minutes at 72° C., followed by 7 minutes at 72° C. PCR fragments are purified by gel filtration in a 96-well format spin column with Sephracyl-500HR resin (Wang, Gan Boysen and Hood, *Anal. Biochem.* 226: 85–90, 1995). Mutations are detected by fluorescent dye terminator sequencing on the ABI373A using the sequencing primers specific for each exon as listed in Table 6. Many other mutation detection formats are possible using the PCR amplified fragments.

A diagnostic test will have several uses in addition to the eventual use of targeting patients for early intervention with Alzheimer's drugs. First, clinical trials of any Alzheimer's drug would benefit from monitoring the allelic variations in genes which predispose towards the disease. The genetic background of the patients may be correlated with different mechanisms for initiation of the disease: a drug which is effective against one disease mechanism may not be effective against disease caused by other mechanisms. Second, the diagnostics may be used to choose the appropriate treatments if clinical trials show that different genetic backgrounds are correlated with the efficacy of drugs.

TABLE 5

Primers for PCR of exon fragments

| Exons amplified[a] | Primer | (SEQ ID) | Sequence (5'–3') | PCR product size[b] | PCR conditions MgCl$_2$ (mM) | Annealing temperature (° C.) |
|---|---|---|---|---|---|---|
| 1 | INT105L | (SEQ ID NO: 57) | GGCGTTTTGTTCTTCTTCTCTC | 956 | 1.0 | 60 |
|   | INT106R | (SEQ ID NO: 58) | ACCAAAGGGTACAGAGTTTTCCC |   |   |   |
| 2 | INT108L | (SEQ ID NO: 59) | CATCCCCAAGTGGTATGTGTTA | 610 | 1.0 | 60 |
|   | INT107R | (SEQ ID NO: 60) | CTCCCCAGCCGTGCTTGTG |   |   |   |
| 3 | INT111L | (SEQ ID NO: 61) | CGTTTGATTGACAGGCATCTCT | 549 | 1.0 | 61 |
|   | INT112R | (SEQ ID NO: 62) | CAAGGTGGCAGAGTGGACAG |   |   |   |
| 4 | INT115L | (SEQ ID NO: 63) | CATATGCCCTAGTAGCTCATAG | 596 | 0.75 | 56 |
|   | INT116R | (SEQ ID NO: 64) | CCATTATACGAACAAGGAAGCTG |   |   |   |
| 5 | INT113L | (SEQ ID NO: 65) | GCTCATGGGGATGGTGCCC | 1149 | 1.0 | 60 |
|   | INT114R | (SEQ ID NO: 66) | GAAGCCGCTGTCTAAAAGCTTAT |   |   |   |
| 6, 7 | INT102L | (SEQ ID NO: 67) | CCCTCCCAGCGTAGGCATGAA | 1200 | 2.0 | 62 |
|   | INT101R | (SEQ ID NO: 68) | GCAGAAAGGGATGCAAGCCC |   |   |   |
| 8 | INT103L | (SEQ ID NO: 69) | GGCATGCTCTGAGAGCTCCA | 572 | 1.0 | 60 |
|   | INT109R | (SEQ ID NO: 70) | GCCCAGAAGCTCCTTGCTCC |   |   |   |
| 9, 10 | INT110L | (SEQ ID NO: 71) | TGGACCCCTCCCACAACGG | 868 | 1.0 | 60 |
|   | INT104R | (SEQ ID NO: 72) | TCACAGAGATGCCTCTGATGG |   |   |   |
| 11 | INT117L | (SEQ ID NO: 73) | ACTGGTTTTACCTGAGTTTCAGA | 568 | 1.0 | 58 |
|   | INT118R | (SEQ ID NO: 74) | CGAGCACACCTCCTGTGAG |   |   |   |
| 12, 3' UTR | INT7L | (SEQ ID NO: 75) | GGTGTCTAGCACCGTTATCC | 803 | 2.0 | 60 |
|   | DMO1009 | (SEQ ID NO: 76) | ACAGGACTCATCTATTTATGGATA |   |   |   |

TABLE 6

Primers for sequencing exons from PCR templates

| Exon | Primer sequence | Primer Position | SEQ ID |
|---|---|---|---|
| Exon 1 | AACACCGTTCATACCTT | 808 | (SEQ ID NO: 44) |
| Exon 2 | CAATTGTCTGGGTATCA | 800 | (SEQ ID NO: 45) |
| Exon 3 | CTTTGTCTCACAGGAAA | 266 | (SEQ ID NO: 46) |
| Exon 4 | CGTGCATTACATGGATA | 2062 | (SEQ ID NO: 47) |
| Exon 5 | GTCCAGAATCACTCAAG | 79 | (SEQ ID NO: 48) |
| Exon 6 | ATCAGTCTCAGGATCCT | 719 | (SEQ ID NO: 49) |
| Exon 7 | GCTGACTGTCTGGAACT | 1584 | (SEQ ID NO: 50) |
| Exon 8 | CCAGTCAACTCTGAAAG | 288 | (SEQ ID NO: 51) |
| Exon 9 | CTTGCTCAATCTTCAAG | 1582 | (SEQ ID NO: 52) |
| Exon 10 | CCTGGTAACACTCTGAC | 1708 | (SEQ ID NO: 53) |
| Exon 11 | TCCACATCTTAGCTTCTAG | 912 | (SEQ ID NO: 54) |
| Exon 12, 5' | CTAGACCATGACTCACAG | 2397 | (SEQ ID NO: 55) |
| Exon 12, 3' | AGAGGGGTCAACATTTAC | 3179 | (SEQ ID NO: 56) |

Example 9

Expression of STM2

The expression pattern of STM2 was examined in multiple tissues by Northern blot analysis (FIG. 20). A probe was generated by amplifying the STM2 cDNA clone using primers ADC22R2 and ADC22L5. Identical patterns were obtained with probes made using primer pairs DMO1018 and DMO1021 or DMO1009 and DMO1014. A 2.4 kb message corresponding to STM2 was observed in all tissues examined, including all regions of brain sampled. (In kidney, liver and lung, longer exposures of the same Northern blot showed STM2 to be present at low levels in these tissues; data not shown). High expression levels were observed in the pancreas, heart, and skeletal muscle. In these three tissues, a second 2.8 kb transcript was observed. From the STM2 cDNA sequence, two potential polyadenylation signals were identified at nucleotides 1834 and 2309 (total clone length, 2167 bp). To determine whether the 2.4 and 2.8 kb transcripts could represent different length 3' UTR polyadenylation variants, RNA blots were hybridized with a probe scanning the entire 3' UTR and with a probe starting after the first polyadenylation site. Both probes gave identical patterns, indicating that only the second polyadenylation site was used.

In an attempt to identify[] homologues of STM2, liver and pancreas cDNA was amplified with degenerate primers based on the STM2 sequence. Twenty-two M13 recombinant clones were identified and sequenced, all corresponding to STM2. Seven of the 22 clones had the sequence GAGATGGAAGAC (SEQ ID NO:77) beginning at nucleotide 1327 in the cDNA sequence, which is 3 bp shorter than the previously reported sequence (AGATGG|AAGAAGAC, where "|" indicates the junction between exons 9 and 10). (SEQ ID NO:78) The shorter transcript encodes a predicted protein one amino acid shorter (EMED) (SEQ ID NO:87) versus EMEED) (SEQ ID NO:88) with no frameshift. The shorter transcript is likely a result of alternative splicing of exon 10, with the first coding AG dinucleotide used as the splice acceptor sequence or a polymorphism. To distinguish between these possibilities, RNA and DNA were prepared from a lymphoblastoid cell line from a normal (non-AD) VG subject in the HD family. Both transcripts were present in RT-PCR products using primers EX103L and EX102R from exons 9 and 10. However, when the intron 9 to exon 10 region of genomic DNA from the same subject was sequenced, a single sequence that corresponds to the genomic sequence was obtained. Thus the two different transcripts arise from alternative splicing. Both transcripts were also observed in leukocytes, skeletal muscle, and one fetal brain library (Clontech), with the longer transcript being more abundant. However, in another fetal brain library (Stratagene), only the longer transcript was observed, while in a foreskin fibroblast library, only the shorter transcript was found.

TABLE 7

Primers for RNA analysis

| Primer | Location | (SEQ ID) | Primers (5'–3') | PCR product size (kb) | Conditions MgCl$_2$ | Annealing temperature (° C.) |
|---|---|---|---|---|---|---|
| 1 EX103L | Exon 9 | (SEQ ID NO: 79) | CTGCCATGGTGTGGACGGTT | 170/173 | 1.5 | 60 |
| EX102R | Exon 10 | (SEQ ID NO: 80) | CTCCAGCTCCTCCCCTGGG | | | |
| 2 ADC22R2 | 3' UTR | (SEQ ID NO: 81) | GGACAAAGCATTGGGAACACT | 408 | 1.5 | 56 |
| ADC22L5 | 3' UTR | (SEQ ID NO: 82) | TGAGGGACATGGTGTGCCACAGG | | | |
| 3 DMO1014 | 3' UTR | (SEQ ID NO: 83) | GAACTGAGAAGGTCAGATTA | 268 | 1.5 | 56 |
| DMO1009 | 3' UTR | (SEQ ID NO: 84) | ACAGGACTCATCTATTTATCCATA | | | |
| 4 DMO1018 | 3' UTR | (SEQ ID NO: 85) | ATTGGATGCAGTTGTATAGT | 229 | 1.5 | 56 |
| DMO1021 | 3' UTR | (SEQ ID NO: 86) | TAATCTGACCTTCTCAGTTC | | | |

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated nucleic acid molecule comprising a polynucleotide sequence selected from the group consisting of:
   (a) a nucleotide sequence as set forth in SEQ ID NO:1;
   (b) a nucleotide sequence which encodes a polypeptide having the amino acid sequence set forth in SEQ ID NO:2 except with an asparagine to isoleucine substitution at residue 141; and
   (c) a complement of either (a) or (b).

2. An expression vector, comprising a promoter operably linked to the nucleic acid molecule according to claim 1.

3. The expression vector according to claim 2 wherein said promoter is selected from the group consisting of CMV I-E promoter, SV40 early promoter and MuLV LTR.

4. The expression vector according to claim 2 wherein said promoter is a tissue-specific promoter.

5. An isolated host cell carrying the vector according to claim 2.

6. The host cell according to claim 5 wherein said cell is selected from the group consisting of human cell, dog cell, monkey cell, rat cell and mouse cell.

7. A composition comprising an isolated host cell according to claim 5 and a pharmaceutically acceptable carrier or diluent.

8. A composition comprising the vector of claim 2 and a pharmaceutically acceptable carrier or diluent.

9. A viral vector comprising a promoter operably linked to the nucleic acid molecule of claim 1.

10. The viral vector according to claim 9 wherein said vector is selected from the group consisting of herpes simplex viral vectors, adenoviral vectors, adenovirus-associated viral vectors and retroviral vectors.

11. The isolated nucleic acid molecule of claim 1, wherein said molecule is the nucleotide sequence set forth in SEQ ID NO:1.

* * * * *

UNITED STATES PATENT AND TRADEMARK OFFICE
CERTIFICATE OF CORRECTION

PATENT NO. : 6,468,791 B1  Page 1 of 1
DATED : October 22, 2002
INVENTOR(S) : Rudolph E. Tanzi et al.

It is certified that error appears in the above-identified patent and that said Letters Patent is hereby corrected as shown below:

<u>Title page, Item [54] and Column 1, lines 1-3,</u>
The title should read as -- CHROMOSOME 1 GENE AND GENE PRODUCTS RELATED TO ALZHEIMER'S DISEASE --.

Signed and Sealed this

Twenty-fourth Day of June, 2003

JAMES E. ROGAN
*Director of the United States Patent and Trademark Office*

SEQUENCE LISTING (1) GENERAL INFORMATION:

(iii) NUMBER OF SEQUENCES: 88

(2) INFORMATION FOR SEQ ID NO: 1:

(i) SEQUENCE CHARACTERISTICS:
      (A) LENGTH: 2236 base pairs
      (B) TYPE: nucleic acid
      (C) STRANDEDNESS: single
      (D) TOPOLOGY: linear (xi) SEQUENCE DESCRIPTION: SEQ ID NO: 1:

```
CGAGCGGCGG CGGAGCAGGC ATTTCCAGCA GTGAGGAGAC AGCCAGAAGC AAGCTTTTGG      60

AGCTGAAGGA ACCTGAGACA GAAGCTAGTC CCCCCTCTGA ATTTTACTGA TGAAGAAAC      120

GAGGCCACAG AGCTAAAGTG ACTTTTCCCA AGGTCGCCCA GCGAGGACGT GGGACTTCT      180

AGACGTCAGG AGAGTGATGT GAGGGAGCTG TGTGACCATA GAAAGTGACG TGTTAAAAA      240
```

```
CAGCGCTGCC CTCTTTGAAA GCCAGGGAGC ATCATTCATT TAGCCTGCTG AGAAGAAGA       300

ACCAAGTGTC CGGGATTCAG ACCTCTCTGC GGCCCCAAGT GTTCGTGGTG CTTCCAGAG       360

CAGGGCTATG CTCACATTCA TGGCCTCTGA CAGCGAGGAA GAAGTGTGTG ATGAGCGGA       420

GTCCCTAATG TCGGCCGAGA GCCCCACGCC GCGCTCCTGC CAGGAGGGCA GGCAGGGCC       480

AGAGGATGGA GAGAACACTG CCCAGTGGAG AAGCCAGGAG AACGAGGAGG ACGGTGAGG       540

GGACCCTGAC CGCTATGTCT GTAGTGGGGT TCCCGGGCGG CCGCCAGGCC TGGAGGAAG       600

GCTGACCCTC AAATACGGAG CGAAGCACGT GATCATGCTG TTTGTGCCTG TCACTCTGT       660

CATGATCGTG GTGGTAGCCA CCATCAAGTC TGTGCGCTTC TACACAGAGA AGAATGGAC       720

GCTCATCTAC ACGCCATTCA CTGAGGACAC ACCCTCGGTG GGCCAGCGCC TCCTCAACT       780

CGTGCTGAAC ACCCTCATCA TGATCAGCGT CATCGTGGTT ATGACCATCT TCTTGGTGG       840

GCTCTACAAG TACCGCTGCT ACAAGTTCAT CCATGGCTGG TTGATCATGT CTTCACTGA       900

GCTGCTGTTC CTCTTCACCT ATATCTACCT TGGGGAAGTG CTCAAGACCT ACAATGTGG       960

CATGGACTAC CCCACCCTCT TGCTGACTGT CTGGAACTTC GGGGCAGTGG GCATGGTG      1020

CATCCACTGG AAGGGCCCTC TGGTGCTGCA GCAGGCCTAC CTCATCATGA TCAGTGCG      1080

CATGGCCCTA GTGTTCATCA AGTACCTCCC AGAGTGGTCC GCGTGGGTCA TCCTGGGC      1140

CATCTCTGTG TATGATCTCG TGGCTGTGCT GTGTCCCAAA GGGCCTCTGA GAATGCTG      1200

AGAAACTGCC CAGGAGAGAA ATGAGCCCAT ATTCCCTGCC CTGATATACT CATCTGCC      1260

GGTGTGGACG GTTGGCATGG CGAAGCTGGA CCCCTCCTCT CAGGGTGCCC TCCAGCTC      1320

CTACGACCCG GAGATGGAAG AAGACTCCTA TGACAGTTTT GGGGAGCCTT CATACCCC      1380

AGTCTTTGAG CCTCCCTTGA CTGGCTACCC AGGGGAGGAG CTGGAGGAAG AGGAGGAA      1440

GGGCGTGAAG CTTGGCCTCG GGACTTCAT CCTCTACAGT GTGCTGGTGG GCAAGGCG       1500

TGCCACGGGC AGCGGGGACT GGAATACCAC GCTGGCCTGC TTCGTGGCCA TCCTCATT      1560

CTTGTGTCTG ACCCTCCTGC TGCTTGCTGT GTTCAAGAAG GCGCTGCCCG CCCTCCCC      1620

CTCCATCACG TTCGGGCTCA TCTTTTACTT CTCCACGGAC AACCTGGTGC GGCCGTTC      1680

GGACACCCTG GCCTCCCATC AGCTCTACAT CTGAGGGACA TGGTGTGCCA CAGGCTGC      1740

GCTGCAGGGA ATTTTCATTG GATGCAGTTG TATAGTTTTA CACTCTAGTG CCATATAT      1800

TTAAGACTTT TCTTTCCTTA AAAAATAAAG TACGTGTTTA CTTGGTGAGG AGGAGGCA      1860

ACCAGCTCTT TGGTGCCAGC TGTTTCATCA CCAGACTTTG GCTCCCGCTT TGGGGAGC      1920

CTCGCTTCAC GGACAGGAAG CACAGCAGGT TTATCCAGAT GAACTGAGAA GGTCAGAT      1980

GGGCGGGGAG AAGAGCATCC GGCATGAGGG CTGAGATGCG CAAAGAGTGT GCTCGGGA      2040

GGCCCCTGGC ACCTGGGTGC TCTGGCTGGA GAGGAAAAGC CAGTTCCCTA CGAGGAGT      2100

TCCCAATGCT TTGTCCATGA TGTCCTTGTT ATTTTATTGC CTTTAGAAAC TGAGTCCT      2160

TCTTGTTACG GCAGTCACAC TGCTGGGAAG TGGCTTAATA GTAATATCAA TAAATAGA      2220

AGTCCTGTTA GAAAAA                                                      2236
```

(2) INFORMATION FOR SEQ ID NO: 2:

(i) SEQUENCE CHARACTERISTICS:
        (A) LENGTH: 448 amino acids
        (B) TYPE: amino acid
        (C) STRANDEDNESS: <Unknown>
        (D) TOPOLOGY: linear (xi) SEQUENCE DESCRIPTION: SEQ ID NO: 2:

-continued

```
Met Leu Thr Phe Met Ala Ser Asp Ser Glu Glu Val Cys Asp Gl
1               5                   10                  15

Arg Thr Ser Leu Met Ser Ala Glu Ser Pro Thr Pro Arg Ser Cys Gl
            20                  25                  30

Glu Gly Arg Gln Gly Pro Glu Asp Gly Glu Asn Thr Ala Gln Trp Ar
        35                  40                  45

Ser Gln Glu Asn Glu Glu Asp Gly Glu Glu Asp Pro Asp Arg Tyr Va
        50                  55                  60

Cys Ser Gly Val Pro Gly Arg Pro Pro Gly Leu Glu Glu Glu Leu Th
65                  70                  75                  80

Leu Lys Tyr Gly Ala Lys His Val Ile Met Leu Phe Val Pro Val Th
            85                  90                  95

Leu Cys Met Ile Val Val Val Ala Thr Ile Lys Ser Val Arg Phe Ty
            100                 105                 110

Thr Glu Lys Asn Gly Gln Leu Ile Tyr Thr Pro Phe Thr Glu Asp Th
            115                 120                 125

Pro Ser Val Gly Gln Arg Leu Leu Asn Ser Val Leu Asn Thr Leu Il
            130                 135                 140

Met Ile Ser Val Ile Val Val Met Thr Ile Phe Leu Val Val Leu Ty
145                 150                 155                 160

Lys Tyr Arg Cys Tyr Lys Phe Ile His Gly Trp Leu Ile Met Ser Se
            165                 170                 175

Leu Met Leu Leu Phe Leu Phe Thr Tyr Ile Tyr Leu Gly Glu Val Le
            180                 185                 190

Lys Thr Tyr Asn Val Ala Met Asp Tyr Pro Thr Leu Leu Leu Thr Va
            195                 200                 205

Trp Asn Phe Gly Ala Val Gly Met Val Cys Ile His Trp Lys Gly Pr
210                 215                 220

Leu Val Leu Gln Gln Ala Tyr Leu Ile Met Ile Ser Ala Leu Met Al
225                 230                 235                 240

Leu Val Phe Ile Lys Tyr Leu Pro Glu Trp Ser Ala Trp Val Ile Le
            245                 250                 255

Gly Ala Ile Ser Val Tyr Asp Leu Val Ala Val Leu Cys Pro Lys Gl
            260                 265                 270

Pro Leu Arg Met Leu Val Glu Thr Ala Gln Glu Arg Asn Glu Pro Il
            275                 280                 285

Phe Pro Ala Leu Ile Tyr Ser Ser Ala Met Val Trp Thr Val Gly Me
            290                 295                 300

Ala Lys Leu Asp Pro Ser Ser Gln Gly Ala Leu Gln Leu Pro Tyr As
305                 310                 315                 320

Pro Glu Met Glu Glu Asp Ser Tyr Asp Ser Phe Gly Glu Pro Ser Ty
            325                 330                 335

Pro Glu Val Phe Glu Pro Pro Leu Thr Gly Tyr Pro Gly Glu Glu Le
            340                 345                 350

Glu Glu Glu Glu Glu Arg Gly Val Lys Leu Gly Leu Gly Asp Phe Il
            355                 360                 365

Phe Tyr Ser Val Leu Val Gly Lys Ala Ala Thr Gly Ser Gly Asp
            370                 375                 380

Trp Asn Thr Thr Leu Ala Cys Phe Val Ala Ile Leu Ile Gly Leu Cy
385                 390                 395                 400

Leu Thr Leu Leu Leu Leu Ala Val Phe Lys Ala Leu Pro Ala Le
            405                 410                 415
```

-continued

```
Pro Ile Ser Ile Thr Phe Gly Leu Ile Phe Tyr Phe Ser Thr Asp As
            420                 425                 430

Leu Val Arg Pro Phe Met Asp Thr Leu Ala Ser His Gln Leu Tyr Il
            435                 440                 445
```

(2) INFORMATION FOR SEQ ID NO: 3:

(i) SEQUENCE CHARACTERISTICS:
        (A) LENGTH: 467 amino acids
        (B) TYPE: amino acid
        (C) STRANDEDNESS: <Unknown>
        (D) TOPOLOGY: linear (xi) SEQUENCE DESCRIPTION: SEQ ID NO: 3:

```
Met Thr Glu Leu Pro Ala Pro Leu Ser Tyr Phe Gln Asn Ala Gln Me
1               5                   10                  15

Ser Glu Asp Asn His Leu Ser Asn Thr Val Arg Ser Gln Asn Asp As
            20                  25                  30

Arg Glu Arg Gln Glu His Asn Asp Arg Arg Ser Leu Gly His Pro Gl
            35                  40                  45

Pro Leu Ser Asn Gly Arg Pro Gln Gly Asn Ser Arg Gln Val Val Gl
    50                  55                  60

Gln Asp Glu Glu Asp Glu Glu Leu Thr Leu Lys Tyr Gly Ala Ly
65                  70                  75                  80

His Val Ile Met Leu Phe Val Pro Val Thr Leu Cys Met Val Val Va
                85                  90                  95

Val Ala Thr Ile Lys Ser Val Ser Phe Tyr Thr Arg Lys Asp Gly Gl
            100                 105                 110

Leu Ile Tyr Thr Pro Phe Thr Glu Asp Thr Glu Thr Val Gly Gln Ar
            115                 120                 125

Ala Leu His Ser Ile Leu Asn Ala Ala Ile Met Ile Ser Val Ile Va
            130                 135                 140

Val Met Thr Ile Leu Leu Val Val Leu Tyr Lys Tyr Arg Cys Tyr Ly
145                 150                 155                 160

Val Ile His Ala Trp Leu Ile Ile Ser Ser Leu Leu Leu Leu Phe Ph
                165                 170                 175

Phe Ser Phe Ile Tyr Leu Gly Glu Val Phe Lys Thr Tyr Asn Val Al
            180                 185                 190

Val Asp Tyr Ile Thr Val Ala Leu Leu Ile Trp Asn Phe Gly Val Va
            195                 200                 205

Gly Met Ile Ser Ile His Trp Lys Gly Pro Leu Arg Leu Gln Gln Al
    210                 215                 220

Tyr Leu Ile Met Ile Ser Ala Leu Met Ala Leu Val Phe Ile Lys Ty
225                 230                 235                 240

Leu Pro Glu Trp Thr Ala Trp Leu Ile Leu Ala Val Ile Ser Val Ty
            245                 250                 255

Asp Leu Val Ala Val Leu Cys Pro Lys Gly Pro Leu Arg Met Leu Va
            260                 265                 270

Glu Thr Ala Gln Glu Arg Asn Glu Thr Leu Phe Pro Ala Leu Ile Ty
            275                 280                 285

Ser Ser Thr Met Val Trp Leu Val Asn Met Ala Glu Gly Asp Pro Gl
    290                 295                 300

Ala Gln Arg Arg Val Ser Lys Asn Ser Lys Tyr Asn Ala Glu Ser Th
305                 310                 315                 320

Glu Arg Glu Ser Gln Asp Thr Val Ala Glu Asn Asp Asp Gly Gly Ph
            325                 330                 335
```

Ser Glu Glu Trp Glu Ala Gln Arg Asp Ser His Leu Gly Pro His Ar
            340                 345                 350

Ser Thr Pro Glu Ser Arg Ala Ala Val Gln Glu Leu Ser Ser Ser Il
            355                 360                 365

Leu Ala Gly Glu Asp Pro Glu Glu Arg Gly Val Lys Leu Gly Leu Gl
            370                 375                 380

Asp Phe Ile Phe Tyr Ser Val Leu Val Gly Lys Ala Ser Ala Thr Al
385                 390                 395                 400

Ser Gly Asp Trp Asn Thr Thr Ile Ala Cys Phe Val Ala Ile Leu Il
                405                 410                 415

Gly Leu Cys Leu Thr Leu Leu Leu Ala Ile Phe Lys Lys Ala Le
            420                 425                 430

Pro Ala Leu Pro Ile Ser Ile Thr Phe Gly Leu Val Phe Tyr Phe Al
            435                 440                 445

Thr Asp Tyr Leu Val Gln Pro Phe Met Asp Gln Leu Ala Phe His Gl
    450                 455                 460

Phe Tyr Ile
465

(2) INFORMATION FOR SEQ ID NO: 4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO: 4:

ACGAACATTC TACAAGTTAC TTTCAGAGAA ACTGACCTGT                    40

(2) INFORMATION FOR SEQ ID NO: 5:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO: 5:

CATTATCCAA GGTCAGGAGG AGCTGTTAAT CCAATCTATG ATGTG             45

(2) INFORMATION FOR SEQ ID NO: 6:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO: 6:

TGGCCTGAAT AGACCATAAA AAGCCTGGGT GACAAAGCA                    39

(2) INFORMATION FOR SEQ ID NO: 7:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 7:

AGCTGTGTCG GGTCTTGAGA GCGATTTCAG AATGTTGC                     38

(2) INFORMATION FOR SEQ ID NO: 8:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO: 8:

GCTTGTTTCC ATTTATGGTG ACTCTAGTTG TGTGTGAATG TATG            44

(2) INFORMATION FOR SEQ ID NO: 9:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO: 9:

TTTTGGCACC AGTAATATCT TGTTGCAGAC TCTGAACTTA GAACA           45

(2) INFORMATION FOR SEQ ID NO: 10:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO: 10:

CACAGACTTC ATTAGAGGGG GTTGAAATGG TGAATTTGGA                40

(2) INFORMATION FOR SEQ ID NO: 11:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO: 11:

AGCTGGGGTG TTTTATGGAG GGGGACCCTG TTTCTGCTAC                40

(2) INFORMATION FOR SEQ ID NO: 12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 12:

ACCCATTGCC ACCATCGGGG AGATTTGGAC TGG                        33

(2) INFORMATION FOR SEQ ID NO: 13:

(i) SEQUENCE CHARACTERISTICS:
        (A) LENGTH: 193 base pairs
        (B) TYPE: nucleic acid
        (C) STRANDEDNESS: single
        (D) TOPOLOGY: linear (xi) SEQUENCE DESCRIPTION: SEQ ID NO: 13:

AGTGAAATCG TCCTGTGACC ACGCGTCAAG TGCTGATGGG GCACAGCAAC TTCCGGGCCT    60

| ATCATATCTC CTTGACCTCG TCCCTAATCT GGTAGTTTCT GCACCGAGGG ACAGTCCAC | 120 |
| GCGATGAAGT ATGTTCAAAA TCGTTTTCTA TAGGCAGGTC CTTCCAAAGT CCAATAGTG | 180 |
| AAGGTGGACG CTT | 193 |

(2) INFORMATION FOR SEQ ID NO: 14:

(i) SEQUENCE CHARACTERISTICS:
        (A) LENGTH: 473 base pairs
        (B) TYPE: nucleic acid
        (C) STRANDEDNESS: single
        (D) TOPOLOGY: linear (xi) SEQUENCE DESCRIPTION: SEQ ID NO: 14:

| GAGAAGGTAA GAGCTGACCC TCAAATACGG AGCGANACGT NATCATGCTG TTTGTGCCTG | 60 |
| TCACTCTGTG CATGATCGTG GTGGTAGCCA CCATAGTCTG TGCGCTTCTA CACAGAGAA | 120 |
| AATGGACAGC TCATCTACAC GCCATTCACT GAGGACACAC CCTCGGTGGG CCAGCGCCT | 180 |
| CTCAACTCCG TGCTGAACAC CCTCATCATG ATCAGCGTCA TCGTGGTTAT GACCATCTT | 240 |
| TTGGTGGTGC TCTACAAGTA CCGCTGCTAC AAGTTCATCC ATGGCTGGTT GATCATGTC | 300 |
| TCACTGATGC TGCTGTTCCT CTTCACCTAT ATCTACCTTG GGGAAGTGCT CAAGACCTA | 360 |
| AATGTGGCCA TGGACTACCC CACCCTCTTG CTGACTGTCT GGGAACTTCG GGGCAGTGG | 420 |
| CATGGTGTGC ATCCACTGAA GGGGCCTTTG GTGCTGCAGA GGCCTACCTA TCA | 473 |

(2) INFORMATION FOR SEQ ID NO: 15:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (xi) SEQUENCE DESCRIPTION: SEQ ID NO: 15:

| GGTGGNGCTC TACAAGTACC GCTGCTACAA GGTGAGGCCC TGGCCTGCCC TCCAGCCACC | 60 |
| CTTCTCTCCG TCTGCCCCAC ACCATGGCGG CAGGGCCGTG AAACAGCCGC CTTTAGAAA | 120 |
| ACACAAATTA GAGGAAAATA GACCCAGATT TTTTGTACTC CTCCCCACCC CATCCTGTC | 180 |
| CCCACCGTGG ATGACCTAAT ACTGTTGTCT TTTATTTTTA TTTATTTTCT TTTTCTTGA | 240 |
| ACATGGTCTC ACTCCATTGC CCAGGCTGGA GTGCAGTGGT GC | 282 |

(2) INFORMATION FOR SEQ ID NO: 16:

(i) SEQUENCE CHARACTERISTICS:
        (A) LENGTH: 425 base pairs
        (B) TYPE: nucleic acid
        (C) STRANDEDNESS: single
        (D) TOPOLOGY: linear (xi) SEQUENCE DESCRIPTION: SEQ ID NO: 16:

| TGCTGATATA CTGTATGTTG TCTATATATC ATCTAACACC CTCACACTGG AACACAATGC | 60 |
| CCGTGGGCAG AGACTTTGCT AGCCTTGGTT CCAGAGCCTA GAACAGTGCC TGGCAAGTA | 120 |
| GAGACACCCA GCATTACCTT TCTAAGTGAA CCAGTAGAGA TGGGGGGAGA CGCAAGCTA | 180 |
| GCCGGCAGAC CTGAGGGAGT CCTGTCTGCA TGCGCTGCAG GATGACCTGA GGGGAACTC | 240 |
| TTGGACTTCT GTGCCCTCTT TATCTGTAAG GTGGCCACCT GATCCCTTCC AGCGTAGGC | 300 |
| TGAAGTAGCC TAATGAAGAG CATTCAGGCT TGGGTATCAG TCTCAGGATC CTGGGGGCC | 360 |
| TAGAATTTGT GGCGCTTGGG GACACCTTGT GATCGNGNAA TTTCNGTTGT CTAGNNCAT | 420 |

```
CATGG                                                                    425

(2) INFORMATION FOR SEQ ID NO: 17:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (xi) SEQUENCE DESCRIPTION: SEQ ID NO: 17:

GGACACACCC TCGGTGGGCC                                                     20

(2) INFORMATION FOR SEQ ID NO: 18:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (xi) SEQUENCE DESCRIPTION: SEQ ID NO: 18:

CAAGGTAGAT ATAGGTGA                                                       18

(2) INFORMATION FOR SEQ ID NO: 19:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (xi) SEQUENCE DESCRIPTION: SEQ ID NO: 19:

CTTGGTGGTG CTCTACAAGT AC                                                  22

(2) INFORMATION FOR SEQ ID NO: 20:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (xi) SEQUENCE DESCRIPTION: SEQ ID NO: 20:

GTAGTCCATG GCCACATTGT                                                     20

(2) INFORMATION FOR SEQ ID NO: 21:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (xi) SEQUENCE DESCRIPTION: SEQ ID NO: 21:

TCCTCAACTC CGTGCTGAAC                                                     20

(2) INFORMATION FOR SEQ ID NO: 22:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (xi) SEQUENCE DESCRIPTION: SEQ ID NO: 22:

AGCATCAGTG AAGACATGAT C                                                   21
```

(2) INFORMATION FOR SEQ ID NO: 23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 23:

ACCACCGGGG CAACCTGA                                          18

(2) INFORMATION FOR SEQ ID NO: 24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 24:

AGGAAGCAGA TCTCAATAGG A                                   21

(2) INFORMATION FOR SEQ ID NO: 25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 25:

GAGAAGGTAA GAGCTGACCC                                    20

(2) INFORMATION FOR SEQ ID NO: 26:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 26:

TGATAGGTAG GCCTCTGCAG C                                   21

(2) INFORMATION FOR SEQ ID NO: 27:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 27:

TCCAGCCACC CTTCTCTCC                                          19

(2) INFORMATION FOR SEQ ID NO: 28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 28:

CAGTATTAGG TCATCCACGG T                                   21

(2) INFORMATION FOR SEQ ID NO: 29:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 29:

GTGGGGCAGA CGGAGAGAA                                             19

(2) INFORMATION FOR SEQ ID NO: 30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 30:

CCCAAGTGTT CGTGGTGCTT                                          20

(2) INFORMATION FOR SEQ ID NO: 31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 31:

ACTGTGGACA TAGCGGTCAG G                                       21

(2) INFORMATION FOR SEQ ID NO: 32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 32:

GGTAGATATA GGTGAAGAGG                                          20

(2) INFORMATION FOR SEQ ID NO: 33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 33:

TCACTGAGGA CACACCCTCG                                          20

(2) INFORMATION FOR SEQ ID NO: 34:

(i) SEQUENCE CHARACTERISTICS:
        (A) LENGTH: 1318 base pairs
        (B) TYPE: nucleic acid
        (C) STRANDEDNESS: single
        (D) TOPOLOGY: linear (xi) SEQUENCE DESCRIPTION: SEQ ID NO: 34:

CTGCGCCCTG GGGGCCCTGC CCTGCCCTCC GCACGCCTCT GGCCACGGTC CCTTCCCCGG     60

CTGTGGGTCT GCGGCCCCTG CGTGCGCAGC TCCTGGCCTC TGCGGCCAGC GCGGGGGCG     120

| | |
|---|---:|
| AGAGAGGAGA GTGCCCGGCA GGCGGCGGCT GGGCCGGCCC GGAACTGGGT CGTGGAAGG | 180 |
| TCGCGGGGAG CGGCCCTCAG GCCTTCGGCT CACTGCGTCC CCACTTCCCT GCGCCCGNC | 240 |
| GCCGCCGAGC CCCGGCTGGG GGTGGGCGCG CGCGAGCGG TTAAAGGGCC GGTGCATTT | 300 |
| AAGGAGCGGT GCACGTGGGT CTCTGAGGCG TGTAGCAGGC GGGGGCGTTT TGTTCTTCT | 360 |
| CTCTCTCGCC GGAGACCTCC GTTGCGCCGA GTCCATTCGG CCTCTAGCAC CGGGTCCTG | 420 |
| GCATGCTTTC CCCGGGAAGG AGGCGCGCGG GGGCTCTGCC CGCACGTGAG GGCAGGGC | 480 |
| GCAGGCTCAA GCCTAGAGCC GGTTTCTGTT AGCAGCGGTG TTTGGCTGTT TTATCAGGC | 540 |
| TTTCCAGCAG TGAGGAGACA GCCAGAAGCA AGCTTTTGGA GCTGAAGGAA CCTGAGACA | 600 |
| AAGCTAGTCC CCCCTCTGAA TTTTACTGAT GAAGAAACTG AGGCCACAGA GCTAAAGTG | 660 |
| CTTTTCCCAA GGTCGCCCAG GTACGATATA GCAGAGCCAG GCTTCGACCC CAGTGTCCT | 720 |
| GCTTCTAGAT CTGCTGTCCA TCCCTCCGAG CAGACCTCAC CCCTGTTTAT TGCCTTAAT | 780 |
| AGTATTCCCT TTGAAAGGTA TGAACGGTGT TGAGTGAAGT AACTGCATCC CTATTTACA | 840 |
| ATGGAGAACC TGAGAGCATT CCATAGAGAC GATTGTAGAC TAACTTAACT CAGAAGCGA | 900 |
| AGCCTGGGGT TGCCAAGGCT GTCTACGAAG TAACTTGATT AGGACCGACC CCAGCTTCC | 960 |
| GTAAGGAAGC CTCTGATGCC TCTGTAGCCA ATTCTGCAGA CACCTGAGCC TCCAAGGC | 1020 |
| TCAGCCAAGA CCTTTGGCGG TAATTGGAGT CTCGGGATAA GCTGCTTCAG GTGTGTGA | 1080 |
| CTCAGGTTCT TCTCTCCTGA ATGTGGTTGT GGGCAGCCGG TGACTGGCGC AGGTGCAG | 1140 |
| GGGGCCTGGT TCTTGGCCCC ACCTCAGAGC TGCGTCCTCA CGACGCCCAC GTTGAGCC | 1200 |
| GGGTTCCAGG GCAGAGACTG GAGTGAGGGC TTGGGGGCAT GTTGCTTTGA AGTGGGAT | 1260 |
| ATGTATCAGG TTTTTGGGGA AAACTCTGTA CCCTTTGGTG TTGAAGTCCC ATGTGCCA | 1318 |

(2) INFORMATION FOR SEQ ID NO: 35:

(i) SEQUENCE CHARACTERISTICS:
        (A) LENGTH: 2001 base pairs
        (B) TYPE: nucleic acid
        (C) STRANDEDNESS: single
        (D) TOPOLOGY: linear (xi) SEQUENCE DESCRIPTION: SEQ ID NO: 35:

| | |
|---|---:|
| CGGGAATGGA AACTTGATCT CTGGGGCCTG GCCTTTGAAG CCAGTTCATG TGTCTGGTGG | 60 |
| TTCAGCAGAT CCGTAACTTT CCAAGAGGCA CATCCATAGG CTACCGTGTC CTTTCTCAC | 120 |
| GTGTCCCTCC TCCATTTCAT CTTCTTTATA ACTACGACTT ATTGAACATC TACTGTGTG | 180 |
| TGGACACTTT ACAGGTTATC TCTAGGTTTT ACGATAATCT TGCAAGGTAT GCCTGTTCT | 240 |
| CTTTTTACAG CAGAGGAAAT GAGCTGTGTC AGATTAGACT GTCTGAGGCC TCTTGGCCA | 300 |
| GGAGTATGTG GTTCAAATCA CATAGGCAGG CGATCTGAAC CCTGTCAGTC TCCAAAGCC | 360 |
| CTGCTTTTGA CCGCTGACTT GCTGCTGCTT GTTTAAAAAT AAATGTGTTT CTGGAGCCT | 420 |
| CTCCAGAGGG GCGTGCTAGG GGCTCCCTCT CCCACTTCCC CACAAACCAC CCTTTTCCC | 480 |
| GGCTGCTTCA GGAAATGAGA GAACTCTGCC TGGGCCCCAG GCACTTCTGA GTGGGACAG | 540 |
| GCTGTTAGAG GTAAGTCTAG AGCCTGGCCC AAAATTCAGG AGGCCCCATC AGAGGGCCC | 600 |
| TGGGGCTGTG GTCCGGGAGG GTGGTAGGGC AGTACCTCAC TTCCCTTTGA GACTCAGGC | 660 |
| CCAGCTCTGG CTTAGGCCAG GGAGAACCAT CCCCAAGTGG TATGTGTTAC TATATGAGC | 720 |
| GAGATGGATG GTCAGCTGGA CCAAATACAT AGTCGGGTAC CCAGGGCCAG GGGGAGGAA | 780 |
| GTGAGCAGGG AAGCTGTGGG CAATTGTCTG GGTATCACCT GACCTTAGCA AACTCTTCC | 840 |

-continued

```
TGTTTTAAGC GAGGACGTGG GACTTCTCAG ACGTCAGGAG AGTGATGTGA GGGAGCTGT      900
TGACCATAGA AAGTGACGTG TTAAAAACCA GCGCTGCCCT CTTTGAAAGC CAGGGAGCA      960
CATTCATTTA GCCTGCTGAG AAGAAGAAAC CAAGTGTCCG GGATTCAGAC CTCTCTGC      1020
CCCCAAGTGT TCGTGGTAAG TGCAGTGACT CCCAACCTGC TTTTGAACCC TCTTTTTC      1080
TTAGGATTTT CTCCGTGGAG GCAGATTTCC ATGGGAGTTT GCTGTGGCAT TTTGAAAT      1140
GTTTCTTACC TAGTTCCATT GGCCTTAAAT GTTAAGGCCA AAGCCTTTAC ATTTCTCT      1200
AATGAAAAGA AGGTCGAGGA AATTGGGTCA TTGGGTTTCC ATAATGATTG CAGGAACT      1260
TGACACAAGC ACGGCTGGGG AGATTCTCTA GGTCAGACTC CCTTGGTTTG GCTAATTC      1320
CAGTTTGATC CCATTCAGCT GATTAATGGG AATGTGCAGT GGCTTCTTTG GATGTTTG      1380
TTTGCATCCT AATCCAAAGC AGCTATCAGC CTCAGCACTT CCTTGTTGGA AGGCTTTC      1440
GAACGTAGTC TATGCTGGAC ACTTCCTTCT GCCTCTCTGC ATTTTCCTGC CACTTCTC      1500
GAGAATGGGG TGCAGGGGGT GGGAGACGGG GAAAGCTGGT CGCTGAGTGG CTGATGGG      1560
TTGACATCAC CCAGCCCCAC CCCCACCTGC CCGTGAGTCA GCCTCCGGGG AGAGTTCA      1620
GCGTCACCGG CACTCTAATG TGGACAGACA CCTAGCAGTG TTGTTTATCT GCACACGT      1680
GGGTGGTGAT TTTTCCCTCC AAGGATTTCA GAGCACCAGC AGGCTTCAGA GCAGACTT      1740
GTGGCTTGCA AAGCAGGCCC TCAGGAATTC AGAGGGTAGC AGAAGTCCAT CCCAGATG      1800
CTGTTTTCCT TCAGGAGCTA GGTAAATCAG AGGGGCTGAG GGACAAATGA AAAAAGTT      1860
AGCCTTTGAG TCCCATCTGC TCCTCCTGGC CAATGAGAGG GGATCTGGGA GGGGCAGA      1920
TAGAGGAAAA TCTGTCTAAA TGTTGATGCT CGTTATTTTC CTTTAAAGAA TTAATAGC      1980
AAAATAAACC CTACAGATAC A                                              2001

(2) INFORMATION FOR SEQ ID NO: 36:

(i) SEQUENCE CHARACTERISTICS:
        (A) LENGTH: 3349 base pairs
        (B) TYPE: nucleic acid
        (C) STRANDEDNESS: single
        (D) TOPOLOGY: linear (xi) SEQUENCE DESCRIPTION: SEQ ID NO: 36:

CACCACAGAT GTTTGCTGAT TGAATGAATG AGCACACTGA CAGTTTGGAG CTGCCCTGAC      60
TTTCGTGGCT ATGCGTTTTG CCCCCTGGGA TGTGAGTCAC CTCAGGCCAG CCCCAGGCA      120
GGCCGCTGCT GCCTCCATGG TAACTCTCAA GGCCTCTTGT TTTATGGCAG TCGTTTGAT      180
GACAGGCATC TCTTGGAAGC TTTTGGGGCA GGACTTGTGT CCAAGTCTCC AGGTCGCCT      240
CAGCCACCCC CTGAGTCCTC CACTGCCTTT GTCTCACAGG AAAGTGGAAC AAGGTCCTT      300
TGCTCCTTTT TCCAGGTGCT TCCAGAGGCA GGGCTATGCT CACATTCATG GCCTCTGAC      360
GCGAGGAAGA AGTGTGTGAT GAGCGGACGT CCCTAATGTC GGCCGAGAGC CCCACGCCG      420
GCTCCTGCCA GGAGGGCAGG CAGGGCCCAG AGGATGGAGA GAANACTGCC CAGTGGGTA      480
GTCCCACCAG CAGCTGGGGG CCTTCAAACA GGTCCTGCGG CTACTGTACC TTACAGATG      540
AAACCAGACA TTCATTCCCT GATGCGGGAG GGAGAAGGGA AGTAATGATG AGGATTGGC      600
GAAAAGGTGG GTGGCTGGCC ATGATGGACC TTCCATCTGC AGGGTTTCAT AGGACTGCG      660
ATTCACAGCC AGAGATGGAC TTGGCAGTGG GCTGAAGACG CTGTCCACTC TGCCACCTT      720
GGTTTACCTC TCTCATGCAG GTCACTGTTT CCACTGTAAT AGGAGAGTTT GTTTGGATG      780
CTGGGTGCTA GGACAGGTAA CACAGAAGCT TAGGATGGTA GCAGGGGAAG CATTTTTTG      840
```

```
CAGATGGCCA GACATGGTAA GTGTGAGAGG AGTCTGCCTG ATACACGATT GACTTTTGA     900
CTGGGGATAT TTGGGCTTCA CTGTGATCAT TCAGCCCCCA GGGGAGGAGA TTGTAACGT     960
AGAAAGAGTA GGATATCGTT GGGAGAGCCA CTTAGTTGTG TCCTTTCTCT CCCGATCA     1020
GCAGAACATC TGAATTTGCC TGAACCCTGT TCTCTGTTTT GCCCATTATA GAATTAAA     1080
ATGTCTCTGT GTGGACTGTT TTTTTGCAGC CAGTCTTAAT CCTGCTTGCT GAAATTTG     1140
CTCACTTCTC CATGTTCTCC TTGAGAACGG AACCATCGTC CCTAAGCCCT GAGTGAAA     1200
ACACCAGCTT AAGGCCACTG CTCTGCCACT CCTCAGCCTT TTCTTGTTTG TTATCTCC     1260
GAAGTTTTGT ACACTTTGGT TGTTTCAGTT TCTGTTCATG AGTAGTCTTC TTTCTTGG     1320
GAACGTCTAG ATTGGGACTC TCTCTGCAGA GAACCGGTAC TGAAGCAACT GTCATTTT     1380
GTTTTTGTTT CATTTGGCTT TTTCTTTAGC TGTTCACCTT ATTAGCAAGG CAGCCCAT     1440
CCTTGACTTG CCACAGTTCC AAAACACAAA TTCTTACAGA TCGGTTTGTG CTAGTGTC     1500
GCAGGTGTCC TGCCCTCCCT CGTTACCTCC TCATTTGTGC CTGCCCACCT TCCCAGAG     1560
TGCGTCTTCT CAGATGCTTA ACACCTGTTT AGCCTCTCTA GTTCAGAGCT ACAAATTT     1620
ATGCTTGATT CTGTGGGGCA GAAAGTTCAA AGTAATTTCT TCCTCTGCAA ATTCCCAG     1680
TCTTAGTCAC ACGCAAAGAG AGTGTCCCTG TGCACTGACT CCTCTAGCTA GTGATTTG     1740
GCCAAAAATG TTTATTTATC TCCTGGCCTG TCTCCTCCCA TATCAGTATG CCACATG      1800
CAGAATTGAG TGACCTCCTG AGTCCCTGTA TTAGGAAGGG GAAAGATCTT TTGATTCA     1860
AACCATTAAG TTGATTCATT AACCATTAAG TCTTGGGCCT GCAGACCATA GCAACCTT     1920
TTCCTTCATT TATGGTGCTT CATCCAGCTC CAAATCTTCT CTACTTTGTC CTCACAAA     1980
TTTCATATGC CCTAGTAGCT CATAGACTGC TCCTTATATC TGGAAAGCAA CATTCAAA     2040
TCTCATTTCT GGTTCCAAAA ATCCGTGCAT TACATGGATA GGCTGCCNTG GGGGACAT     2100
NGCGGCCCTC ACGATGTGGT TTCCCACAGA GAAGCCAGGA GAACGAGGAG GACGGTGA     2160
AGGACCCTGA CCGCTATGTC TGTAGTGGGG TTCCCGGGCG GCCGCCAGGC CTGGAGGA     2220
AGCTGACCCT CAAATACGGA GCGAAGCATG TGATCATGCT GTTTGTGCCT GTCACTCT     2280
GCATGATCGT GGTGGTAGCC ACCATCAAGT CTGTGCGCTT CTACACAGAG AAGAATGG     2340
AGCTGTGAGT TGGGGGGCTG GGGGGAGCAG GGTGGGGTGA GGGCTGAGTT GCCAGGGG     2400
GGGGGGCGCA GCAGCCTGTG TTGGTCACTG TACCTGCAGC TCCACACCAG CAGCGGTA     2460
GAGCAGGGAT GAAGAACCGC CCAGGTTCAT GGCCTGGCTC ACTGCCTCCT GGATTGTG     2520
CTACTTGGGC ATGCTTTTAA CATCCCTATG CCTCAGCTTC CTTGTTCGTA TAATGGGT     2580
ATAACGCAGT TACTGGGAGA ATTAAGTGAG TTAATATGAG TGAAGGGCTT AGAAGAGT     2640
CTACTGCACG TGAGTGCTCA GGCAAGCTGG ATCCTGCTGC AGAAAGCAAG CTCTTGAT     2700
TGGGCATGGC TGTGCCACTG ATCCCTGTGT GACTGCAAAC AAATCACTTC CTCTCTGA     2760
CTCTGCTTCC CTGAATGTGA AACAAGGTGG TTGGACCAGA TATTTCTCAG CTCACTTC     2820
GCCTTGTGAG GAAGACTTAT AAAGCCTTTC GTTTATTTTA GTAAAATACA TGCAGAGG     2880
GCAGCGTAGA AAAATGAGAA GCTTCCTCCA CTTCTTCCCC CTCCCCTTTC TGTGGTCC     2940
ACTGCTAAGC ACCTTCTGTA AACTTTTTTT TTTTTTTTA AAGTTAGGGA NTTTTGTT     3000
ATTTCGTGTG TGTTGGTTTT TTTTGTTGTT GTTGTTTCTT TTAAAGAAAG GAATAAGG     3060
AGGTGTGGTG TCTCATGCCT GTAATCCCAG CACTTTGGGA GACTGAGGTG AGAGGATT     3120
TTGAGCCCAG GAGTTTGAGA CCAGCCTGGG AAATGTGGCG AGACCCTGTC TGTACAAA     3180
```

```
ATGCAAAAAT TAGCCAGGTG TGGTGGTACA TGCCTGTAGT CTCAGCTACT TGGGAGAC      3240

AGGTGGAAGA ACACGTGAGC CCAGAAGTCG AGGCTGCAGT GAGCCATGAT TGCGCCAC      3300

CACTGCAGCC TCAGCAACAG AGTGAGACCC TGTCTCAAAA TTTTTTTAA                3349
```

(2) INFORMATION FOR SEQ ID NO: 37:

(i) SEQUENCE CHARACTERISTICS:
        (A) LENGTH: 1438 base pairs
        (B) TYPE: nucleic acid
        (C) STRANDEDNESS: single
        (D) TOPOLOGY: linear (xi) SEQUENCE DESCRIPTION: SEQ ID NO: 37:

```
CTGCTCATGG GGATGGTGCC CGCACTCCAT CAGGGCAGCA TGTGGGCAGC ATGGGCATCC      60

CAGGCACCTC CCCTAGCAGG TCCAGAATCA CTCAAGGTGG GGAGCCTCGA GGAGCAGTC      120

GGGCCGGGAG CATCAGCCCT TTGCCTTCTC CCTCAGCATC TACACGACAT TCACTGAGG      180

CACACCCTCG GTGGGCCAGC GCCTCCTCAA CTCCGTGCTG AACACCCTCA TCATGATCA      240

CGTCATCGTG GTTATGACCA TCTTCTTGGT GGTGCTCTAC AAGTACCGCT GCTACAAGG      300

GAGGCCCTGG CCCTGCCCTC CAGCCACCCT TCTCTCCGTC TGCCCCACAC CATGGCGGC      360

GGGCCCGTGA ACAGCCGCC TTTAGAAAAA CACAAATTAG AGGAAAATAG ACCCAGATT       420

TTTGTACTCC TCCCCACCCC ATCCTGTCTC CCACCGTGGA TGACCTAATA CTGTTGTCT      480

TTATTTTTAT TTATTTTCTT TTTCTTGAAA CATGGTCTCA CTCCATTGCC CAGGCTGGA      540

TGCAGTGGTG CGATCATGAC TCACTGCAGC CTCAACCTCC TGGGCTCAAG AAGTTCTCC      600

ACCCAGCCCC TCAAGTAGCT AGGACTACAG GTGTGCACCA CCATACCTGG CTAATTAAA      660

AATTTTTTTT TGTGCAGGCT AGATCTCACA GTGTTGCCCA GGCTGGTCTC AAACTCCTG      720

ACTCAAGTGA TCTCCCACCT TGGCCTCCCA AAGTTCTGGG ATTACATGTG TGAGCCATT      780

CATCCAGCCT GTTGTCTTTT AAATTTACAC ATTATCCCAC TTGAGTTCCT CATTGCAGT      840

TTCCAAGCAT CATTTCTCAT ATTTCAAAGT TAATTTTGTT TTGCTTCTCT TTCTGAAGT      900

CTATTTTAGG CTCCCCTCAC CCCGATACTT CCCCTGAAGA TTTATTTTTA GTTTTCCTT      960

TCCTTTTCGG GCAAGGATGT GCAGAGGCCA TGCTGAGGTC TTGCAGCCCT GGGAGACT      1020

TGGGTTGTAG CTGCCTATAG CTGCCAAGTA GCCCCAGGGA GTAGTGGAAG GCAGATC      1080

ATCTGGCCAG AATCATGGGC ACTGCCTGTC CCCAAAGATG CCATAAGCTT TTAGACAG     1140

GCTTCAGGCT TTTCTCCCAG GTAAGGGGTT GAACCCCTAA CGATGGAAAG GAAATTAA     1200

TGGGCATTAC CTATTTTAAA ACTGTTTACA CACAGGTGCC TCACAGCATT TTTTGTTC     1260

GCCGCTGCCA TCCATGGAGC AGGTAGATAG AAGTGCAGAG TGCCCAGGCT AGAGGGAT     1320

GACAGGGACA GTGCAGGGAG GGAGCTGAGC CCCCTTCCAG CGGGGGCAGC AGAGGGGA     1380

GCCATGGGAG GGGCTGCAGG ATGTGTCTGA GCTGAAGCTT ATCAACAAGT AATGAGTA     1438
```

(2) INFORMATION FOR SEQ ID NO: 38:

(i) SEQUENCE CHARACTERISTICS:
        (A) LENGTH: 2387 base pairs
        (B) TYPE: nucleic acid
        (C) STRANDEDNESS: single
        (D) TOPOLOGY: linear (xi) SEQUENCE DESCRIPTION: SEQ ID NO: 38:

```
CCCCTTTTGG CTGTGTGTGC AGCAGGGCCG TGGAGGCTGC TTTTAGTCCA GGTAGACCAG      60

GGCCACGCTG AGGTCCCAGT GGGCTGAGCT GGTGACTGAT GAGTTGGTCC TCAGGGGTG      120
```

-continued

```
GGCTGGTGGG AAGTGATGTC ACTGTCCCGC CGATGGCCAG CTAAGGGACT GGGTTAGGA      180
CAGCCCCCTC TTGTCCTTCA CTCTCCCATC CTTGGCCAGG AGAAGAGGAA CAGGTCTTT      240
TGAGGACCTG CTTGTAGACC TTTGGGTAGG AGGGGACTTC CCAGGTTCTC TGTTGAGGC      300
ACTCTATCTA AAATAGCACC CCAGTGAGTC TCCTATCACT GTATCCTAAC ATTATTTTC      360
CCATGGCCCT CATCATTACC TGCTGATATA CTGTATGTTT GTCTATATAT CATCTAACA      420
CCCTCACACT GGAACACAAT GCCCGTGGGC AGAGACTTTG CTAGCCTTGG TTCCAGAGC      480
TAGAACAGTG CCTGGCAAGT AGGAGACACC CAGCATTACC TTTCTAAGTG AACCAGTAG      540
GATGGGGGGA GACCGCAAGG CTATGCCGGC AGACCTGAGG GAGTCCTGTC TGCATGCGC      600
GCAGGATGAC CTGAGGGGAA CTCCTTGGAC TTCTGTGCCC TCTTTATCTG TAAGGTGGC      660
ACCTGATCCC TTCCAGCGTA GGCATGAAGT AGCCTAATGA AGAGCATTCA GGCTTGGGT      720
TCAGTCTCAG GATCCTGGGG GCCTTAGAAT TTGTGGCGCT TGGGGACACC TTGTGATCG      780
GCAATTTCTG TTGTCTAGTT CATCCATGGC TGGTTGATCA TGTCTTCACT GATGCTGCT      840
TTCCTCTTCA CCTATATCTA CCTTGGGTAA GTGACAGATA AGCAGCAGGG TCCCTGGGA      900
CCCCTCTCCA TGTGGCACAA GTGGACATGG GCATGAGGAC CTGGGCGGGG AAAGATGAC      960
ATCGAGCTCC AGTCTTCCCC AGTGCCAGCC GTTTTGGGAA CCCAGGCCTC CGTCGCCC      1020
TCTCATGGCC TTGACACAGG GGAGTGGAAG TGGGGCTGCA TGGTGGACCA CATGTTTC      1080
TCTCGTTCCT GATTTAAAAT GAACCCTTCA TGGAGAAGGC TCTCTGTGAA CCCCAGGG      1140
ATAGAAACCC CCCAAAATTT ACATTCTGAT TTTTAGGCTA GGCCTGGGTA CTTTCTGG      1200
TGTGGGAAAA ATTATCTGTT CTATCGCCCC TTGATTTGGG ATATCAGCCT GACCCAGG      1260
CCCAAAGAGA CTGGGAGGAC AAGAGAAAAC ACTTTCCCAA GGACCTTTCC ATGTGCAC      1320
GGTCTTCCAG GTCATGCCCA TGCACATTTC TGTGATCTGT TCCAAGCATC CCCACCTT      1380
TTTAGAAAAT GCTGCAAATG GTAAATTGTA AGGACAGTGA AGGTCGGGGA AGGAAATG      1440
AGTAAAGAGG GCCAGGTTGG GACTGAATGG TGGTAAACTG CTAGGCTGTA ATGCCTCC      1500
TGAGTCCCAG TCACAGGCTC CACCTTGGTC CTGCAGGGAA GTGCTCAAGA CCTACAAT      1560
GGCCATGGAC TACCCCACCC TCTTGCTGAC TGTCTGGAAC TTCGGGGCAG TGGGCATG      1620
GTGCATCCAC TGGAAGGGCC CTCTGGTGCT GCAGCAGGCC TACCTCATCA TGATCAGT      1680
GCTCATGGCC CTAGTGTTCA TCAAGTACCT CCCAGAGTGG TCCGCGTGGG TCATCCTG      1740
CGCCATCTCT GTGTATGGTA GGTGGGCAGC AAGGCTGGTG GGGGCAGTGG GGGCGATG      1800
CAGGGCCAAA TCGTCCCCAG TGCTGCACAA GGAGGGCAGG TGCTGAAGGG CTTGCATC      1860
TTTCTGCAGA GGCCTGGGTG GGATCCCTCC TGAGAGAGTC GCCTTTGTAA AACAGAGG      1920
GGTCCACTAT TTCTGAACA CTCCTGGTGG TCTAGATAAA ACGCAGTAGT CACTGAGC      1980
CTCATTTACT TTTTTTTTTT TTGAGATGGA GTCTTGCTCT GTCGCCCAGG CTGGAGTG      2040
GTGGCGCCAT CTTGGCTGAC TGCAACCTCC GCCTCCCGGG TTCAAGTGAT TCTCCTGC      2100
CAGCCTCCTG AGTAGATAGG ATTATAGGCA TGTGCCACCA CGCTGGGCTA ATTTTTGT      2160
TTTTAGTAGA GATGGGGTTT CACCATGTTG GCCAGGCTGA TCTCGAACTC CTGACCTT      2220
GATCGGCCCG CCTCAGCCTC CCAAAGTACT GGGATTACAG GCATGAGCCA CTACACCC      2280
CCTCATTTTC CATTATTACT GCTATGCTGA TTGAGCAAGT GCACTGTTAA GCACTGGA      2340
CGCTGTAAGT GATTTGTTCA TCAAGACAGT CCTTTGGGTA CCATGCA                  2387
```

(2) INFORMATION FOR SEQ ID NO: 39:

(i) SEQUENCE CHARACTERISTICS:
    (A) LENGTH: 2058 base pairs
    (B) TYPE: nucleic acid
    (C) STRANDEDNESS: single
    (D) TOPOLOGY: linear (xi) SEQUENCE DESCRIPTION: SEQ ID NO: 39:

```
AGTCCACCCG GGGCTCCTGT GCTACAGGGC AGGCTCTTCT TCAGGGGGCT GCCCGGGGAT      60
AGTTTGACAA GGATGTCTCT GTCTTCCTAG ATCTCGTGGC TGTGCTGTGT CCCAAAGGG      120
CTCTGAGAAT GCTGGTAGAA ACTGCCCAGG AGAGAAATGA GCCCATATTC CCTGCCCTG      180
TATACTCATG TGAGTGAGCC CCCCGTGCCT CTGCCTGACT CGGGGTCAGC AGGCAGCCT      240
TGGGGGGACA GGGGCCTGCT TCCTGGCCGT GGCTTTCAGA GTTGACTGGG CGATCCCAG      300
AGGGTCTCCA CTTTCAGAAG CCAGGGAGGG CAGTATCTTG TTATTACACA GTAAGAAGC      360
TAGAAAGTTA GGACAGGAAG CAGGCATCTG CTGGGATGTG CTGCAGTCCC TGACTTCAT      420
CCGTCCATCC TCCAGCGGCA TGCTGCGGTG CAGGTTGCAT TCCTGTGATC CCGCAGCCA      480
CCCTCAGCTC TCCAGGCTCT TGAGAAGGGA CTTTGGAGAG GGATTCTTCA GGGCAGGGG      540
TCGGGGAGCA AGGAGCTTCT GGGCTTCCTT GACAGCAGCG TGGCTGATTG GCATTAATC      600
TAACTGAAGG GAAGGCACAC GGGATGGCCC CTGGCCTCGG GGTCAATGTG TAGAGATTT      660
GACTTACACA TGCAGTCAAC AAAGGCACAT CAAGTCCCCA TTTTGTGACA GGCACTGTG      720
TAGGCATTGG GGGACCCAGC AGGAAAGAAG ACCACAGGGT CCCAGGCCTC ATGGAGCTC      780
CGGCCCTGTG ATTGTGATGC CCTCGGTCTG TTGATGGCGG GGCTTAAATA GCCTGAATT      840
CTGGAGCTCT GGCGTCTGCA AGGTGGCCTG GGAAAGAGTT TATGGAACAG CTACAGAGT      900
CTAGGTACCT TCATGCAGTT GAGGATTCGA GCCCGTAGAG GAGAATTGCC TGCAGCGTG      960
CCCCACGGGA AAGCACATTC CAGGCGCATT CCGAGGATGA GCGGAGACCA TGTATGGA      1020
GGTAGTGCCA GGACTGTCAT GAGTGTCCCA GGGCTCGGGG GATTCACCCG TGAACAGT      1080
GGTCTTGGCT CTGATAGACC TGGTTCTTAT GCTTTAGGAG GGGAGACAAA CAGTAACA      1140
ATAGACAAAT GCAAGAGAGA GTGACTCTGG ACCCCTCCCA CAACGGCCTC CTAACAAT      1200
AGCATGAGCA GATACCTGCA GGATGGAGGG TCCTGTGCAG GCTTTCTGGG ACGCAGAC      1260
GCCACCTCCC CCAGGCCCTG CAGGCAGCCA CTGTTAGCAC CGCCTGAGAC GTGAACCT      1320
TCTCCTCCCC CAGCTGCCAT GGTGTGGACG GTTGGCATGG CGAAGCTGGA CCCCTCCT      1380
CAGGGTGCCC TCCAGCTCCC CTACGACCCG GAGATGGGTG AGTATCTTGG GGAGCTAA      1440
GCCTCTCATC ACTGGGGGC AGCTCCCTAC CTGCACCCAG CTCTGCTCGG CCTGGCTT      1500
CTGAGAGGCA TGAGTTCAGG AGGGGCAGAG GGAAAGGTCC GTTGAAAACC AGCCGGAC      1560
ATGCGGCTTG AAGATTGAGC AAGTGTTGGA CCCTCGGTCC TCTGCCAGCC TCTGTTGC      1620
CGTTCTGCTG GGCGTGGGTG GGTGGAGTGG GGGAAGCCCC GGTGTCAGGT GCTGGTGC      1680
AGGGGGACCC CTTCTTGGAG CTTTGTTCCC TGGTAACACT CTGACCAGCT GTTGTTTC      1740
TCTCTTGTTG TCCCCTCCTC ACGGTGATGA CGGACATCTT CTCTTCCTGG ACACCCAG      1800
GAAGACTCCT ATGACAGTTT TGGGGAGCCT TCATACCCCG AAGTCTTTGA GCCTCCCT      1860
ACTGGCTACC CAGGGGAGGA GCTGGAGGAA GAGGAGGAAA GTAAGGTGCC CATGTTCA      1920
CGGCCTGCTT CAGCCTACGG CGGGAGCGGA GACAGAGGGT GGAGGCTCCC TGCAGCCT      1980
GTGGAGGAGG GCATGAGGGG AGGGGCCCCT TTTCCCATCA GAGGCATCTC TGTGAAAG      2040
GAAGATGCCT GCAGCGCT                                                    2058
```

(2) INFORMATION FOR SEQ ID NO: 40:

(i) SEQUENCE CHARACTERISTICS:
        (A) LENGTH: 4004 base pairs
        (B) TYPE: nucleic acid
        (C) STRANDEDNESS: single
        (D) TOPOLOGY: linear (xi) SEQUENCE DESCRIPTION: SEQ ID NO: 40:

```
CAGGGTCTCG CTCTGTTGCC CAGGCTGGAG TGCGAGTAGC ACGATTGTGG CTCACTGCAA      60
CCATGACTTC CTGGGCTCAA GTGATCCTCC CACCTTGGCC TCCTGAGTAG CTGGGATTA      120
AGGCACGTGC TACCACACCT GGCTCATTTA TATTTTTAGT AGAGACAAGG TTTTGACTT      180
TTGCCCGGGC TGGTTTCGAA CTCCTGGGCT CAAGTGATCC ACCTGCCTTG GCCTTCCAA      240
GTACTGGGAT TATAGGTCTG AGCCACAGCA CCTGGCCAAA ATTAGTTTTA TTATAAGAG      300
TGCAACTCAG GACCACCCAA ATGAAGAGAC AGTGAAGAAG TAATGCTGAT GGATCACAC      360
TGGTGGGGA AGGCGGACAG CTGGGGCCAG GAGCAGGAGG GACACCTGCA GGGCTGGAA       420
GGCAGGGGAG GTGGGCCCCC ATGGTTTGTG TTTATTGCAT AACCATTTTT ATTGTCTAC      480
GTGAGCAAAG TTATCCTATA AACAAGTGTC AGGGACCATT GCACTAAAGA AAACAAATG      540
GAGCATTTTG GAAGCTCTAA TTTCCTGATC AGTAATGGGT AGACTAATTC CCAGTTATA      600
TTACCTGTTG TAAGGTGAAA GGTTCTTCAG AGGACCTCTG TCTTGGTGTT ATATGGGCT      660
TTGAATGTAC TGAAATTAAA TTCCCTAAAA ANCTGTGATT CAGACTTCAT ACTAAATTG      720
ACAGCAGTGC CCAGCCCAAG GCCTTGCATT TCTATTTGTT GTTTTCTTTA CTCTCTAAG      780
GCCCAACACT GGTTTTACCT GAGTTTCAGA ACTGCCCGCT TTTCTCTGCC CAGGTTGTA      840
GTCACCCAGT CCACAGGTGT CCCCTGCTTT CCCACTGGCC ACTGATTTGG GGAGGCAGC      900
GTCCATGTCC CCAGTCCACA TCTTAGCTTC TAGAGGCCAG GTGGGTGGG CTGGGCTGG      960
CAAGAGCAGC TGGGCCTTCT GGGCCAGAGT TTCTCTTCTT TTTCCATTCT GTGCACGC     1020
CTTCAGTACG GGTTACTGTC TCTCCTCACA CAGGGGCGT GAAGCTTGGC CTCGGGGA      1080
TCATCTTCTA CAGTGTGCTG GTGGGCAAGG CGGCTGCCAC GGGCAGCGGG GACTGGAA     1140
CCACGCTGGC CTGCTTCGTG GCCATCCTCA TTGTGAGTGG CTGGGATGC GTCCAACT      1200
CTCGTGGTGG GGGCCCCCAG GGTCCTCATT GTGGTGGGGG CAGGTCTCAG GATCCCTA     1260
GATTTTTCAT TTCTTCTCTT CCCTCTGAGG ACAAGAGCA GGGAGCGGGG CTGGAAGG      1320
CAGCTTGAGA CCAAGGCTCA CAGGAGGTGT GCTCGCCCCT AGGTGGGCTC CAGCCTGT     1380
AGGACAGTGC AGGGGAGGGT GAGGAGTGTA CCGGCCCCAG CGTGGCTGAG CACACAGC     1440
CCAGGCCGAG GACCCAGCTG ACAGCTTTGC GCAGTGATGA TACCCTCGAG GTGGTTGT     1500
TGACATCAGA TTTGCAGAAA AGAAAATTGC TTAAGGGCCT TGCCCATGGG CGCAAAGC     1560
GTGAGGACCA TGTTTTCCCC CTCCTCCATG CCATTGGGAC ACCACAGGGT CTGAATCT     1620
GGCACTAGGG GTGGCCCCGT TACTGTGAAC CACAGCAGTG AAATGTGGAG GCCCTGTA     1680
CAGTTAACGT GGCCAGATAC ACATAATGGG GAGACGTCCG GCCGTGACTT CATCTCAG     1740
ATTTCGCTGT CACGTTAGAG GAGGAGGAGC GTCTGAGCCG TGCGCTTGGC ATCTGCCC     1800
TAGTGAAAAC CCTGGGCATG GCATGATTAA GGTTGATGCT CCAGTGTCCA GAAGGTTT     1860
TTTTTGCCCA CAAGTATATC AGGGATGGGA TGGTGGACCC AGGCTCCTCC ACCACCAG     1920
TGCCTTACCT GAGCCCTGCT GGCCCCAAAG ATATAGAAGG CACCCTGGTT CCCTGTGC     1980
ACCTGGACCA CTGCCTGCAT CAGCTGGGTC AGGGGAGGAT GGGCAGCCCC CACACCTG     2040
```

```
TCCCAGGGGC AGGTTGCCTG GCGGCTCTGA TTCCCTTGGT GCCAGCTGCT GAGAACCT    2100

CTGCCATTTC AGTTGAGCCC ACCTAGCTCT CATATAAATA CATGTTCCCT GAGGGCAT    2160

TACCATCCCA TGTGACCACT CCAGCCAGAC AGGGGAGGCA GCACGGCCTC GGGGCACA    2220

ACTGCTCCAG GAGTCAGGAG GCCTGCCTTC TGGTTCACTC ACTAACAGGT GAGGTGAT    2280

AATGGGGGTG CGAACTTCTG ACCTTAACAC CTCAAGAGCT GTTGCAGGAC CAGGGAAG    2340

AATGGGGTGT CTAGCGCCGT TATCCGACTG GTCCTCGAAC AAGCTCCTGT GCCCAGGG    2400

TAGACCATGA CTCACAGCTC CTGTCCACAC CAGGGATCAC CACGCTCACC CTCCCCTC    2460

TGTCCTGCAG GGCTTGTGTC TGACCCTCCT GCTGCTTGCT GTGTTCAAGA AGGCGCTG    2520

CGCCCTCCCC ATCTCCATCA CGTTCGGGCT CATCTTTTAC TTCTCCACGG ACAACCTG    2580

GCGGCCGTTC ATGGACACCC TGGCCTCCCA TCAGCTCTAC ATCTGAGGGA CATGGTGT    2640

CACAGGCTGC AAGCTGCAGG GAATTTTCAT TGGATGCAGT TGTATAGTTT TACACTCT    2700

TGCCATATAT TTTTAAGACT TTTCTTTCCT TAAAAAATAA AGTACGTGTT TACTTGGT    2760

GGAGGAGGCA GAACCAGCTC TTTGGTGCCA GCTGTTTCAT CACCAGACTT GGCTCCC     2820

TTTGGGAGC GCCTCGCTTC AACGGACAGG AAGCACAGCA GGTTTATCCA GATGAACT     2880

GAAGGTCAGA TTAGGGCGGG GAGAAGAGCA TCCGGCATGA GGGCTGAGAT GCGCAAAG    2940

TGTGCTCGGG AGTGGCCCCT GGCACCTGGG TGCTCTGGCT GGAGAGGAAA AGCCAGTT    3000

CTACGAGGAG TGTTCCCAAT GCTTTGTCCA TGATGTCCTT GTTATTTTAT TGCCTTTA    3060

AACTGAGTCC TGTTCTTGTT ACGGCAGTCA CACTGCTGGG AAGTGGCTTA ATAGTAAT    3120

CAATAAATAG ATGAGTCCTG TTAGAATCTT GGAGTTTGGT CCGTTGTAAA TGTTGACC    3180

TCTCCCTGCA TCTTGGGCAC CCCTGGGATA ACTTGTGCTG TGAGCCCAGG ATGGAGGC    3240

TTTGCCCTGT TTGAAGGAAC TTTTAATGAT CTCGCCTCTC TGCACACATT TCTTTAAC    3300

GAAAGTTTCC TAAGCAAAGG AGTTAGGAGA GCAGGGTGGC CTGACATCTG CCAGCCCT    3360

GCTGTAAGGC TGTGGATGCT GAGCAGGTCC CTGGACTCAG TTGTGCACGG TGGCACAG    3420

ACTGACCAGG TGGTTGCCAA ACATCCAGT GGTTCCTTCA GCAAGTGTTC ACCCTCTG     3480

GAAGCCTGTG AGGGCCTGAG CTCAGAAACC ACTCTCCTTT CCTTCTCTGG CTTTGGCC    3540

GGGCACTGTG GTGGGAGAGT GGACAGTTTG GCTTTGCCTT CTCTGTACAT CAATCATG    3600

TTGCAAAGAG AATCTCAGAA GTGCCTCTTC CTGAGCACAG TGGCTCACAC CTGTAATC    3660

AATACTTCGG GAGGTCGAGT CGGAAGGATC ACTTGAGCCC AGGAGTTTGA GACCAGCC    3720

GGCAACATAG TGAGACTTTG TACAAAAAAA AATTTAAAAA TTAGCCAAGC ATGGTGGC    3780

GCATCTGTAG TCTCAGCTAC TCTGGAGGCT GAGGTGGGAG GATCACTTAA GCCCAGGA    3840

CTGAGGCTGC AATGAGCCGA GATCAAGCAG GTGTTAGGTA TATCAGACAG CTGAGAAG    3900

GCAAGTGTGC CCTGGGGTTC AAACTGGTAC CCCTGTCTCC CTGTTCCAGG AATAACAT    3960

GTGCCGGGAC AATGCATCTT TATTATGAGA GGAATGAGAA TTGT                   4004
```

(2) INFORMATION FOR SEQ ID NO: 41:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (xi) SEQUENCE DESCRIPTION: SEQ ID NO: 41:

```
Leu Leu Asn Ser Val Leu Asn Thr Leu Ile Met Ile Ser Val Ile Va
1               5                   10                  15
```

Val Met Thr Ile
        20

(2) INFORMATION FOR SEQ ID NO: 42:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (xi) SEQUENCE DESCRIPTION: SEQ ID NO: 42:

Leu Leu Asn Ser Val Leu Ile Thr Leu Ile Met Ile Ser Val Ile Va
1               5                   10                  15
Val Met Thr Ile
        20

(2) INFORMATION FOR SEQ ID NO: 43:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 43:

GTGGGGCAGA CGGAGAGAA                                                        19

(2) INFORMATION FOR SEQ ID NO: 44:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 44:

AACACCGTTC ATACCTT                                                          17

(2) INFORMATION FOR SEQ ID NO: 45:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 45:

CAATTGTCTG GGTATCA                                                          17

(2) INFORMATION FOR SEQ ID NO: 46:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 46:

CTTTGTCTCA CAGGAAA                                                          17

(2) INFORMATION FOR SEQ ID NO: 47:

(i) SEQUENCE CHARACTERISTICS:
        (A) LENGTH: 17 base pairs
        (B) TYPE: nucleic acid

```
            (C) STRANDEDNESS: single
            (D) TOPOLOGY: linear (xi) SEQUENCE DESCRIPTION: SEQ ID NO: 47:

CGTGCATTAC ATGGATA                                              17

(2) INFORMATION FOR SEQ ID NO: 48:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO: 48:

GTCCAGAATC ACTCAAG                                              17

(2) INFORMATION FOR SEQ ID NO: 49:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO: 49:

ATCAGTCTCA GGATCCT                                              17

(2) INFORMATION FOR SEQ ID NO: 50:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO: 50:

GCTGACTGTC TGGAACT                                              17

(2) INFORMATION FOR SEQ ID NO: 51:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO: 51:

CCAGTCAACT CTGAAAG                                              17

(2) INFORMATION FOR SEQ ID NO: 52:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO: 52:

CTTGCTCAAT CTTCAAG                                              17

(2) INFORMATION FOR SEQ ID NO: 53:

(i) SEQUENCE CHARACTERISTICS:
            (A) LENGTH: 17 base pairs
            (B) TYPE: nucleic acid
            (C) STRANDEDNESS: single
```

(D) TOPOLOGY: linear (xi) SEQUENCE DESCRIPTION: SEQ ID NO: 53:

CCTGGTAACA CTCTGAC                                                          17

(2) INFORMATION FOR SEQ ID NO: 54:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO: 54:

TCCACATCTT AGCTTCTAG                                                        19

(2) INFORMATION FOR SEQ ID NO: 55:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO: 55:

CTAGACCATG ACTCACAG                                                         18

(2) INFORMATION FOR SEQ ID NO: 56:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO: 56:

AGAGGGGTCA ACATTTAC                                                         18

(2) INFORMATION FOR SEQ ID NO: 57:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO: 57:

GGCGTTTTGT TCTTCTTCTC TC                                                    22

(2) INFORMATION FOR SEQ ID NO: 58:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO: 58:

ACCAAAGGGT ACAGAGTTTT CCC                                                   23

(2) INFORMATION FOR SEQ ID NO: 59:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO: 59:

CATCCCCAAG TGGTATGTGT TA                                        22

(2) INFORMATION FOR SEQ ID NO: 60:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 60:

CTCCCCAGCC GTGCTTGTG                                            19

(2) INFORMATION FOR SEQ ID NO: 61:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 61:

CGTTTGATTG ACAGGCATCT CT                                        22

(2) INFORMATION FOR SEQ ID NO: 62:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 62:

CAAGGTGGCA GAGTGGACAG                                           20

(2) INFORMATION FOR SEQ ID NO: 63:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 63:

CATATGCCCT AGTAGCTCAT AG                                        22

(2) INFORMATION FOR SEQ ID NO: 64:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 64:

CCATTATACG AACAAGGAAG CTG                                       23

(2) INFORMATION FOR SEQ ID NO: 65:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 65:

GCTCATGGGG ATGGTGCCC                                          19

(2) INFORMATION FOR SEQ ID NO: 66:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 66:

GAAGCCGCTG TCTAAAAGCT TAT                                     23

(2) INFORMATION FOR SEQ ID NO: 67:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 67:

CCCTCCCAGC GTAGGCATGA A                                       21

(2) INFORMATION FOR SEQ ID NO: 68:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 68:

GCAGAAAGGG ATGCAAGCCC                                         20

(2) INFORMATION FOR SEQ ID NO: 69:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 69:

GGCATGCTCT GAGAGCTCCA                                         20

(2) INFORMATION FOR SEQ ID NO: 70:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 70:

GCCCAGAAGC TCCTTGCTCC                                         20

(2) INFORMATION FOR SEQ ID NO: 71:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 71:

TGGACCCCTC CCACAACGG                                                19

(2) INFORMATION FOR SEQ ID NO: 72:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 72:

TCACAGAGAT GCCTCTGATG G                                             21

(2) INFORMATION FOR SEQ ID NO: 73:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 73:

ACTGGTTTTA CCTGAGTTTC AGA                                           23

(2) INFORMATION FOR SEQ ID NO: 74:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 74:

CGAGCACACC TCCTGTGAG                                                19

(2) INFORMATION FOR SEQ ID NO: 75:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 75:

GGTGTCTAGC ACCGTTATCC                                               20

(2) INFORMATION FOR SEQ ID NO: 76:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 76:

ACAGGACTCA TCTATTTATG GATA                                          24

(2) INFORMATION FOR SEQ ID NO: 77:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO: 77:

```
GAGATGGAAG AC                                                           12

(2) INFORMATION FOR SEQ ID NO: 78:

(i) SEQUENCE CHARACTERISTICS:
          (A) LENGTH: 14 base pairs
          (B) TYPE: nucleic acid
          (C) STRANDEDNESS: single
          (D) TOPOLOGY: linear (xi) SEQUENCE DESCRIPTION: SEQ ID NO: 78:

AGATGGAAGA AGAC                                                         14

(2) INFORMATION FOR SEQ ID NO: 79:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (xi) SEQUENCE DESCRIPTION: SEQ ID NO: 79:

CTGCCATGGT GTGGACGGTT                                                   20

(2) INFORMATION FOR SEQ ID NO: 80:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (xi) SEQUENCE DESCRIPTION: SEQ ID NO: 80:

CTCCAGCTCC TCCCCTGGG                                                    19

(2) INFORMATION FOR SEQ ID NO: 81:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (xi) SEQUENCE DESCRIPTION: SEQ ID NO: 81:

GGACAAAGCA TTGGGAACAC T                                                 21

(2) INFORMATION FOR SEQ ID NO: 82:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (xi) SEQUENCE DESCRIPTION: SEQ ID NO: 82:

TGAGGGACAT GGTGTGCCAC AGG                                               23

(2) INFORMATION FOR SEQ ID NO: 83:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (xi) SEQUENCE DESCRIPTION: SEQ ID NO: 83:

GAACTGAGAA GGTCAGATTA                                                   20
```

(2) INFORMATION FOR SEQ ID NO: 84:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 84:

ACAGGACTCA TCTATTTATC CATA                                              24

(2) INFORMATION FOR SEQ ID NO: 85:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 85:

ATTGGATGCA GTTGTATAGT                                                   20

(2) INFORMATION FOR SEQ ID NO: 86:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 86:

TAATCTGACC TTCTCAGTTC                                                   20

(2) INFORMATION FOR SEQ ID NO: 87:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (xi) SEQUENCE DESCRIPTION: SEQ ID NO: 87:

Glu Met Glu Asp
1

(2) INFORMATION FOR SEQ ID NO: 88:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (xi) SEQUENCE DESCRIPTION: SEQ ID NO: 88:

Glu Met Glu Glu Asp
1               5